United States Patent
Hamada et al.

(10) Patent No.: US 9,096,529 B2
(45) Date of Patent: Aug. 4, 2015

(54) METAL COMPLEX COMPOUND AND ORGANIC LIGHT EMITTING DIODE DEVICE INCLUDING THE SAME

(75) Inventors: Yuji Hamada, Yongin (KR); Kwan-Hee Lee, Yongin (KR)

(73) Assignee: Samsung Display Co., Ltd., Yongin, Gyeonggi-Do (KR)

( * ) Notice: Subject to any disclaimer, the term of this patent is extended or adjusted under 35 U.S.C. 154(b) by 313 days.

(21) Appl. No.: 13/168,760

(22) Filed: Jun. 24, 2011

(65) Prior Publication Data
US 2012/0012824 A1 Jan. 19, 2012

(30) Foreign Application Priority Data
Jul. 14, 2010 (KR) .................. 10-2010-0068017

(51) Int. Cl.

| | | |
|---|---|---|
| H01L 51/54 | (2006.01) |
| C09K 11/06 | (2006.01) |
| C07F 3/00 | (2006.01) |
| C07F 3/06 | (2006.01) |
| C07D 221/16 | (2006.01) |
| C07D 221/18 | (2006.01) |
| C07D 241/50 | (2006.01) |
| C07D 401/04 | (2006.01) |
| C07D 471/04 | (2006.01) |
| H05B 33/14 | (2006.01) |
| H01L 51/00 | (2006.01) |
| H01L 51/50 | (2006.01) |

(52) U.S. Cl.
CPC ............ *C07D 221/16* (2013.01); *C07D 221/18* (2013.01); *C07D 241/50* (2013.01); *C07D 401/04* (2013.01); *C07D 471/04* (2013.01); *C07F 3/00* (2013.01); *C07F 3/006* (2013.01); *C09K 11/06* (2013.01); *H01L 51/0077* (2013.01); *H05B 33/14* (2013.01); *C09K 2211/1011* (2013.01); *C09K 2211/1044* (2013.01); *C09K 2211/186* (2013.01); *H01L 51/0061* (2013.01); *H01L 51/0072* (2013.01); *H01L 51/0085* (2013.01); *H01L 51/5016* (2013.01)

(58) Field of Classification Search
None
See application file for complete search history.

(56) References Cited

U.S. PATENT DOCUMENTS

| 2005/0019605 A1 | 1/2005 | Kwong et al. | |
|---|---|---|---|
| 2007/0034863 A1* | 2/2007 | Fortte et al. ............ | 257/40 |

FOREIGN PATENT DOCUMENTS

| JP | 06-322362 B2 | 11/1994 | |
|---|---|---|---|
| JP | 07-197021 | 8/1995 | |
| JP | 09-176629 A | 7/1997 | |
| JP | 09176629 A * | 7/1997 | ............ C09K 11/06 |
| JP | 2000-012222 A | 1/2000 | |
| JP | 2000-100569 A | 4/2000 | |
| JP | 2000-208261 A | 7/2000 | |
| JP | 2000-357588 | 12/2000 | |

OTHER PUBLICATIONS

Machine translation of JP09-176629. Date of publication: Jul. 8, 1997.*
Machine translation of JP2000-357588. Date of publication: Dec. 26, 2000.*
Qiao et al. "High-efficiency organic to near-infrared emissions from bis-cyclometalated iridium complexes with phenyl-benzoquinoline isomers as ligands" J. Mater. Chem. 2009, 19, 6573-6580. Date of publication: Jul. 22, 2009.*
Extended European Search Report dated Oct. 17, 2011, issued by the European Patent Office, 6 pages.

* cited by examiner

*Primary Examiner* — Andrew K Bohaty
(74) *Attorney, Agent, or Firm* — Knobbe Martens Olson & Bear LLP

(57) ABSTRACT

Disclosed is a metal complex compound represented by the following Chemical Formula 1, and an organic light emitting diode device including the same.

CHEMICAL FORMULA 1

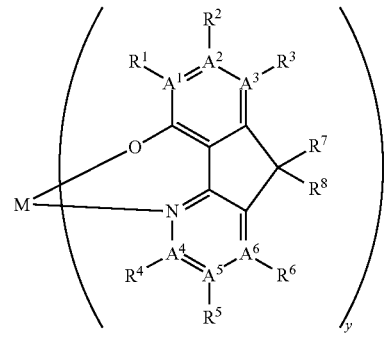

In Chemical Formula 1, M, $R^1$ to $R^8$, $A^1$ to $A^6$, and y are the same as defined in the detailed description.

5 Claims, 1 Drawing Sheet

METAL COMPLEX COMPOUND AND ORGANIC LIGHT EMITTING DIODE DEVICE INCLUDING THE SAME

CROSS-REFERENCE TO RELATED APPLICATIONS

This application claims priority to and the benefit of Korean Patent Application No. 10-2010-0068017 filed in the Korean Intellectual Property Office on Jul. 14, 2010, the entire contents of which are incorporated herein by reference.

BACKGROUND

1. Field

This disclosure relates to a metal complex compound and an organic light emitting diode device including the same.

2. Description of the Related Art

Recently, an organic light emitting diode (OLED) device has been drawing attention as a display device and a luminous device.

An organic light emitting diode device includes two electrodes and an emission layer interposed therebetween, and emits light when electrons injected from one electrode are combined with holes injected from another electrode in an emission layer to generate excitons that release energy.

Since the organic light emitting diode device emits light in itself without a particular light source, it has excellent response speed, viewing angle, and contrast ratio as well as low power consumption.

An organic light emitting diode device has been required to have increased luminous efficiency but decreased driving voltage.

SUMMARY

One aspect of this disclosure provides a metal complex compound being capable of increasing luminous efficiency and reducing a driving voltage.

Another aspect of this disclosure provides an organic light emitting diode device including the metal complex compound.

According to one aspect of this disclosure, provided is a metal complex compound represented by the following Chemical Formula 1.

Chemical Formula 1

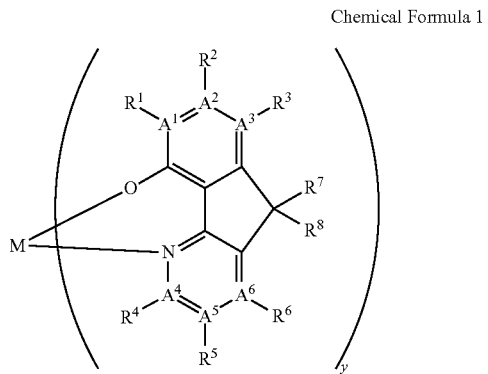

In Chemical Formula 1, M is a Group 2 metal ion or Group 3 metal ion, $R^1$ to $R^8$ are the same or different, and are hydrogen, a halogen, a hydroxy group, a substituted or unsubstituted C1 to C20 alkyl group, a substituted or unsubstituted C2 to C20 alkenyl group, a substituted or unsubstituted C2 to C20 alkynyl group, a substituted or unsubstituted C1 to C20 alkoxy group, a substituted or unsubstituted C3 to C30 cycloalkyl group, a substituted or unsubstituted C3 to C30 cycloalkenyl group, a substituted or unsubstituted C3 to C30 cycloalkynyl group, a substituted or unsubstituted C2 to C30 heterocycloalkyl group, a substituted or unsubstituted C2 to C30 heterocycloalkenyl group, a substituted or unsubstituted C2 to C30 heterocycloalkynyl group, a substituted or unsubstituted C6 to C30 aryl group, a substituted or unsubstituted C6 to C30 aryloxy group, a substituted or unsubstituted C3 to C30 heteroaryl group, an amine group, an ester group, a carboxyl group, a nitro group, or a cyano group, optionally, $R^1$ and $R^2$, $R^2$ and $R^3$, $R^4$ and $R^5$, and $R^5$ and $R^6$ are respectively bound to each other to form a substituted or unsubstituted C6 to C30 aryl group, a substituted or unsubstituted C6 to C30 aryloxy group, or a substituted or unsubstituted C3 to C30 heteroaryl group, $A^1$ to $A^6$ are the same or different, and are a carbon atom or a nitrogen atom, and y is 2 or 3.

In Chemical Formula 1, R1 to R8 are the same or different, and are hydrogen, a halogen, a substituted or unsubstituted C1 to C20 alkyl group, a substituted or unsubstituted C6 to C30 aryl group, a substituted or unsubstituted C6 to C30 aryloxy group, a substituted or unsubstituted C3 to C30 heteroaryl group, an amine group, an ester group, a nitro group, or a cyano group, and optionally, R1 and R2, R2 and R3, R4 and R5, and R5 and R6 are respectively bound to each other to form a substituted or unsubstituted C6 to C30 aryl group, a substituted or unsubstituted C6 to C30 aryloxy group, or a substituted or unsubstituted C3 to C30 heteroaryl group.

In Chemical Formula 1, M may be Be, Zn, Mg, Ca, Y, B, Al, Ga, In, or a combination thereof.

The metal complex compound may be represented by one of the following Chemical Formulae 2-1 to 2-147.

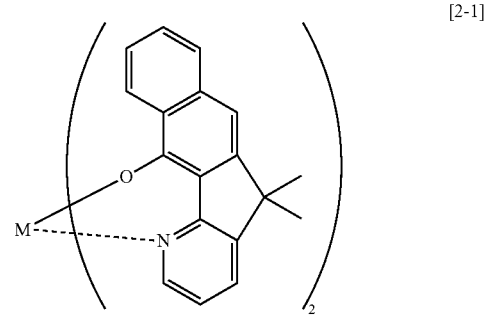

[2-1]

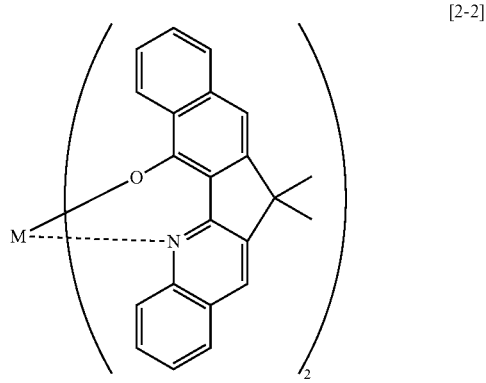

[2-2]

[2-3]
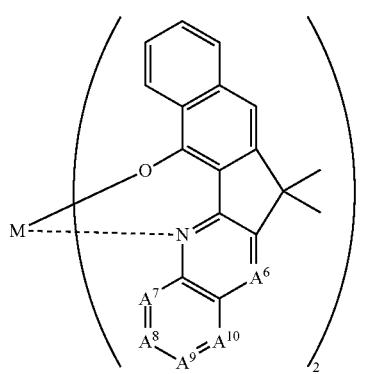
[2-4]
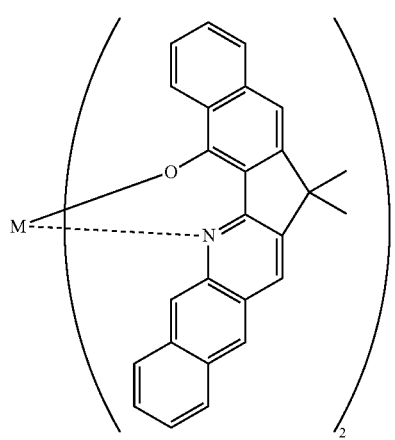
[2-5]
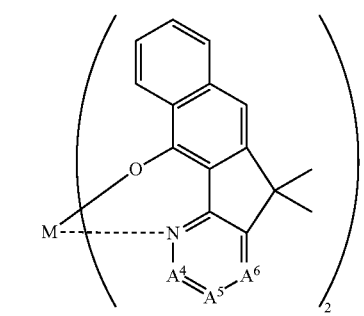
[2-6]
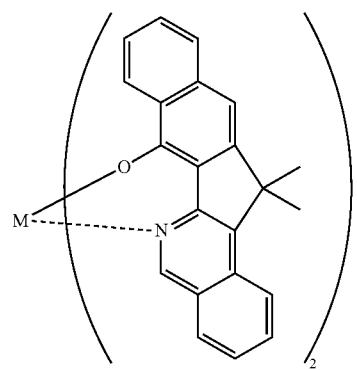
[2-7]
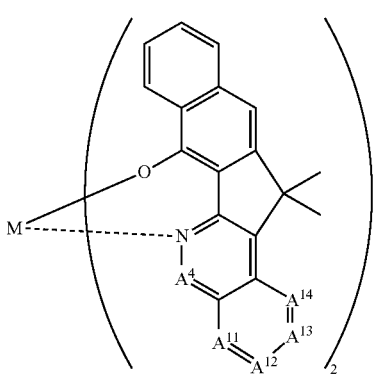
[2-8]
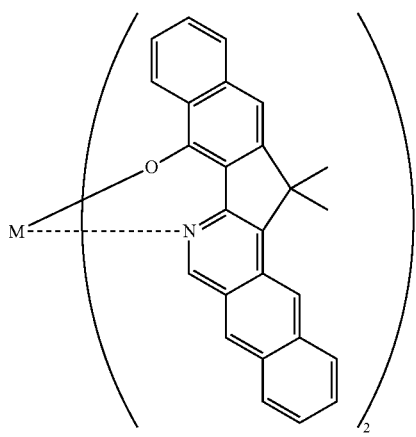
[2-9]
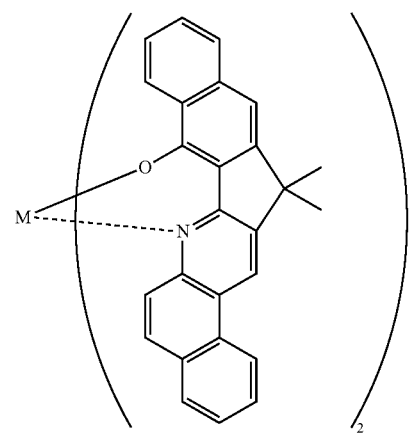
[2-10]
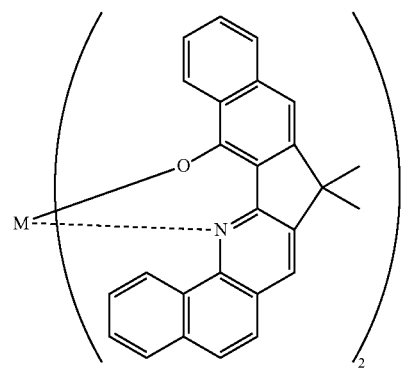

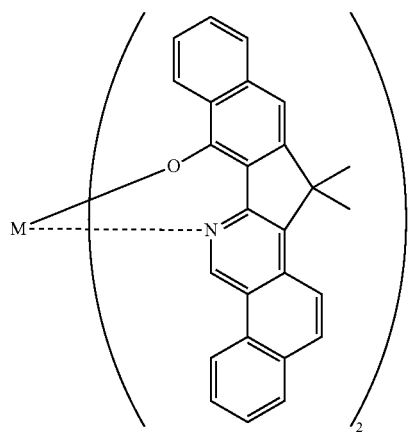
[2-11]
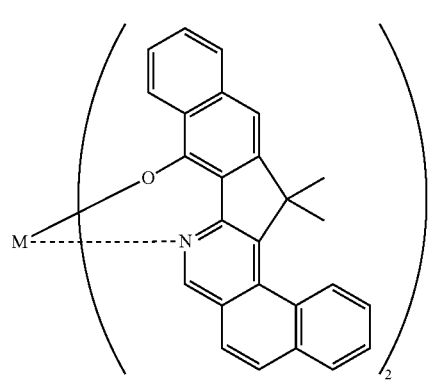
[2-12]
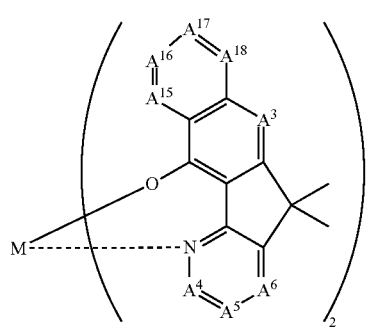
[2-13]
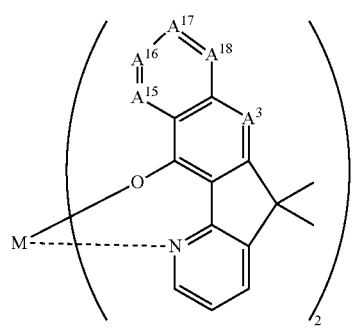
[2-14]
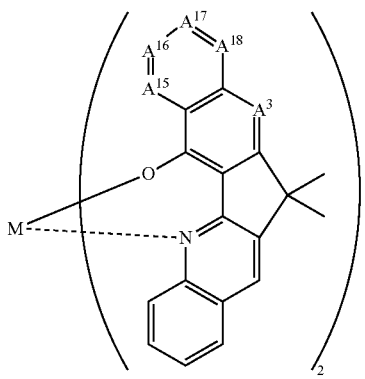
[2-15]
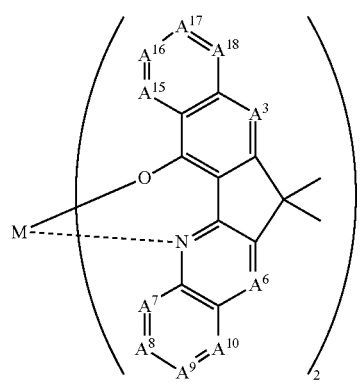
[2-16]
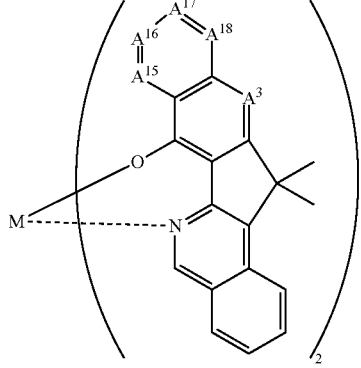
[2-17]
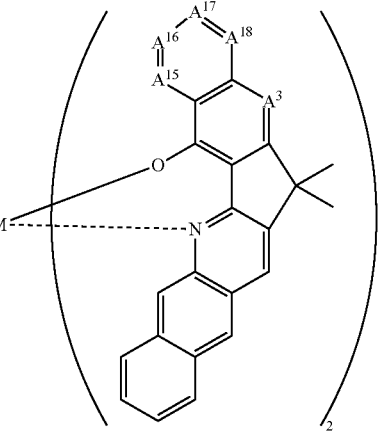
[2-18]

[2-19]
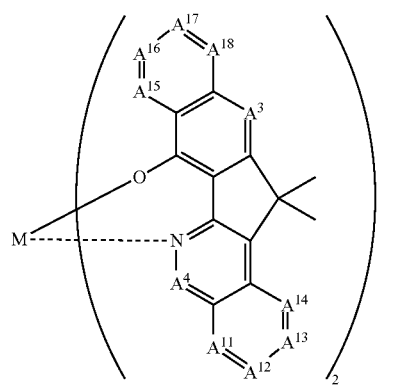
[2-20]
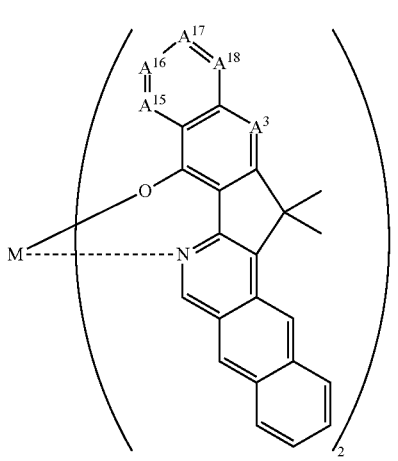
[2-21]
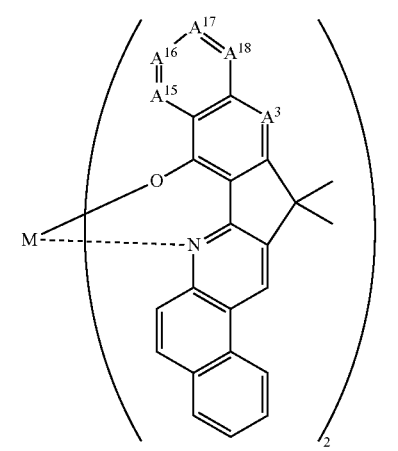
[2-22]
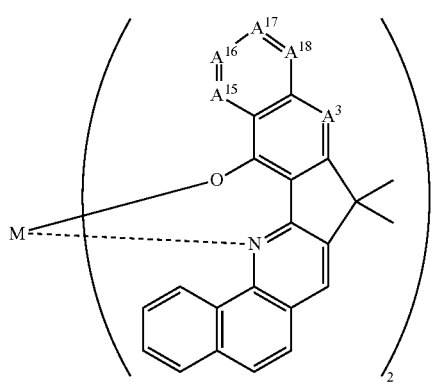
[2-23]
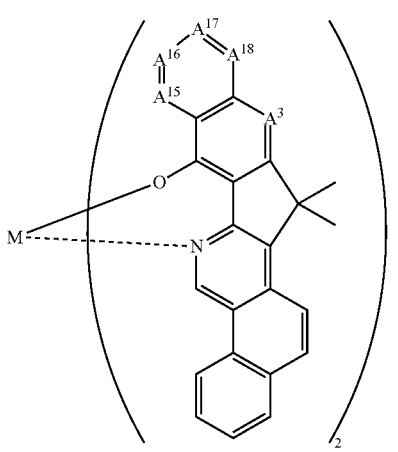
[2-24]
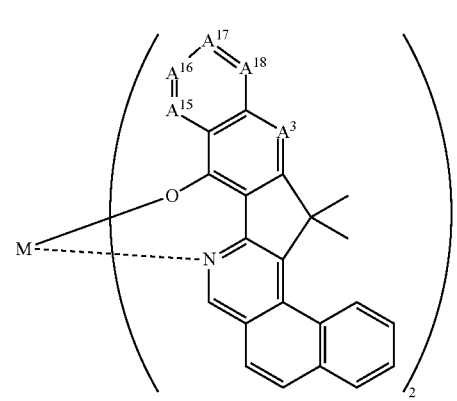
[2-25]
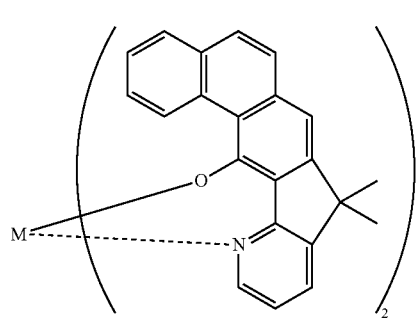
[2-26]
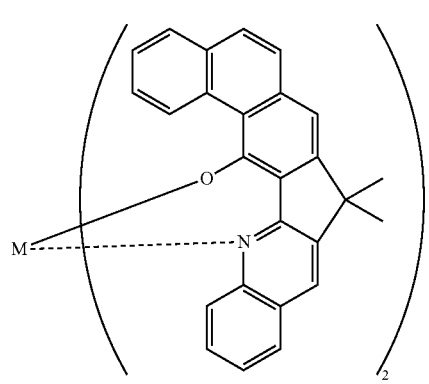

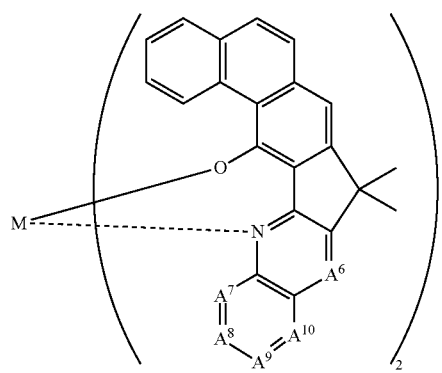
[2-27]
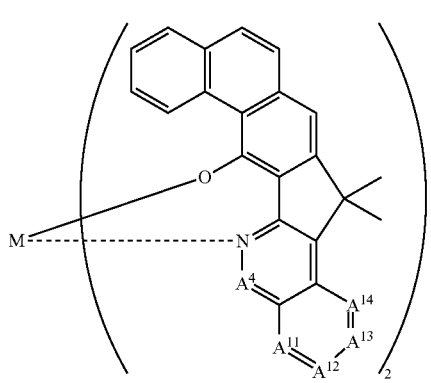
[2-31]
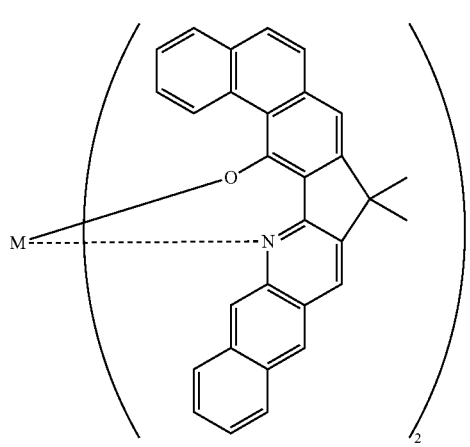
[2-28]
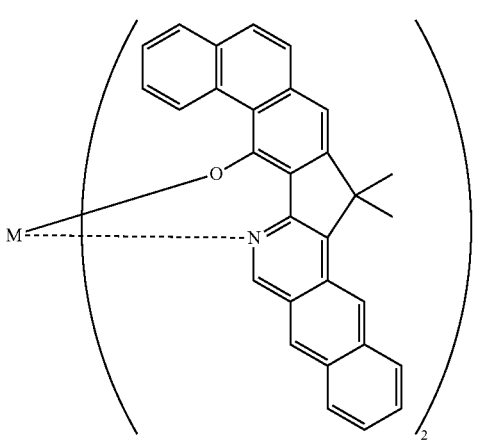
[2-32]
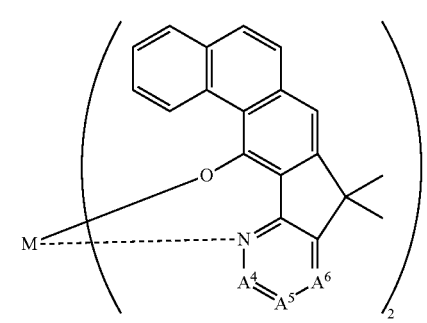
[2-29]
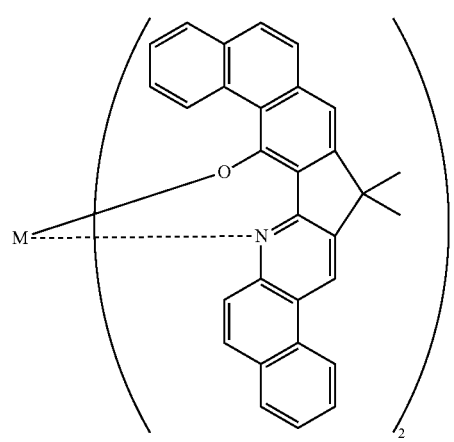
[2-33]
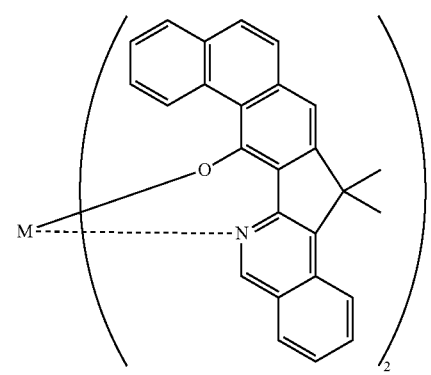
[2-30]
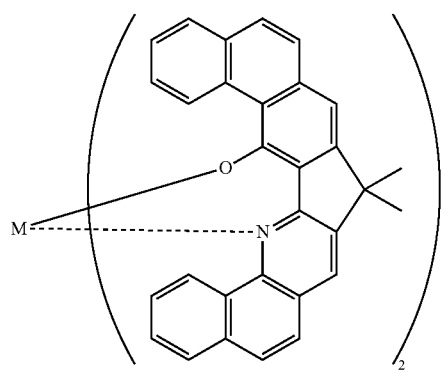
[2-34]

[2-35]
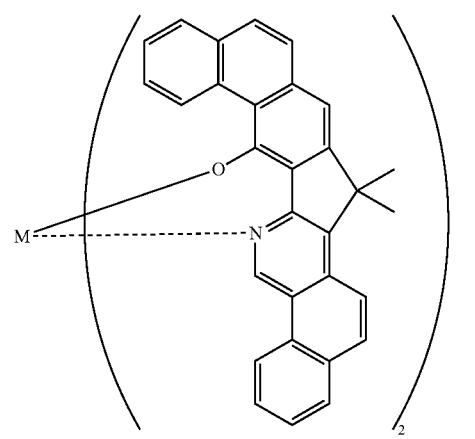
[2-36]
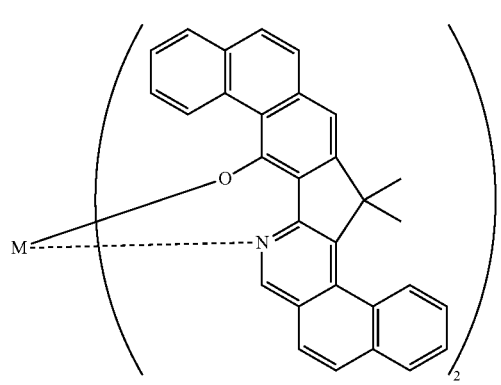
[2-37]
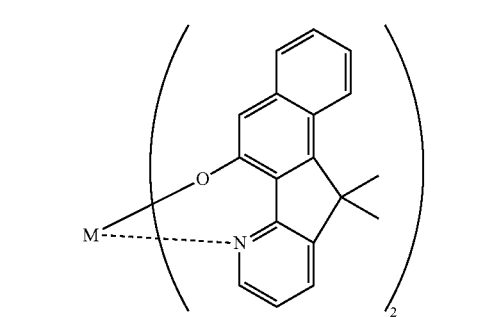
[2-38]
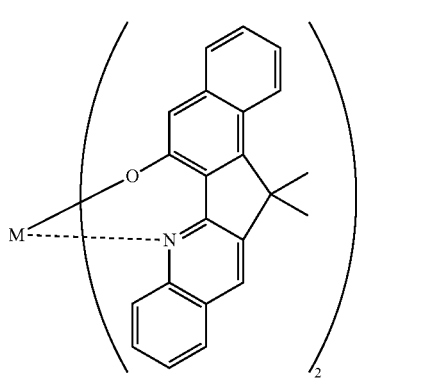
[2-39]
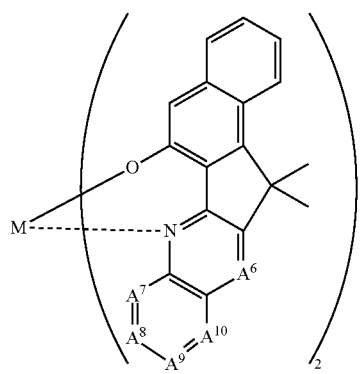
[2-40]
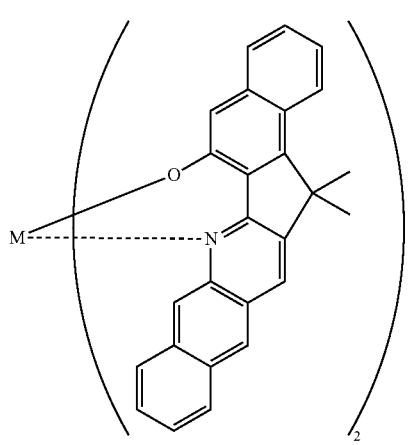
[2-41]
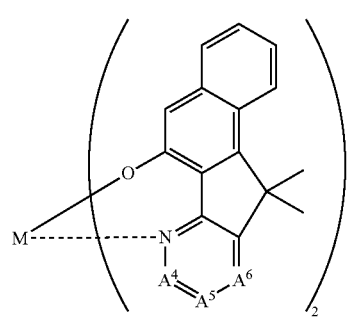
[2-42]
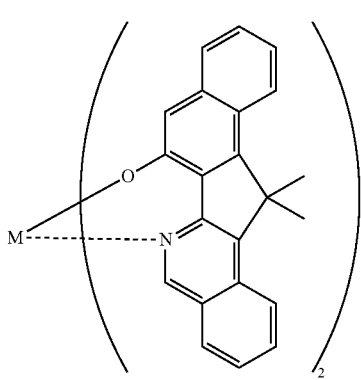

[2-43]
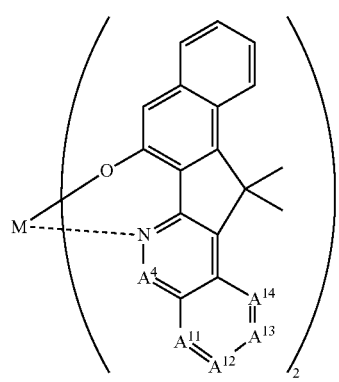
[2-44]
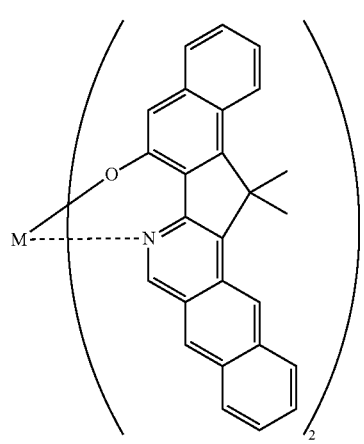
[2-45]
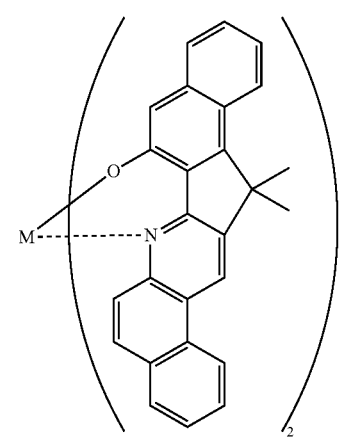
[2-46]
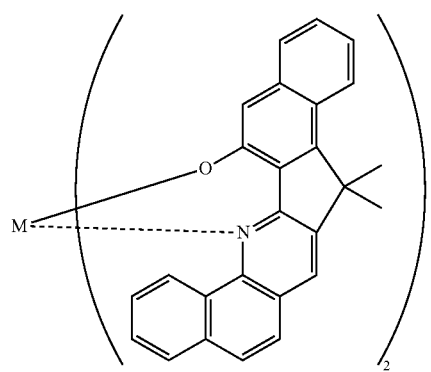
[2-47]
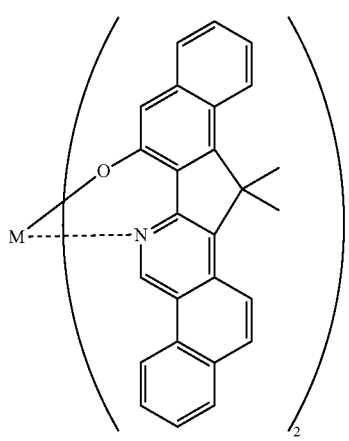
[2-48]
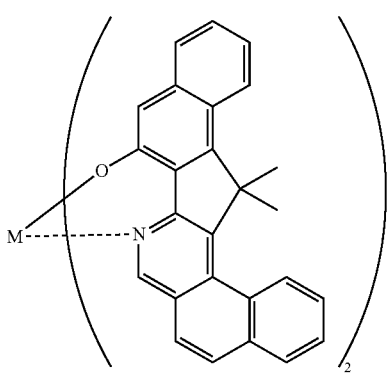
[2-49]
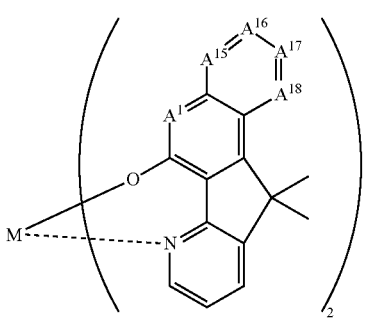
[2-50]
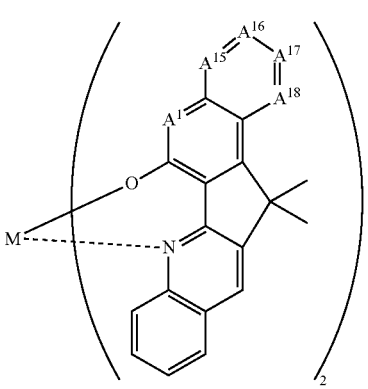

[2-51] 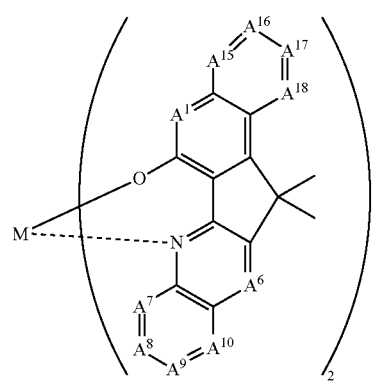
[2-52] 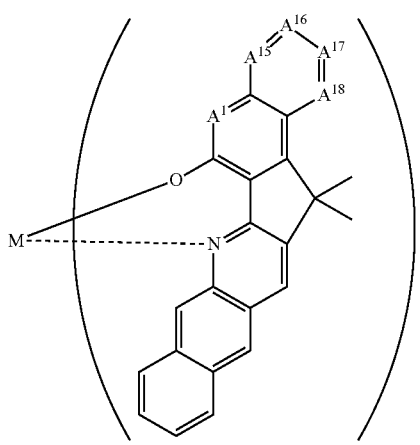
[2-53] 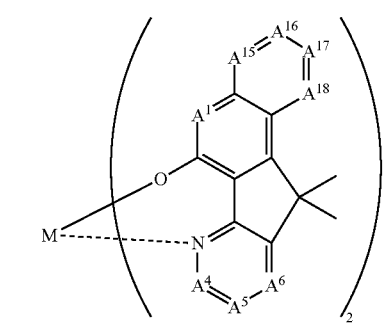
[2-54] 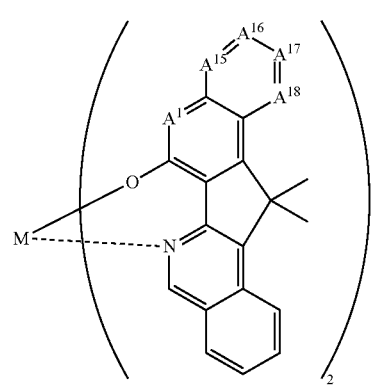
[2-55] 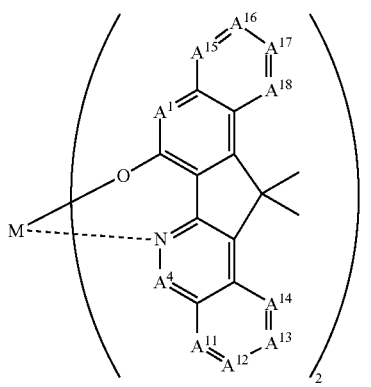
[2-56] 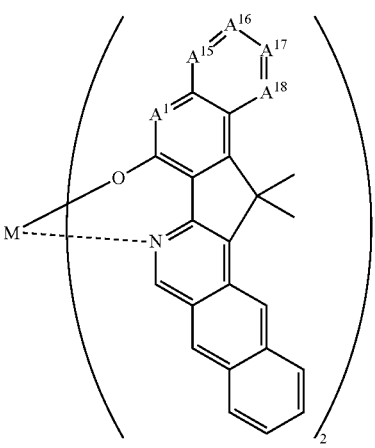
[2-57] 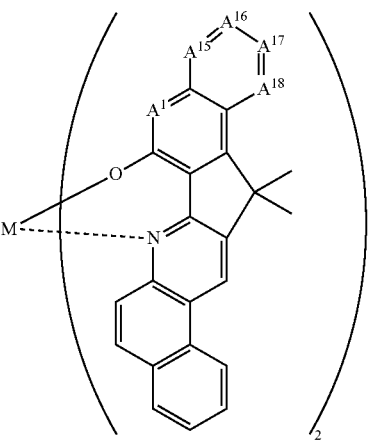
[2-58] 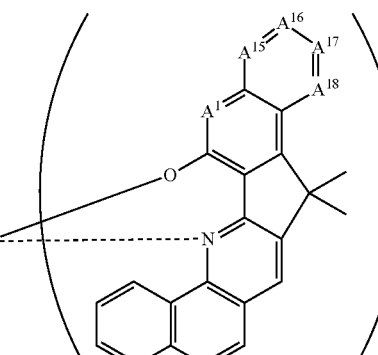

[2-59]
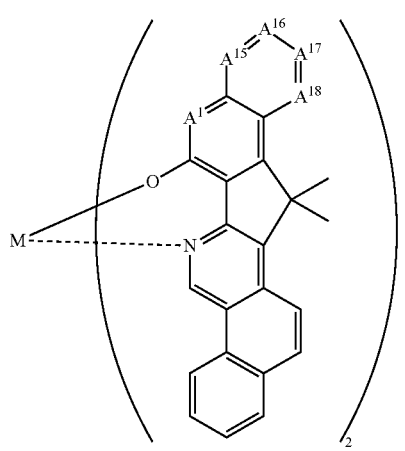
[2-60]
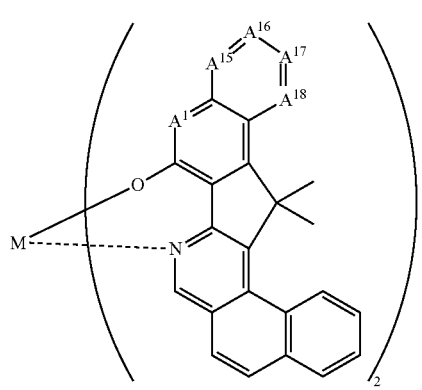
[2-61]
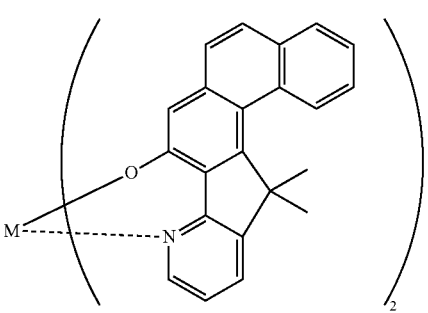
[2-62]
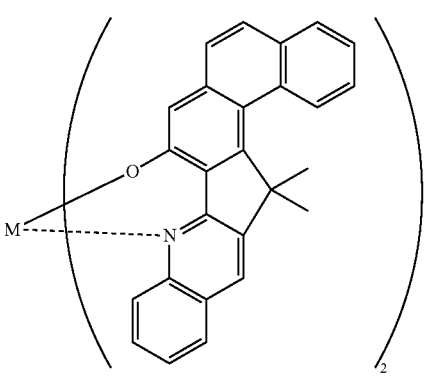
[2-63]
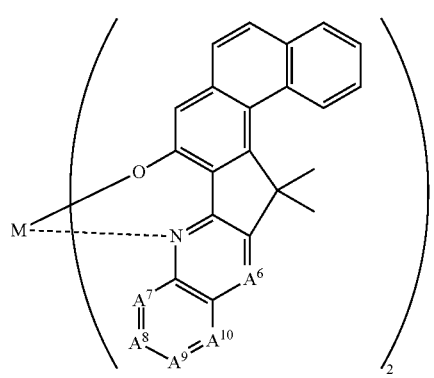
[2-64]
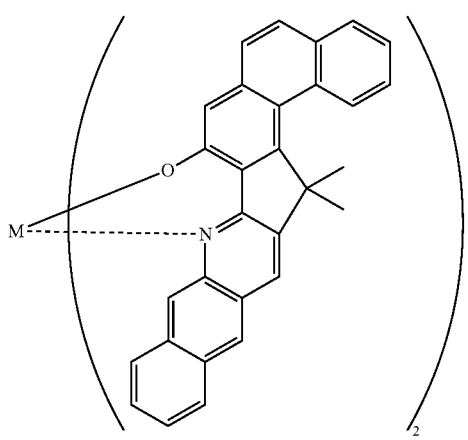
[2-65]
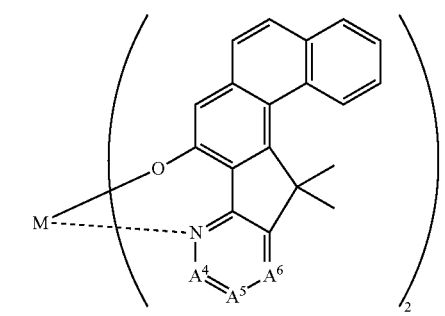
[2-66]
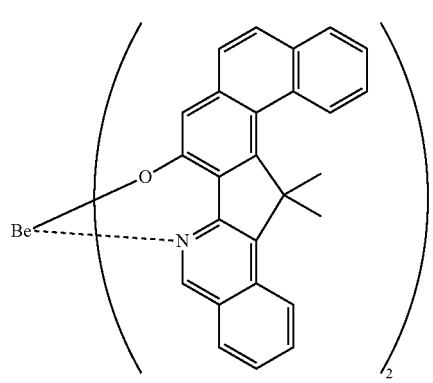

[2-67] 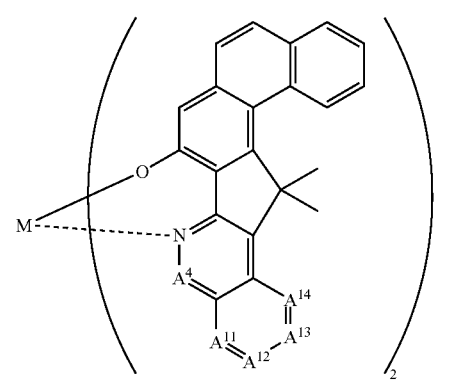
[2-68] 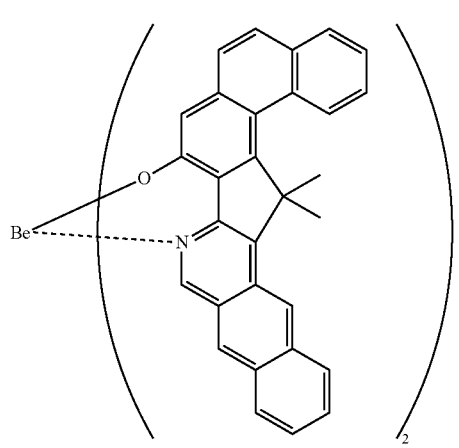
[2-69] 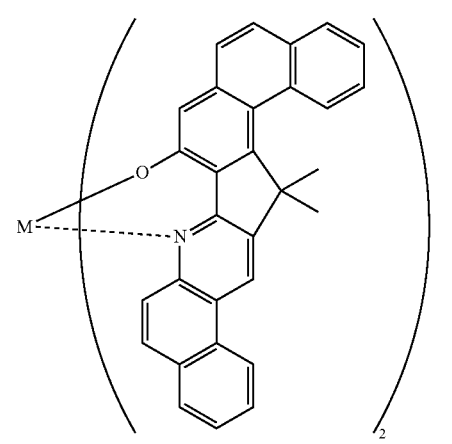
[2-70] 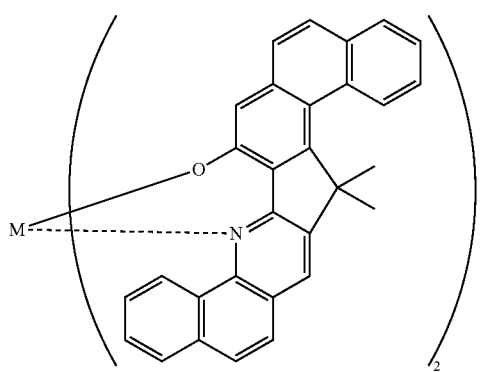
[2-71] 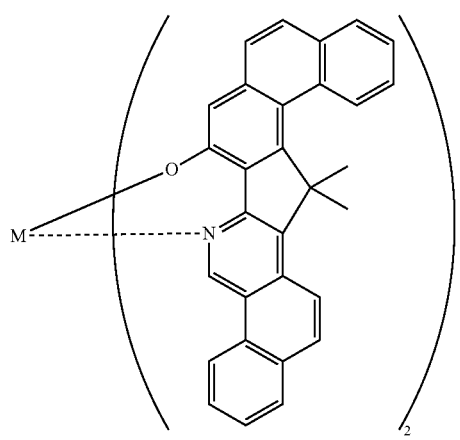
[2-72] 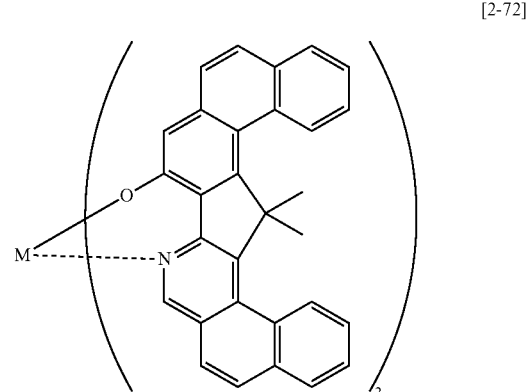
[2-73] 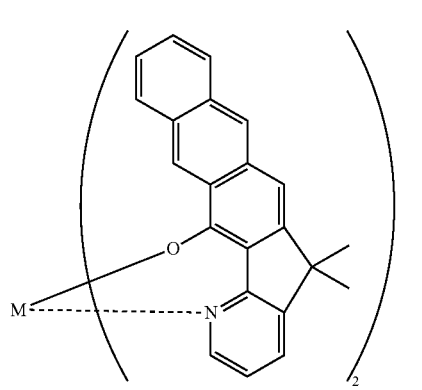
[2-74] 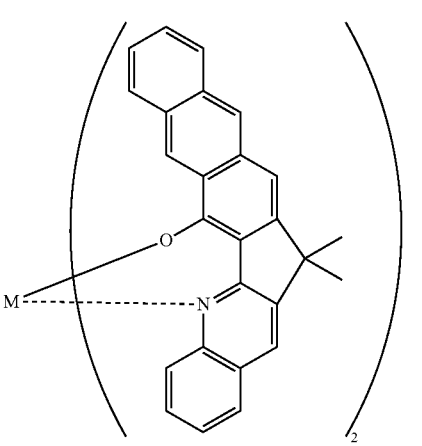

[2-75]
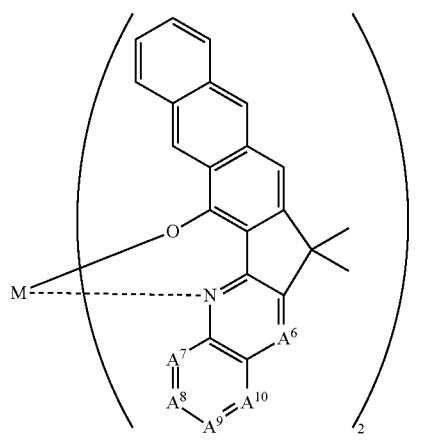
[2-76]
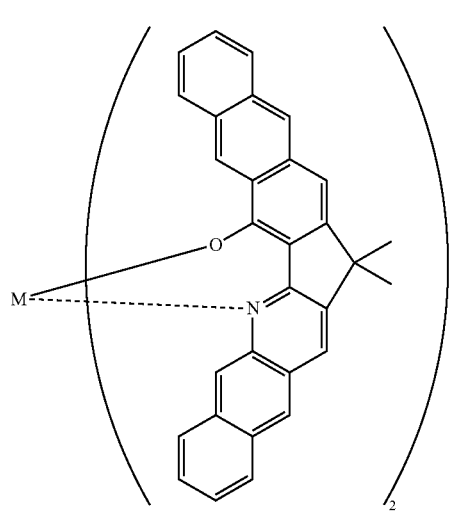
[2-77]
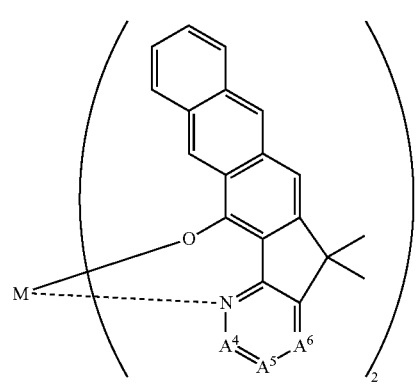
[2-78]
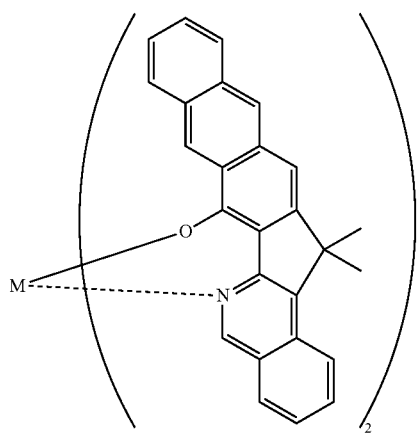
[2-79]
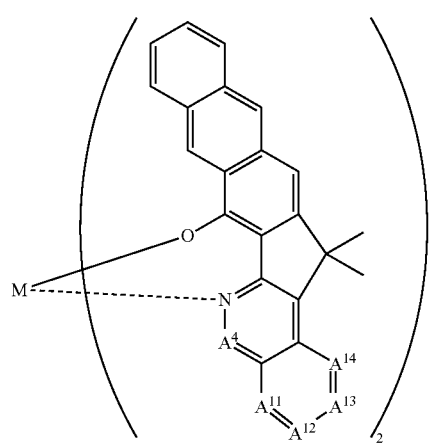
[2-80]
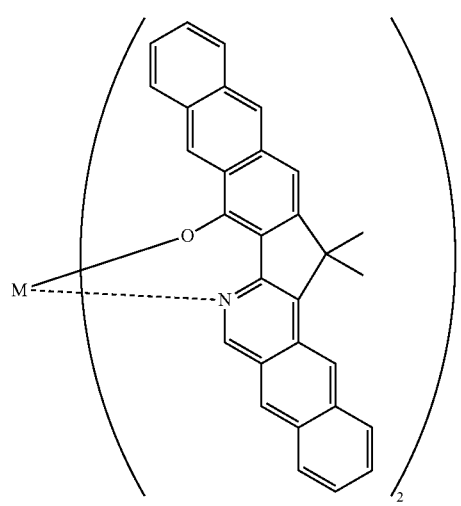

[2-81]
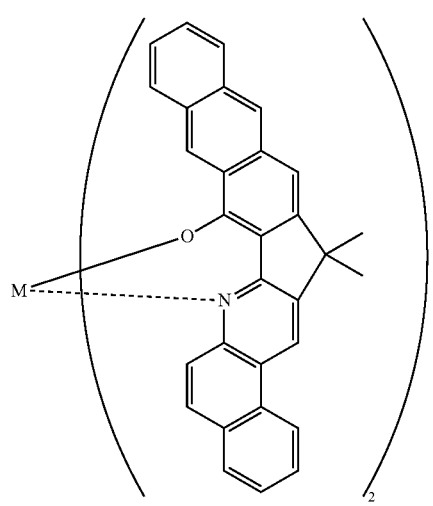
[2-82]
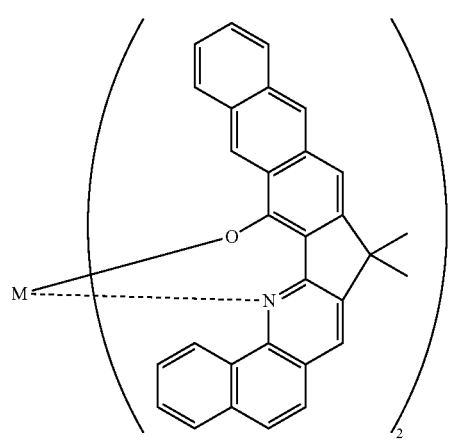
[2-83]
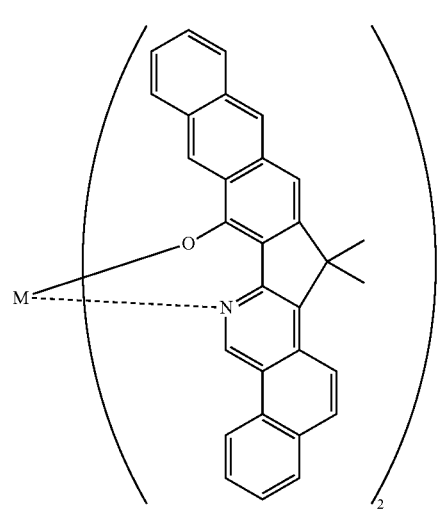
[2-84]
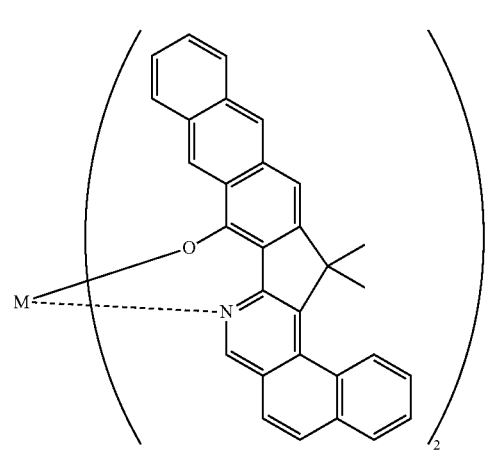
[2-85]
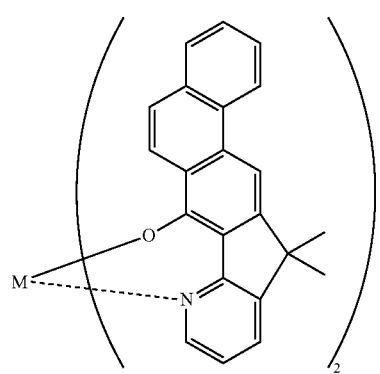
[2-86]
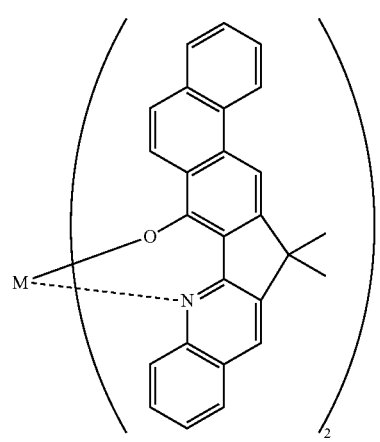

[2-87]
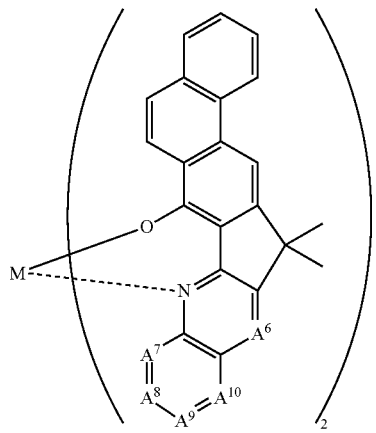
[2-88]
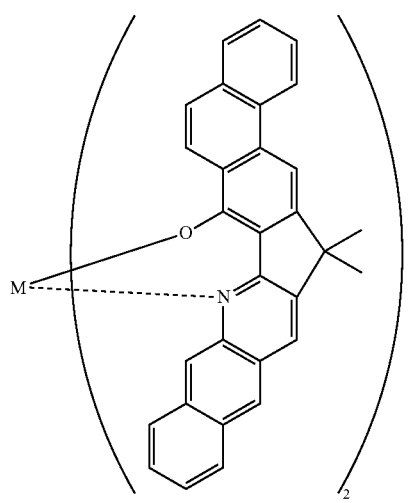
[2-89]
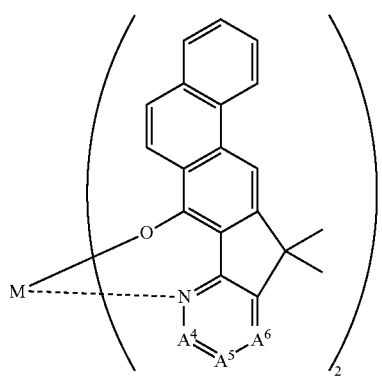
[2-90]
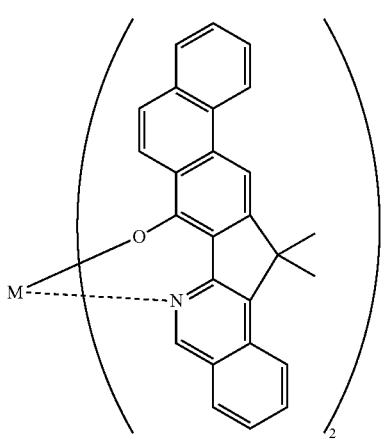
[2-91]
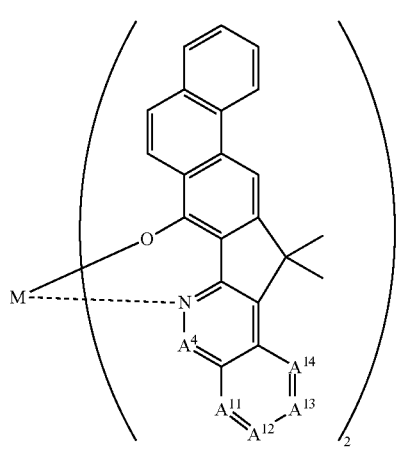
[2-92]
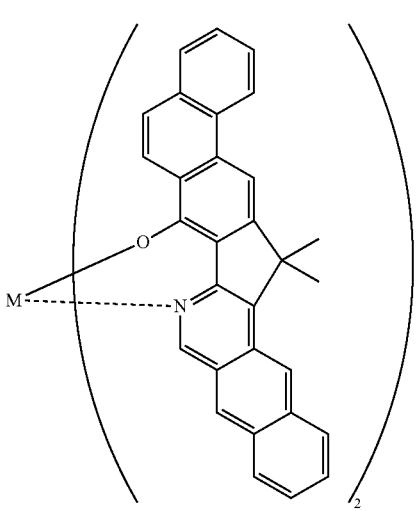

[2-93]
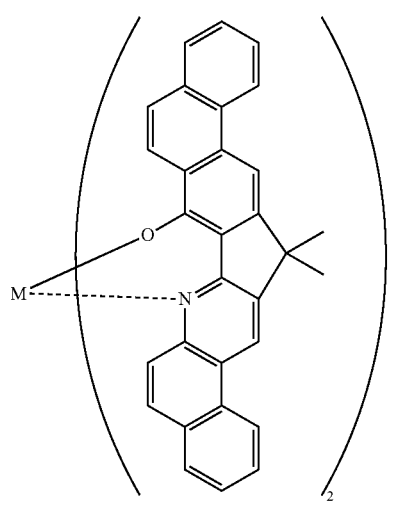
[2-94]
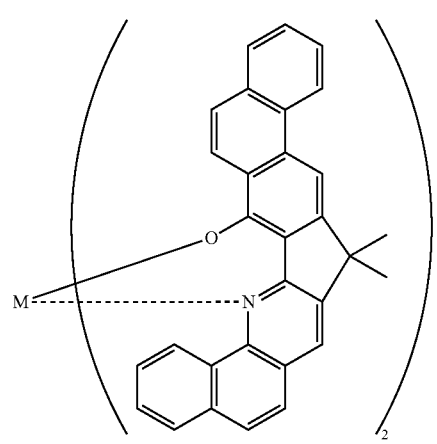
[2-95]
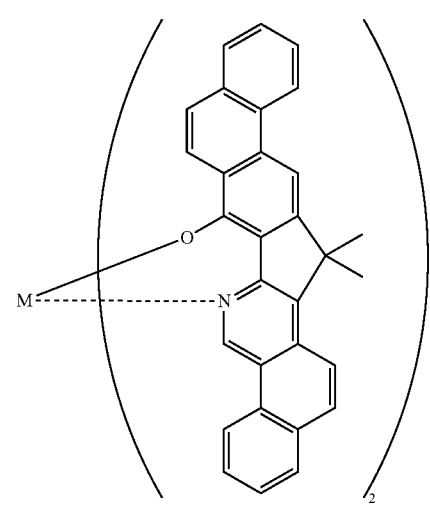
[2-96]
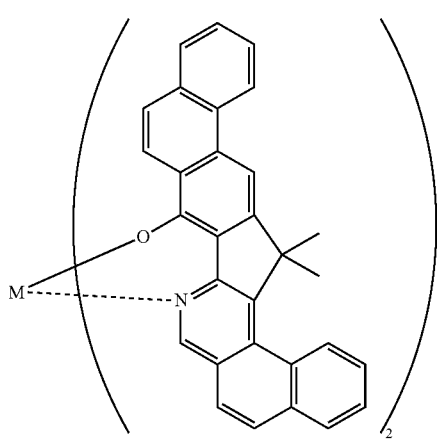
[2-97]
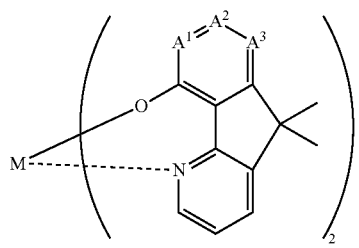
[2-98]
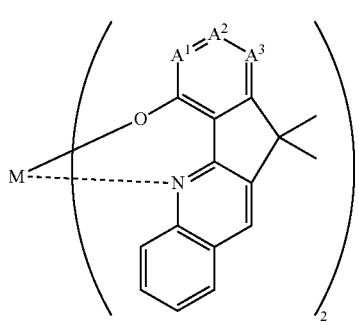
[2-99]
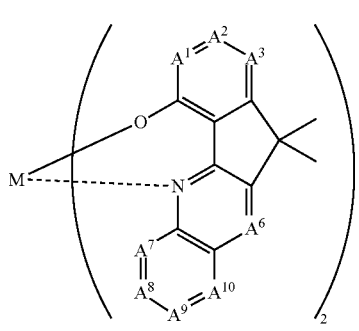

-continued
[2-100] 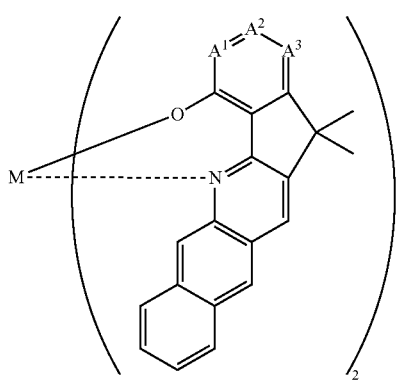
[2-101] 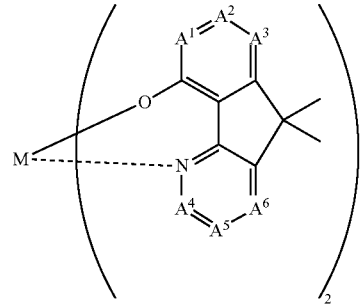
[2-102] 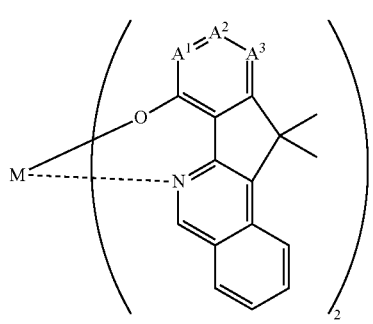
[2-103] 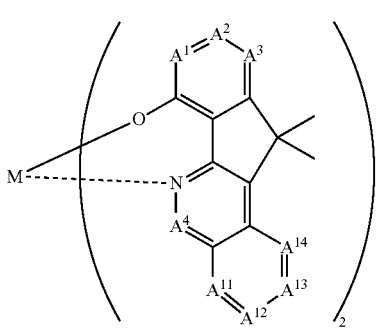
[2-104] 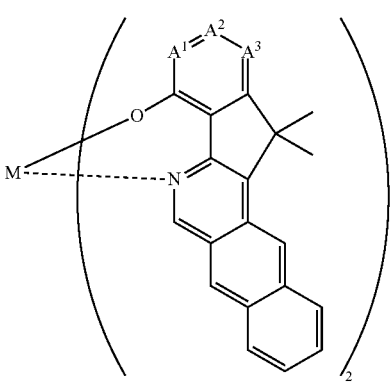
[2-105] 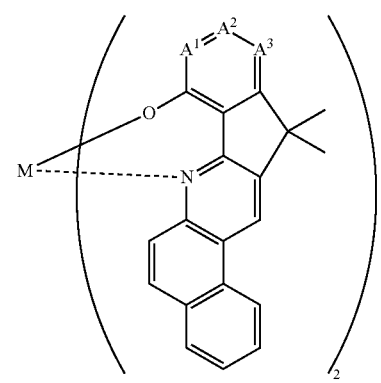
[2-106] 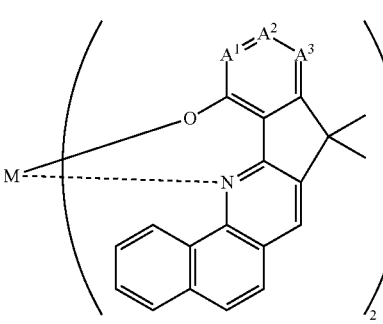
[2-107] 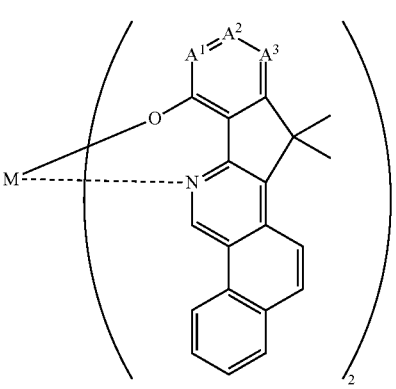

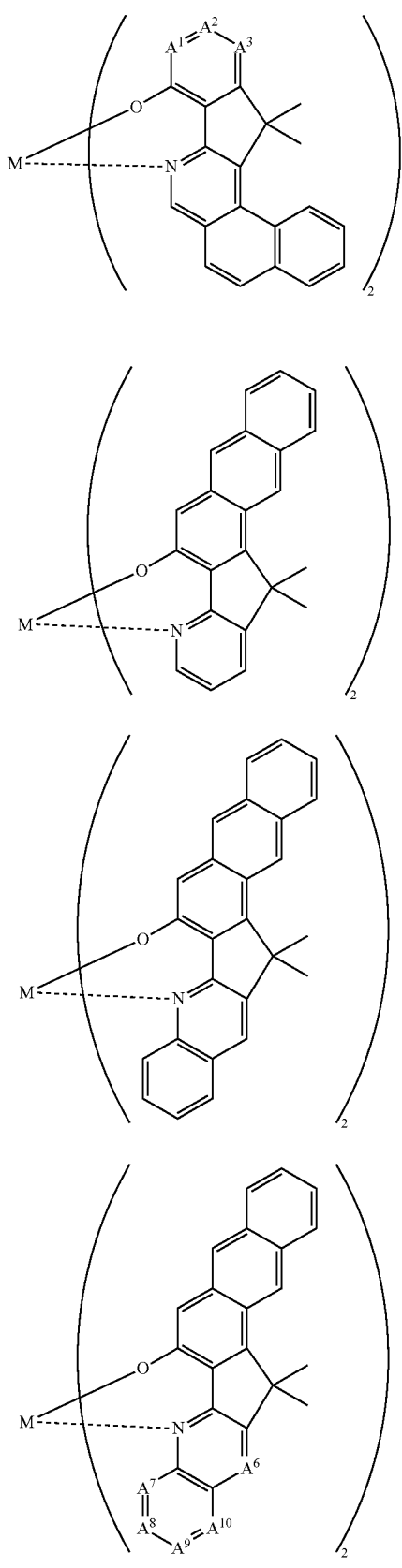
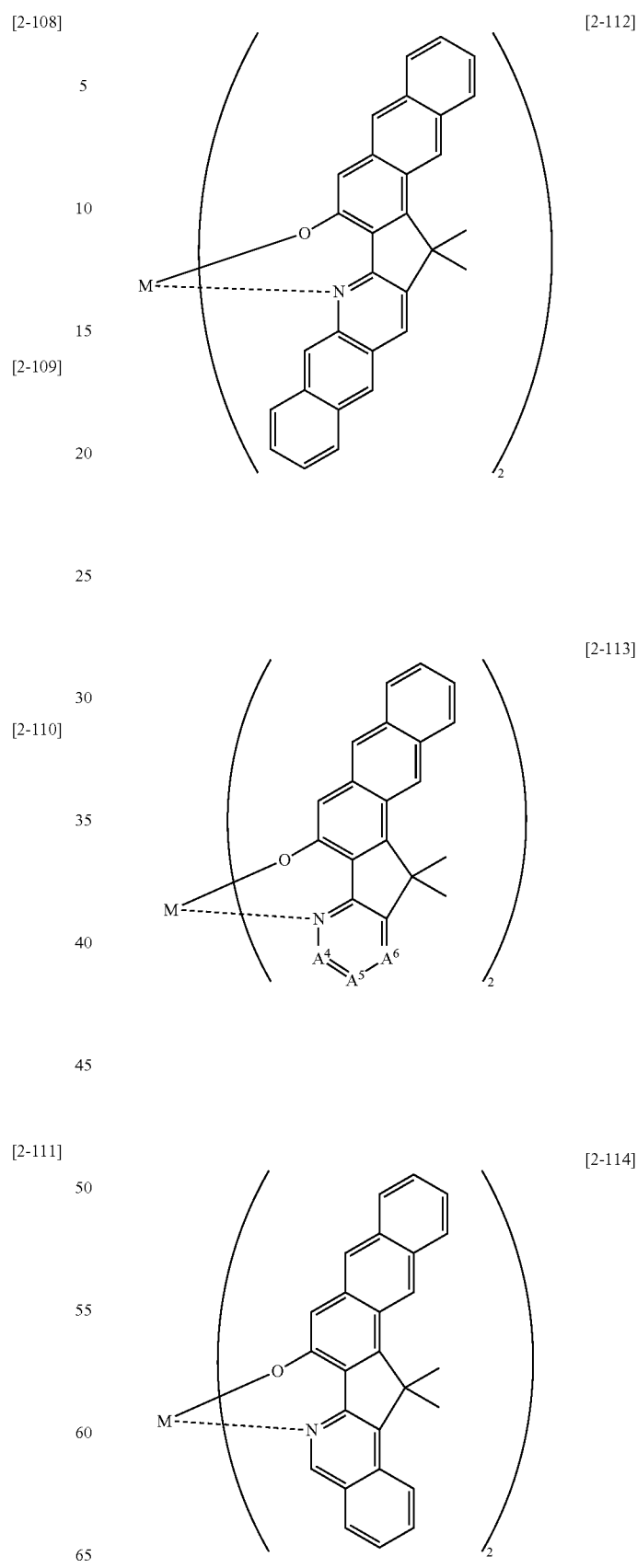

[2-115]
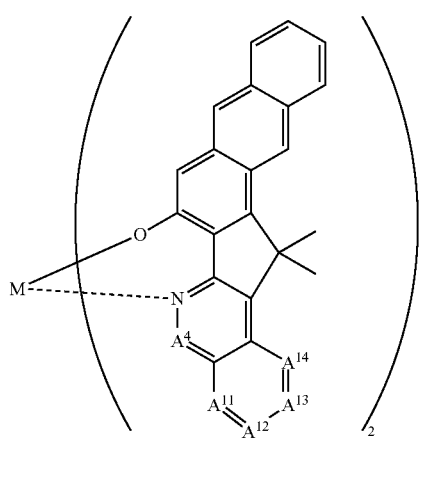
[2-118]
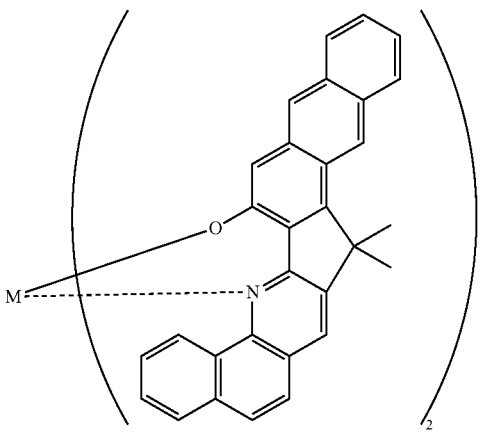
[2-116]
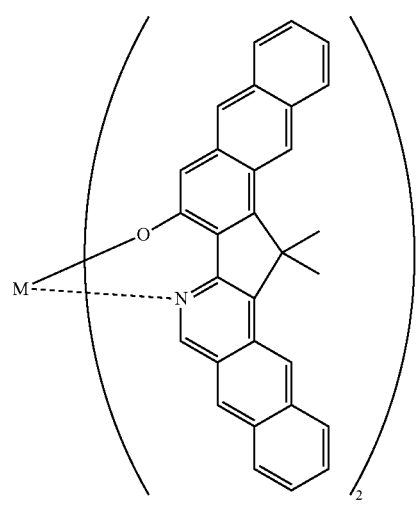
[2-119]
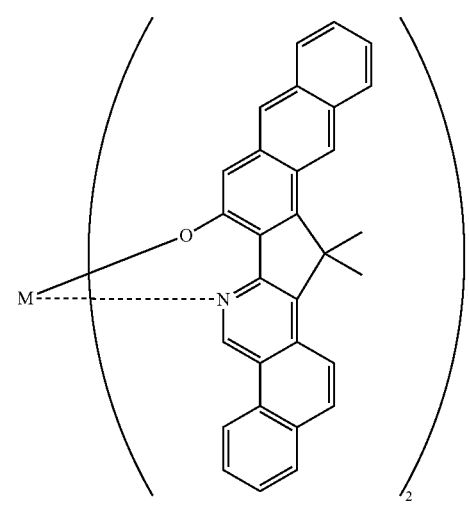
[2-117]
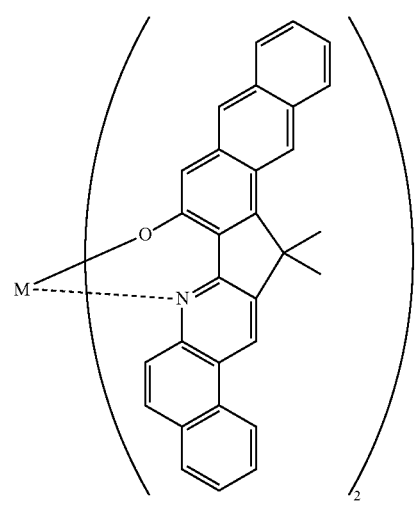
[2-220]
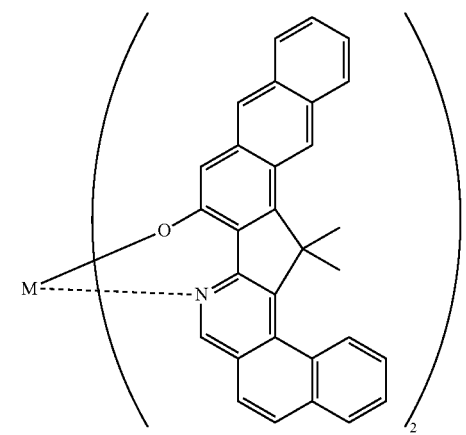

[2-121]
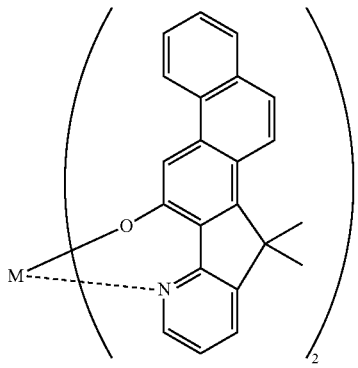
[2-122]
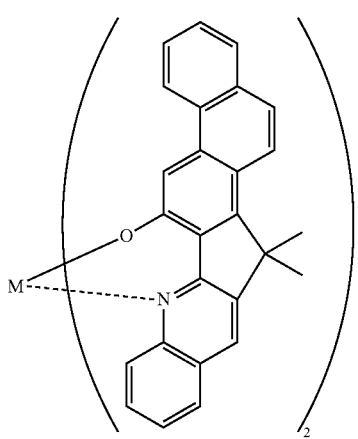
[2-123]
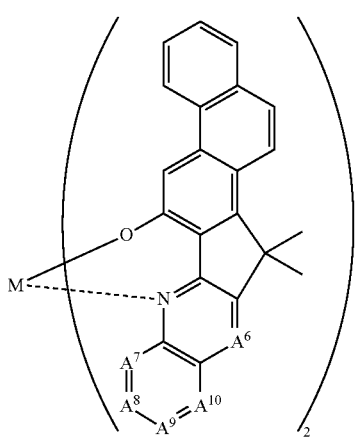
[2-124]
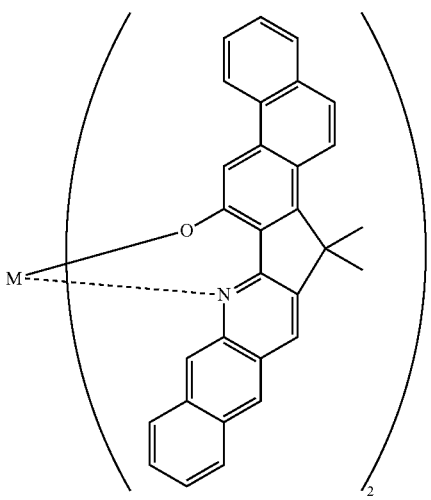
[2-125]
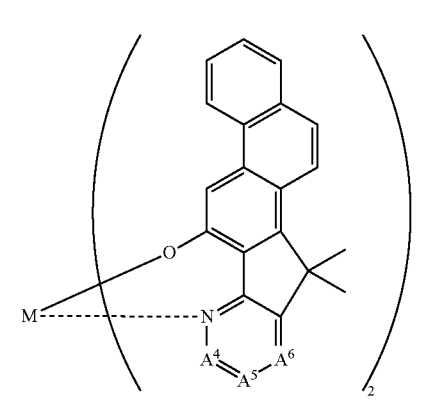
[2-126]
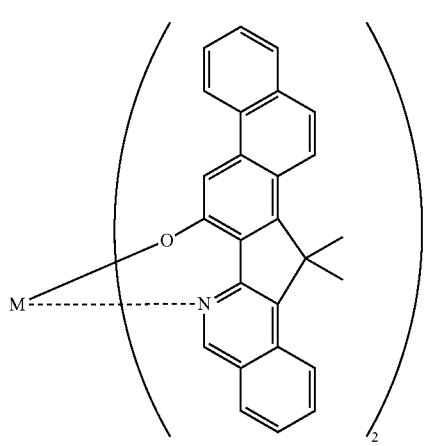

[2-127] 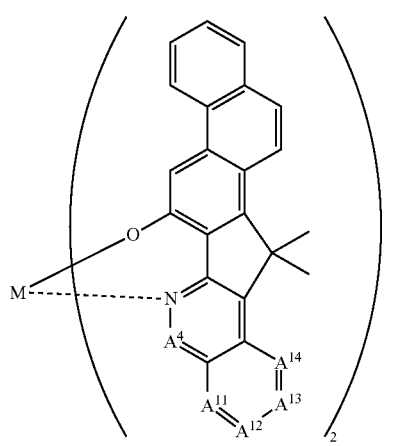
[2-128] 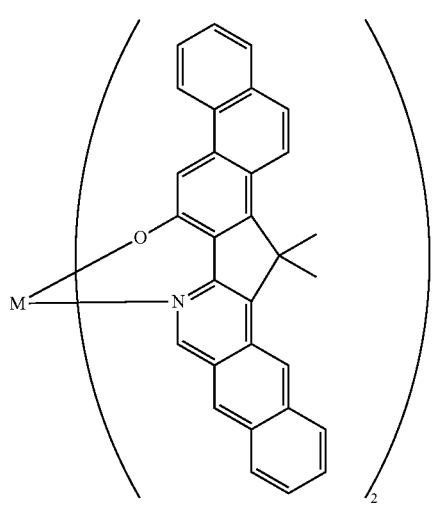
[2-129] 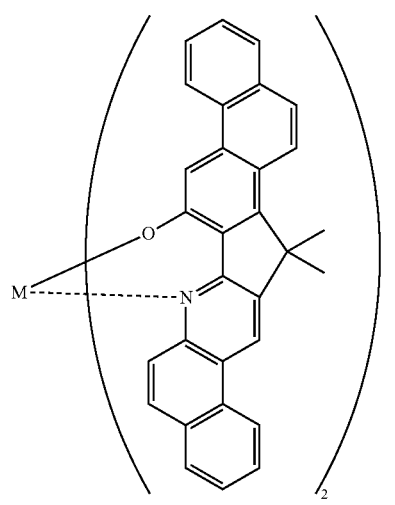
[2-130] 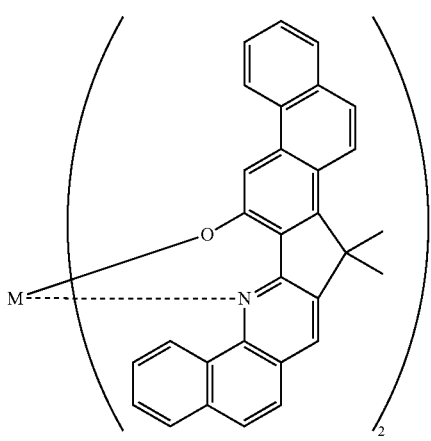
[2-131] 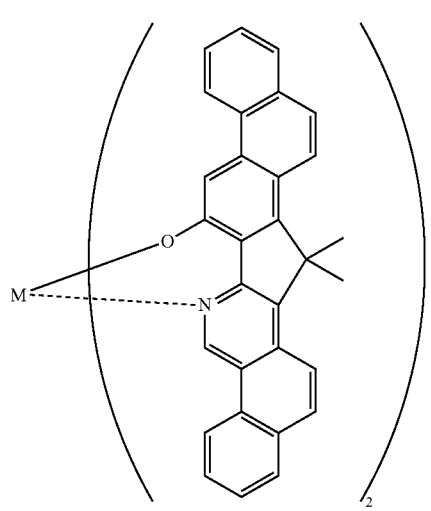
[2-132] 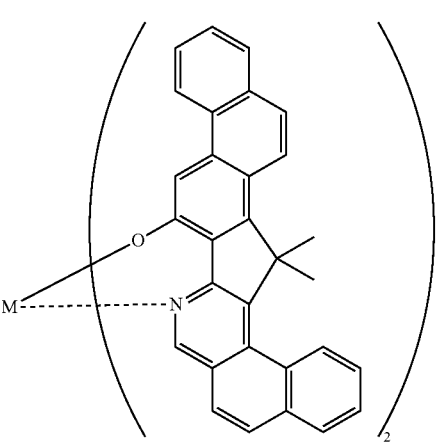
[2-133] 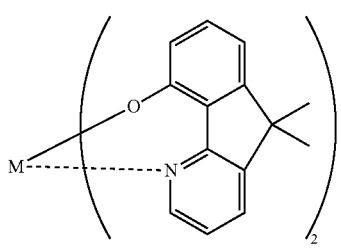

[2-134] 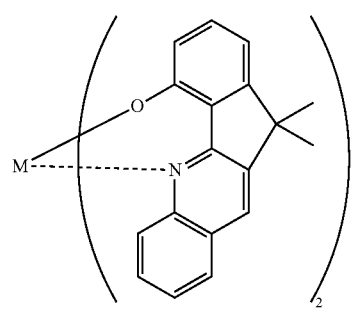
[2-135] 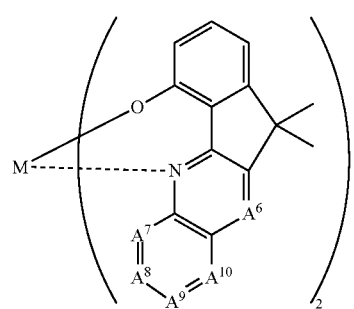
[2-136] 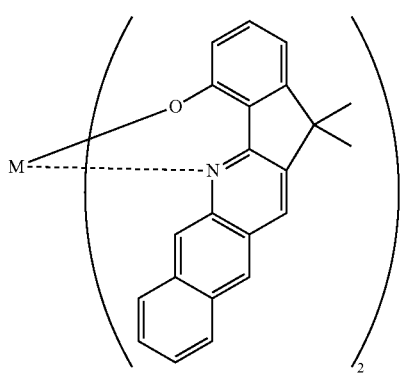
[2-137] 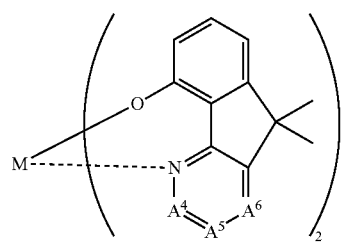
[2-138] 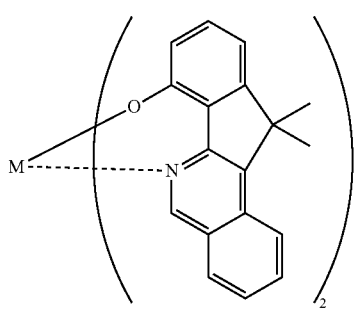
[2-139] 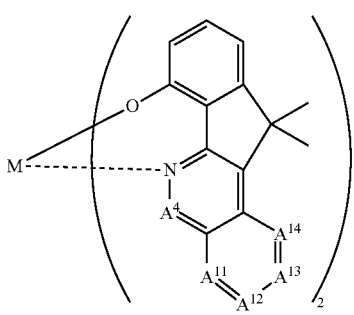
[2-140] 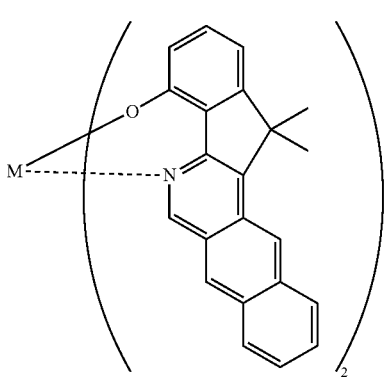
[2-141] 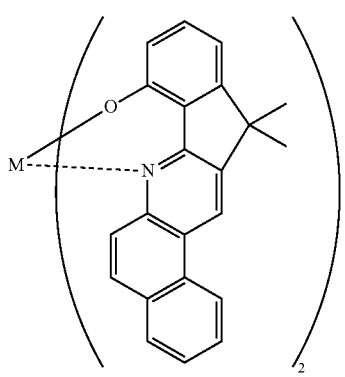
[2-142] 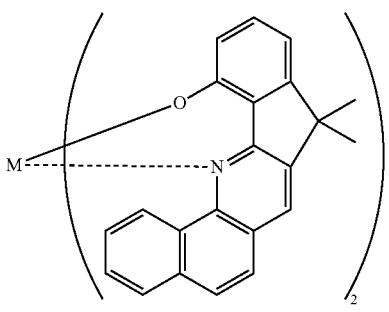

[2-143]
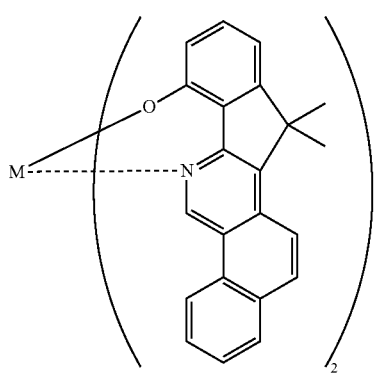

[2-144]
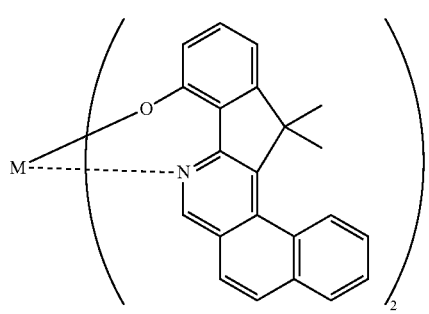

[2-145]
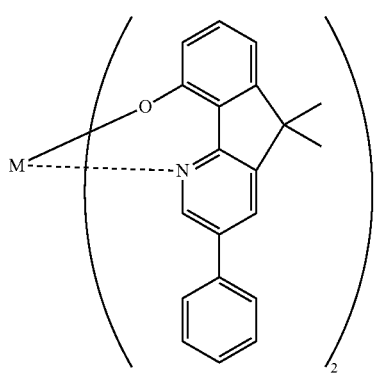

[2-146]
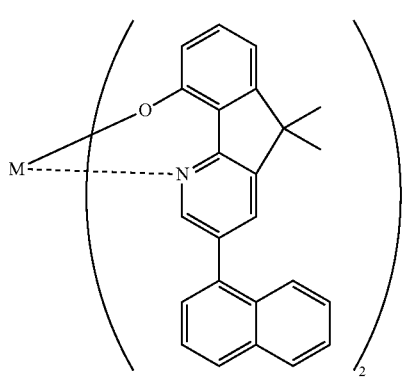

[2-147]
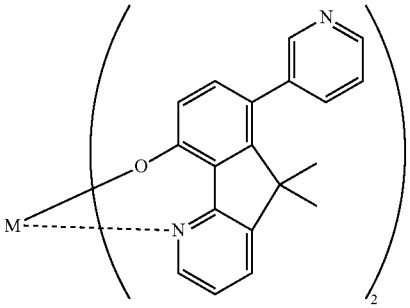

In Chemical Formulae 2-1 to 2-147, A1 to A18 are the same or different, and are a carbon atom or a nitrogen atom, provided that at least one of A1 to A18 is a nitrogen atom, and M is Be or Zn.

According to another aspect of this disclosure, an organic light emitting device is provided, which includes a first electrode, a second electrode facing the first electrode, and an organic layer interposed between the first electrode and the second electrode, wherein the organic layer includes a metal complex compound represented by the above Chemical Formula 1.

The organic layer may include at least one among a hole injection layer, a hole transport layer, an emission layer, an electron transport layer, and an electron injection layer that are sequentially positioned on the first electrode. The metal complex compound may be included in the emission layer or the electron transport layer.

Further aspects of this disclosure are described in more detail.

This disclosure may increase luminous efficiency of an organic light emitting device, while reducing its driving voltage.

BRIEF DESCRIPTION OF THE DRAWINGS

FIG. 1 is the schematic cross-sectional view of an organic light emitting diode device according to one aspect of the present disclosure.

DETAILED DESCRIPTION OF THE PREFERRED EMBODIMENT

The present disclosure will be described more fully hereinafter with reference to the accompanying drawings, in which example embodiments of this disclosure are shown. This disclosure may, however, be embodied in many different forms and is not construed as limited to the example embodiments set forth herein.

In the drawings, the thickness of layers, films, panels, regions, etc., are exaggerated for clarity. Like reference numerals designate like elements throughout the specification. It will be understood that when an element such as a layer, film, region, or substrate is referred to as being "on" another element, it can be directly on the other element or intervening elements may also be present. In contrast, when an element is referred to as being "directly on" another element, there are no intervening elements present.

As used herein, when a definition is not otherwise provided, the term "substituted" refers to one substituted with a halogen, a hydroxy group, a C1 to C20 alkyl group, a C2 to C20 alkenyl group, a C2 to C20 alkynyl group, a C1 to C20 alkoxy group, a C3 to C30 cycloalkyl group, a C3 to C30 cycloalkenyl group, a C3 to C30 cycloalkynyl group, a C2 to C30 heterocycloalkyl group, a C2 to C30 heterocycloalkenyl group, a C2 to C30 heterocycloalkynyl group, a C6 to C30 aryl group, a C6 to C30 aryloxy group, a C3 to C30 heteroaryl group, an amine group, an ester group, a carboxyl group, a nitro group, or a cyano group, instead of at least one hydrogen atom.

As used herein, when a definition is not otherwise provided, the term "heterocycloalkyl group", "heterocycloalkenyl group", "heterocycloalkynyl group", and "heteroaryl group" respectively refer to a heterocycloalkyl group, a heterocycloalkenyl group, a heterocycloalkynyl group, and a heteroaryl group including at least one of N, O, S, and P in a cycle of a cycloalkyl group, a cycloalkenyl group, a cycloalkynyl group, and an aryl group.

The metal complex compound according to one embodiment may be represented by the following Chemical Formula 1.

CHEMICAL FORMULA 1

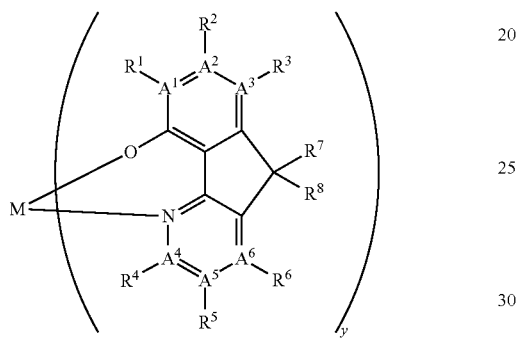

In Chemical Formula 1, M is a Group 2 metal ion or Group 3 metal ion, R1 to R8 are the same or different, and are hydrogen, a halogen, a hydroxy group, a substituted or unsubstituted C1 to C20 alkyl group, a substituted or unsubstituted C2 to C20 alkenyl group, a substituted or unsubstituted C2 to C20 alkynyl group, a substituted or unsubstituted C1 to C20 alkoxy group, a substituted or unsubstituted C3 to C30 cycloalkyl group, a substituted or unsubstituted C3 to C30 cycloalkenyl group, a substituted or unsubstituted C3 to C30 cycloalkynyl group, a substituted or unsubstituted C2 to C30 heterocycloalkyl group, a substituted or unsubstituted C2 to C30 heterocycloalkenyl group, a substituted or unsubstituted C2 to C30 heterocycloalkynyl group, a substituted or unsubstituted C6 to C30 aryl group, a substituted or unsubstituted C6 to C30 aryloxy group, a substituted or unsubstituted C3 to C30 heteroaryl group, an amine group, an ester group, a carboxyl group, a nitro group, or a cyano group, optionally, R1 and R2, R2 and R3, R4 and R5, and R5 and R6 may be respectively bound to each other to form a substituted or unsubstituted C6 to C30 aryl group, a substituted or unsubstituted C6 to C30 aryloxy group, or a substituted or unsubstituted C3 to C30 heteroaryl group, A1 to A6 are the same or different, and are a carbon atom or a nitrogen atom, and y is 2 or 3.

In Chemical Formula 1, R1 to R8 are the same or different, and are hydrogen, a halogen, a substituted or unsubstituted C1 to C20 alkyl group, a substituted or unsubstituted C6 to C30 aryl group, a substituted or unsubstituted C6 to C30 aryloxy group, a substituted or unsubstituted C3 to C30 heteroaryl group, an amine group, an ester group, a nitro group, or a cyano group. Optionally, R1 and R2, R2 and R3, R4 and R5, and R5 and R6 are respectively bound to each other to form a substituted or unsubstituted C6 to C30 aryl group, a substituted or unsubstituted C6 to C30 aryloxy group, or a substituted or unsubstituted C3 to C30 heteroaryl group.

In Chemical Formula 1, M may be Be, Zn, Mg, Ca, Y, B, Al, Ga, In, or a combination thereof.

Examples of the metal complex compound may include one of the following Chemical Formulae 2-1 to 2-147, but are not limited thereto.

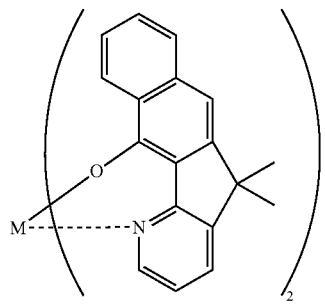
[2-1]

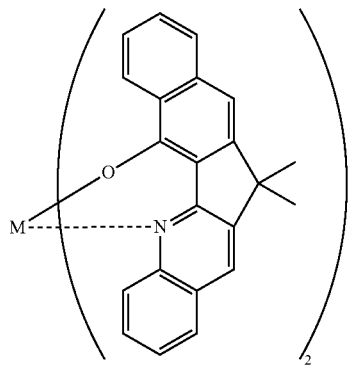
[2-2]

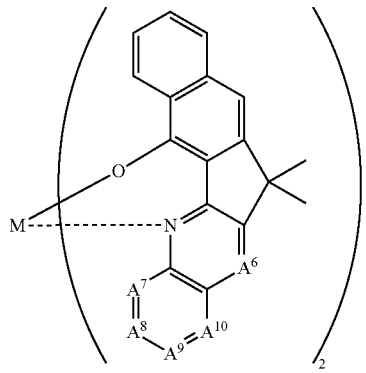
[2-3]

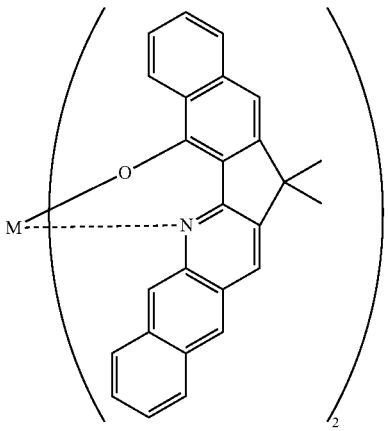
[2-4]

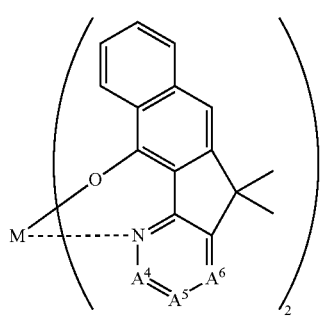
(2-5)
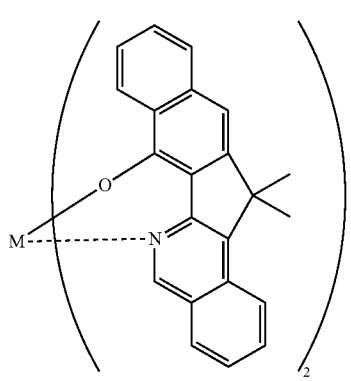
[2-6]
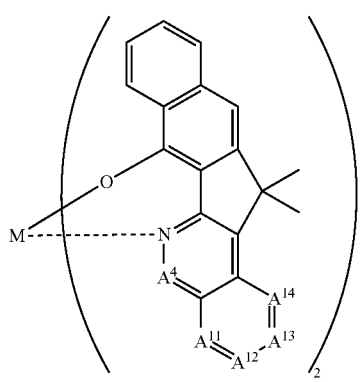
[2-7]
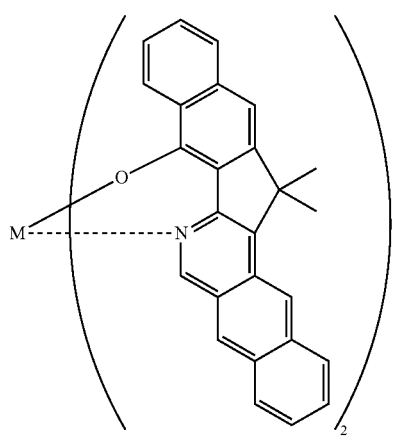
[2-8]
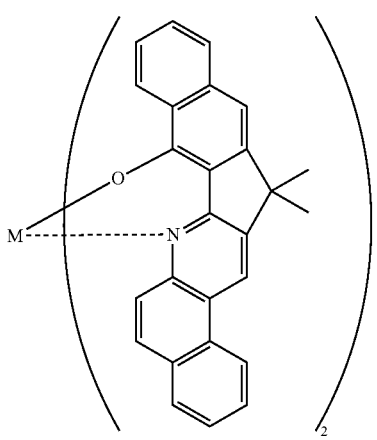
[2-9]
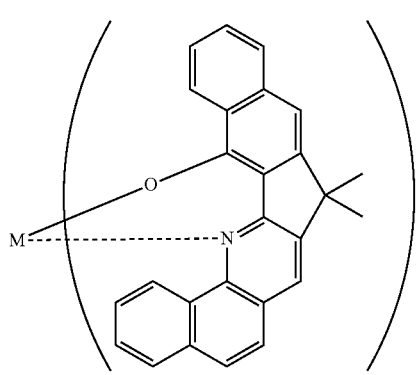
[2-10]
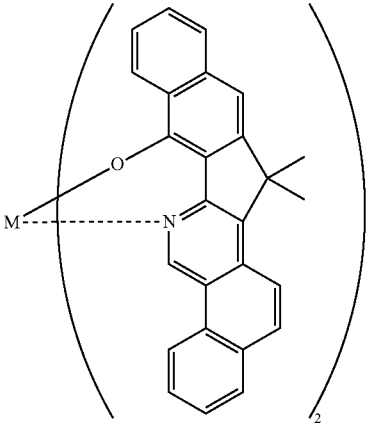
[2-11]
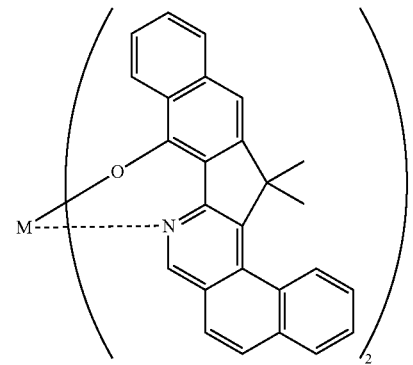
[2-12]

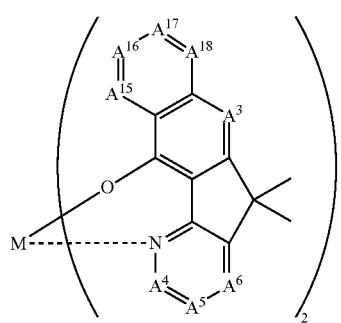
[2-13]
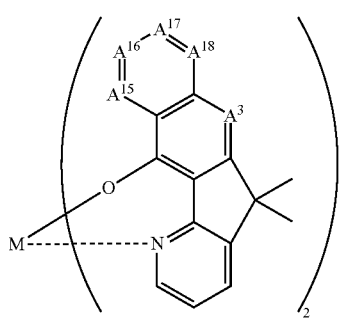
[2-14]
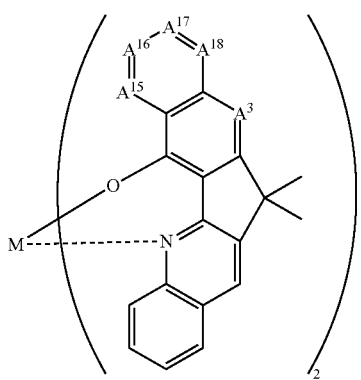
[2-15]
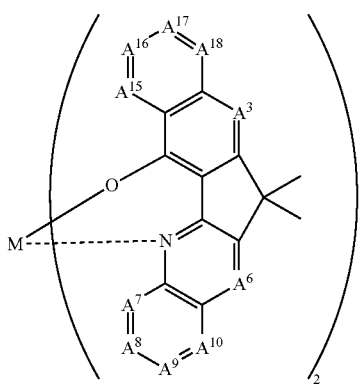
[2-16]
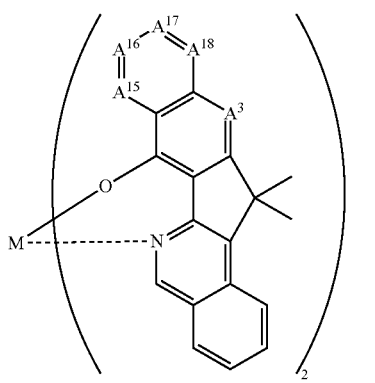
[2-17]
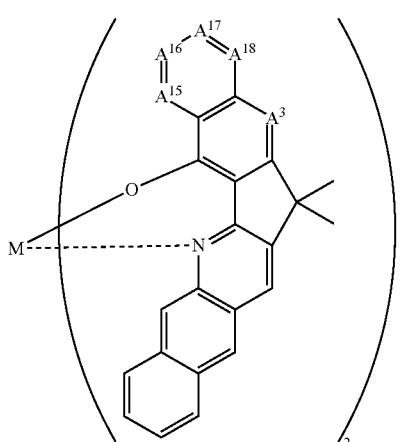
[2-18]
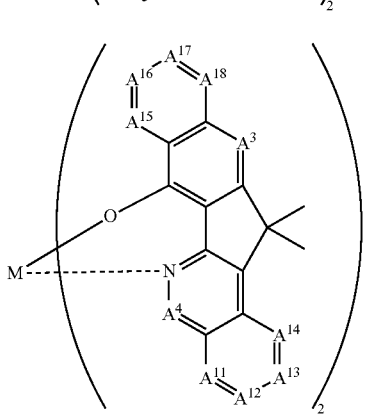
[2-19]
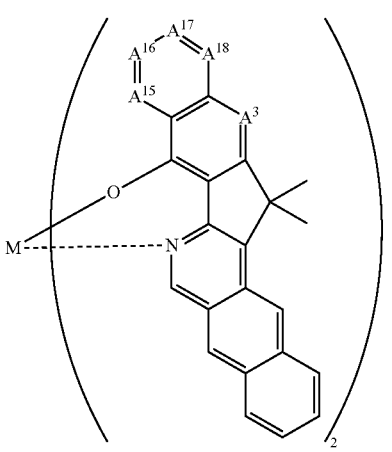
[2-20]

[2-21]
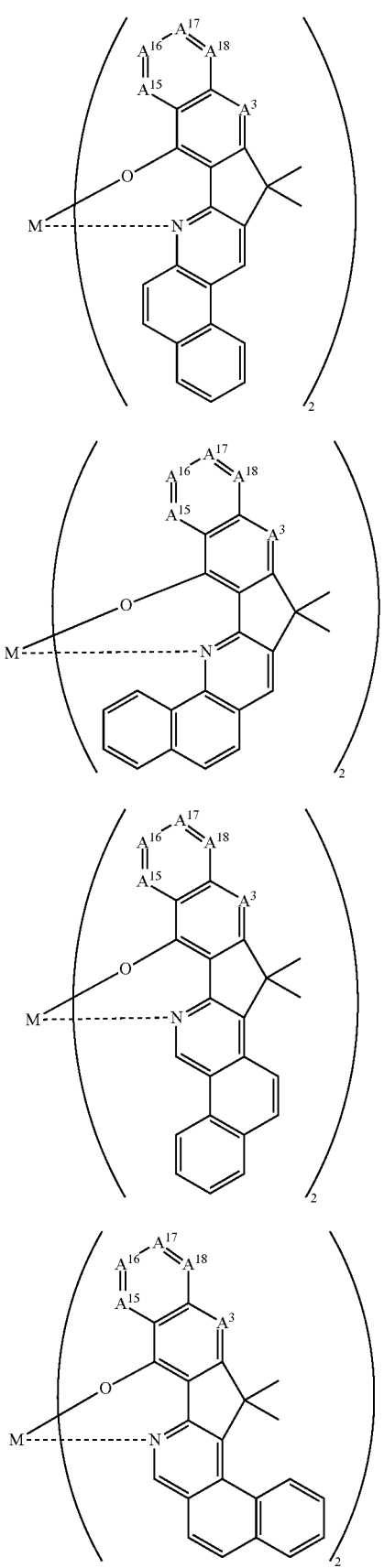
[2-22]
[2-23]
[2-24]
[2-25]
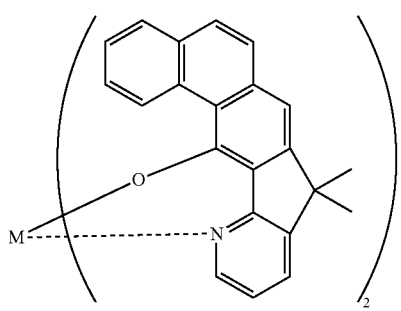
[2-26]
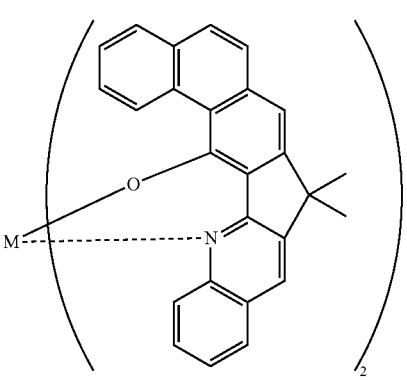
[2-27]
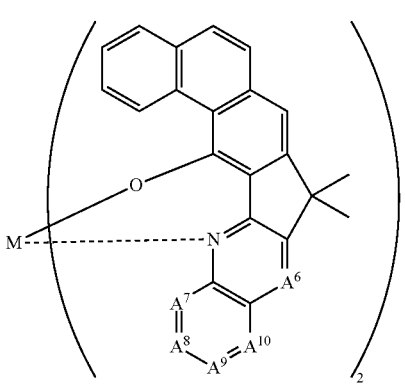
[2-28]
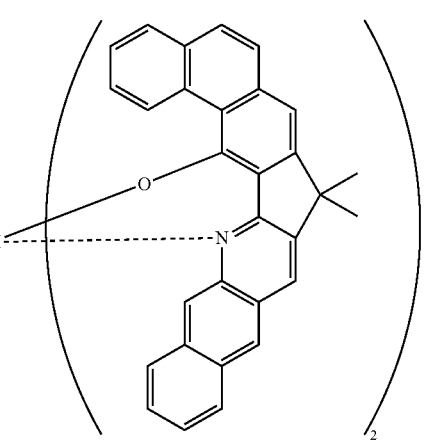

[2-29]
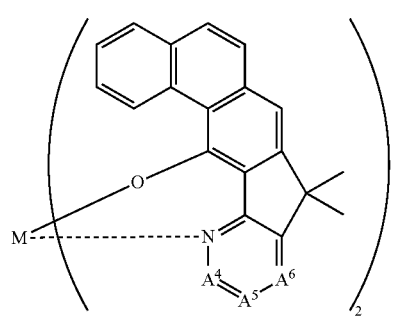
[2-30]
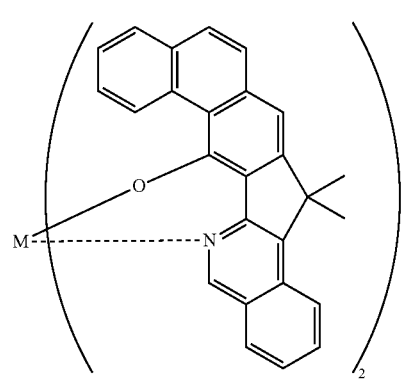
[2-31]
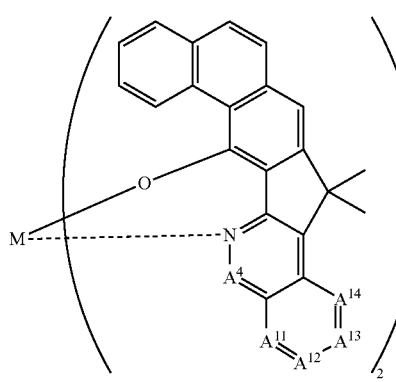
[2-32]
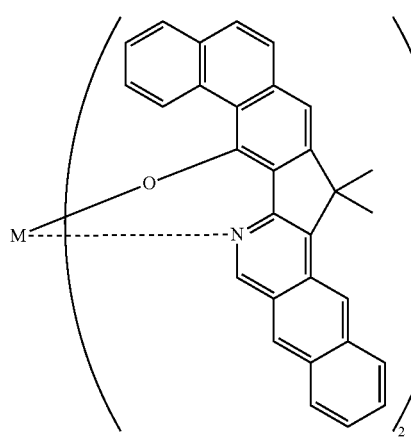
[2-33]
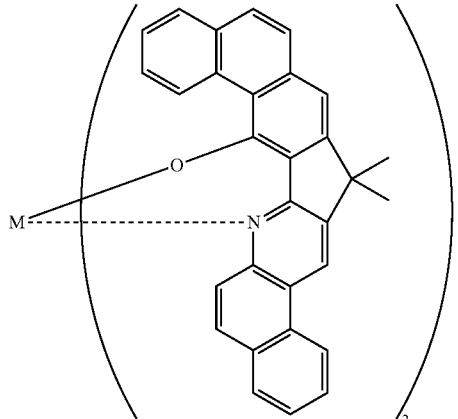
[2-34]
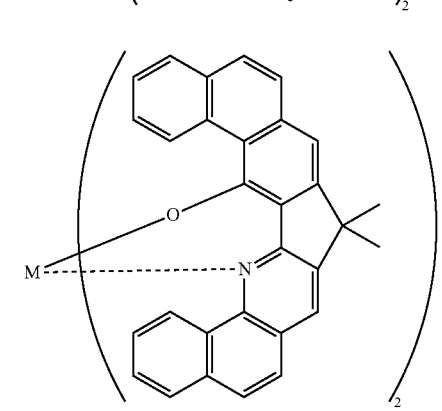
[2-35]
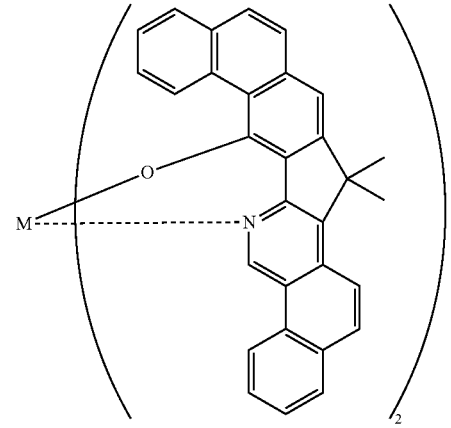
[2-36]
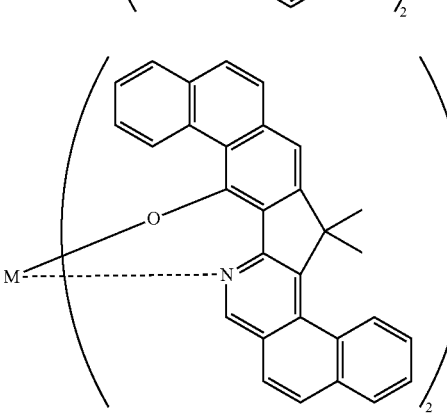

-continued
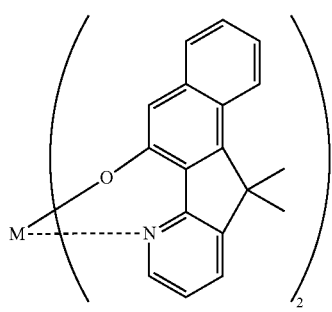 [2-37]
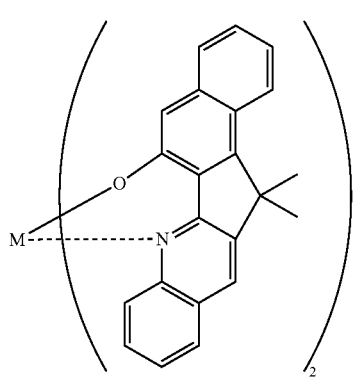 [2-38]
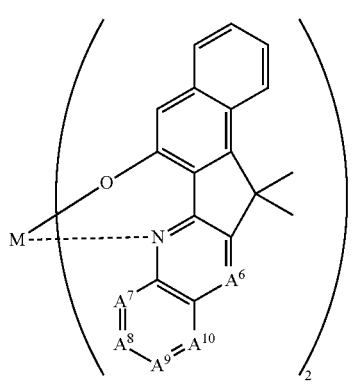 [2-39]
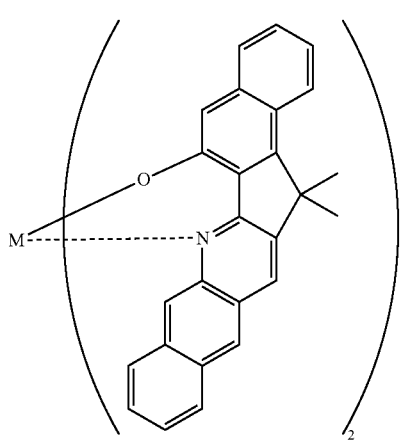 [2-40]
-continued
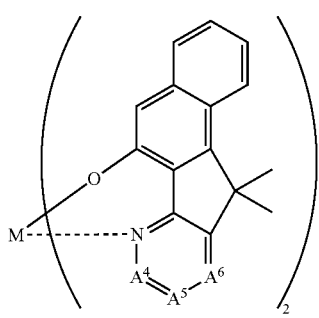 [2-41]
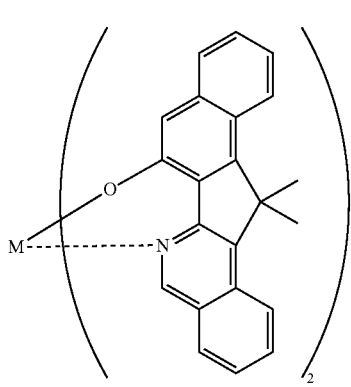 [2-42]
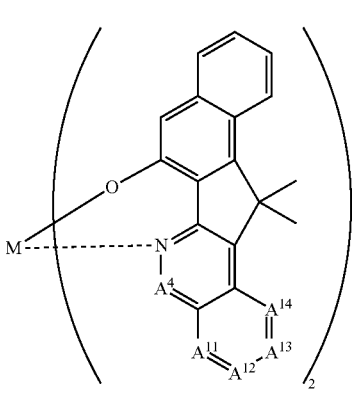 [2-43]
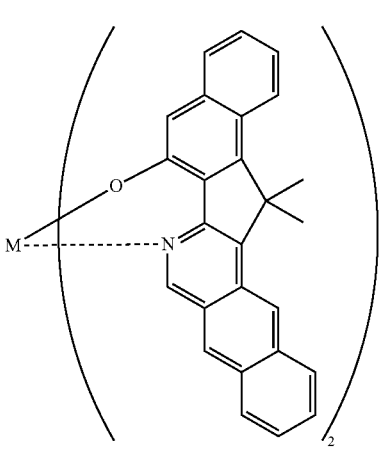 [2-44]

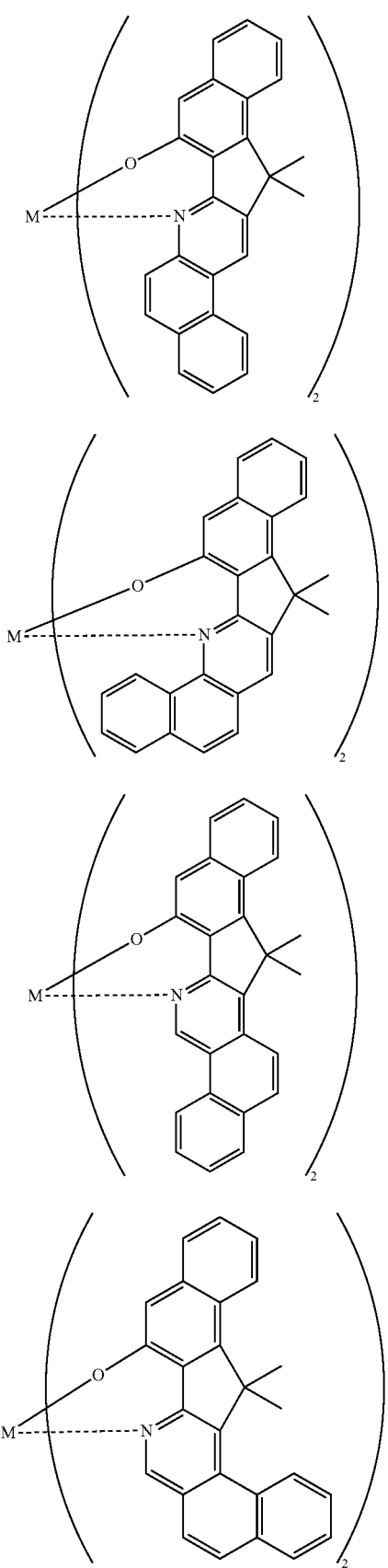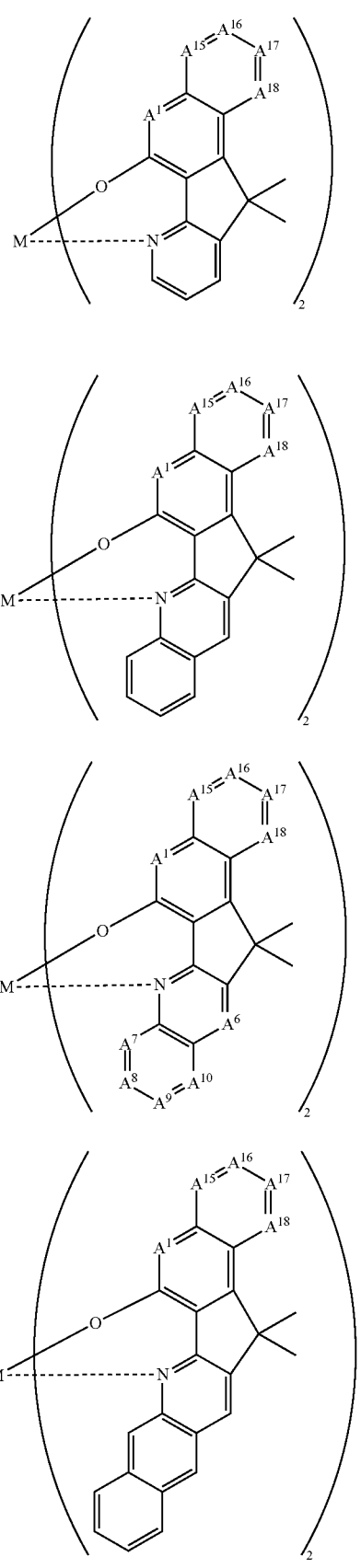

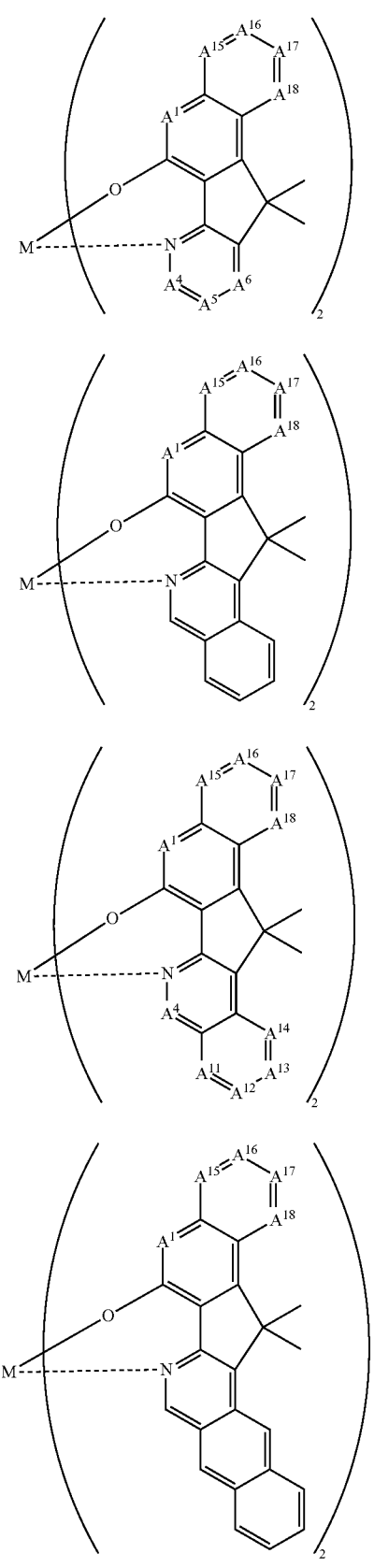
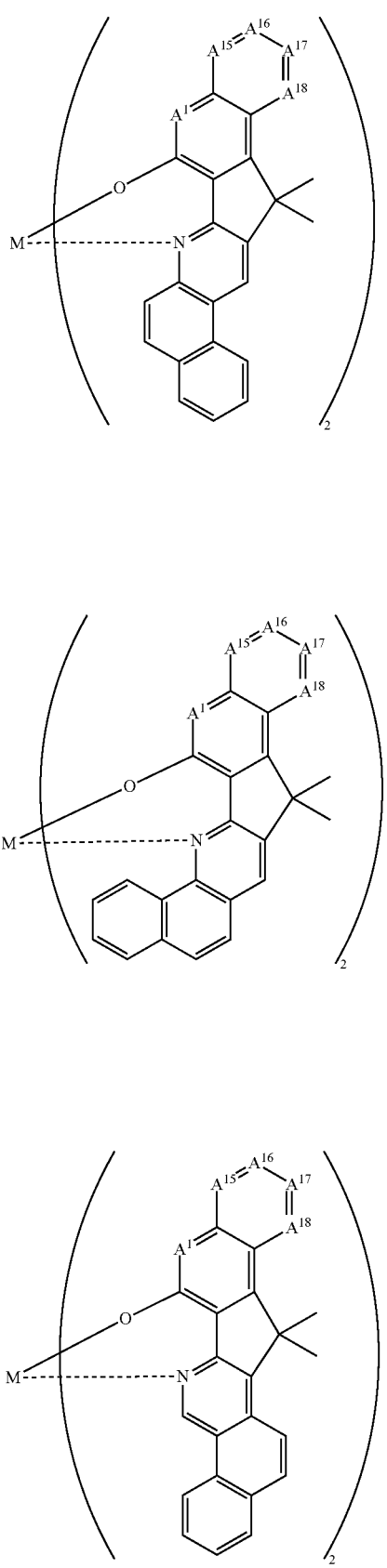

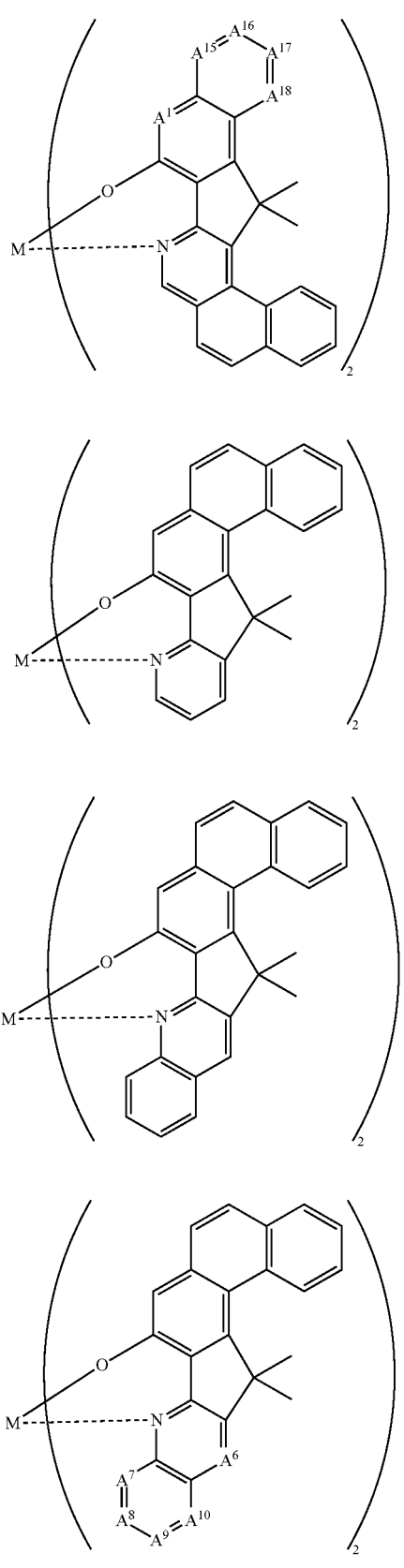
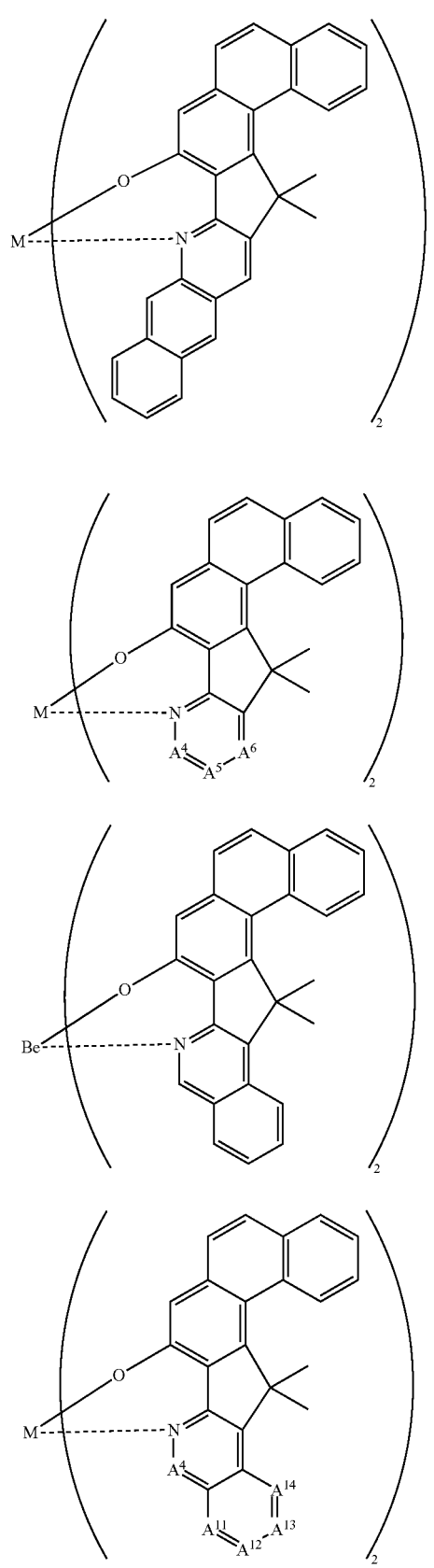

[2-68]
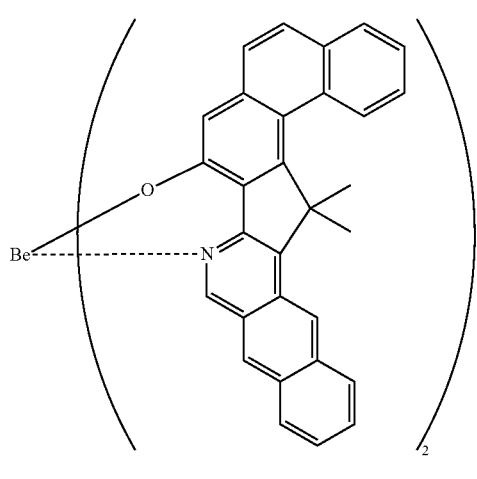
[2-69]
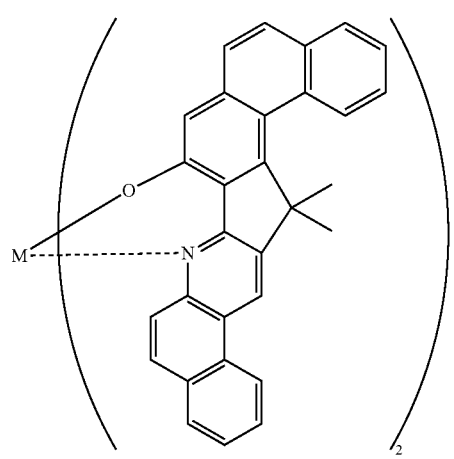
[2-70]
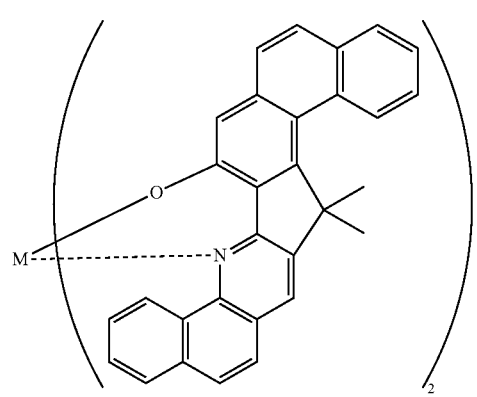
[2-71]
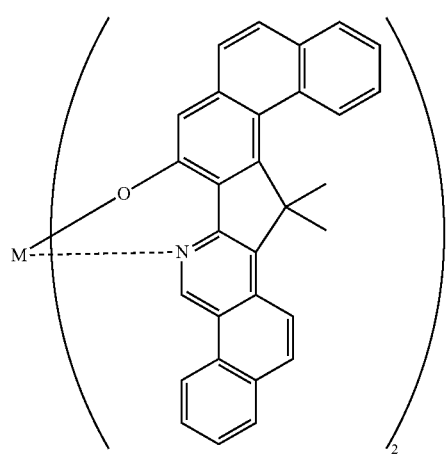
[2-72]
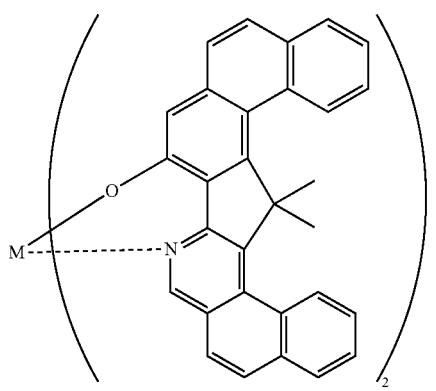
[2-73]
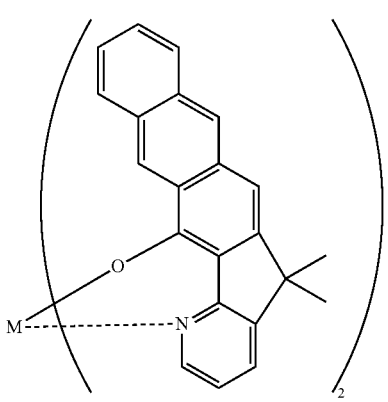

[2-74]
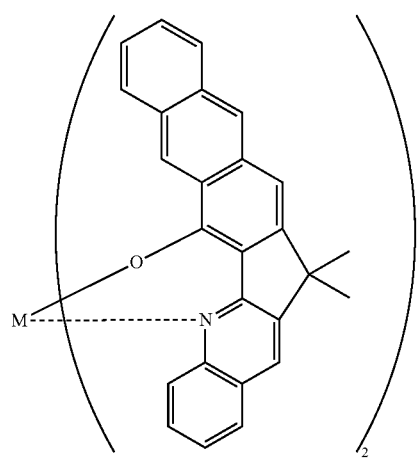
[2-75]
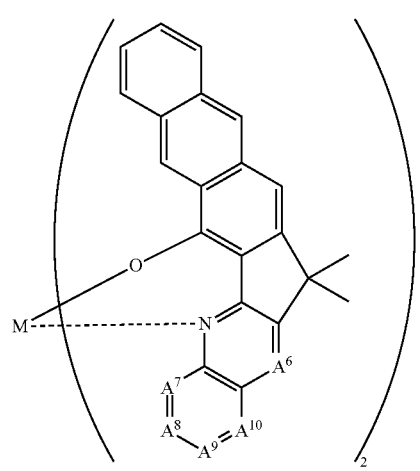
[2-76]
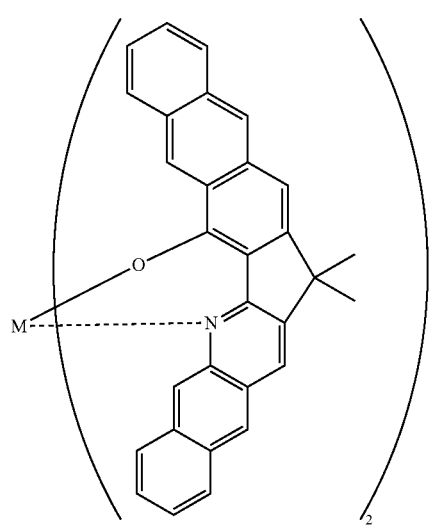
[2-77]
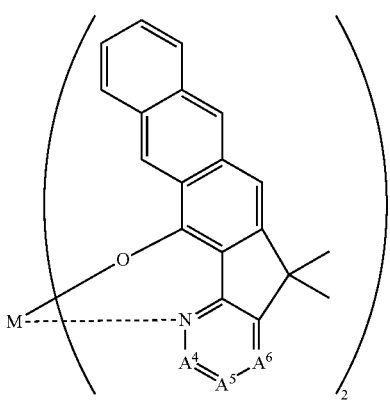
[2-78]
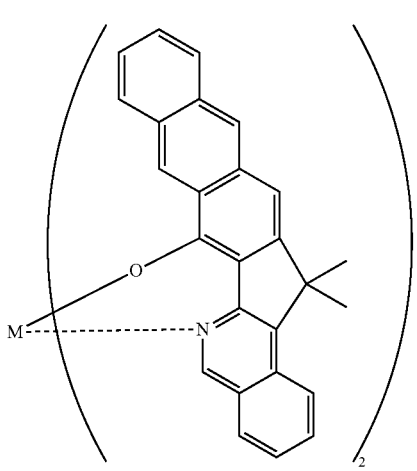
[2-79]
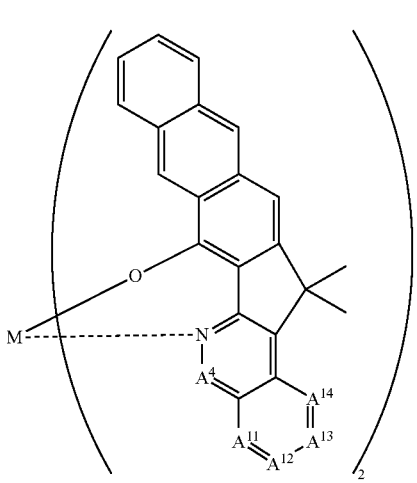

-continued
[2-80]
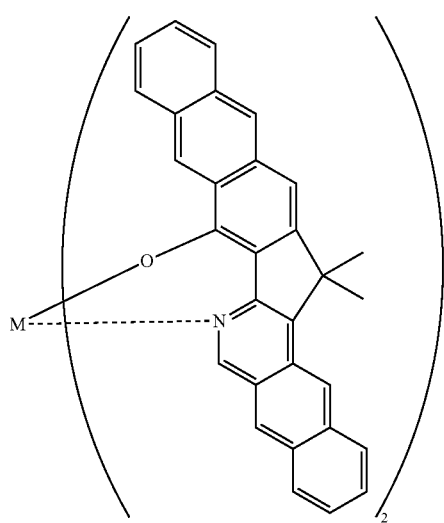
[2-81]
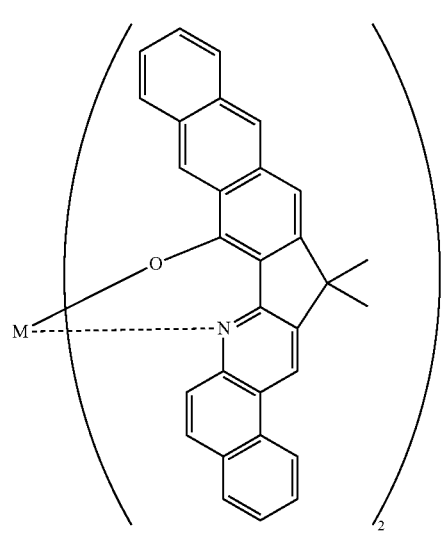
[2-82]
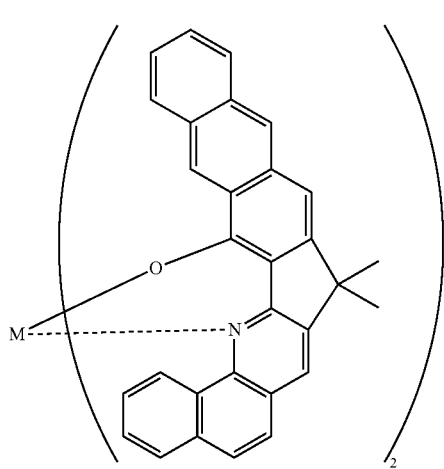
-continued
[2-83]
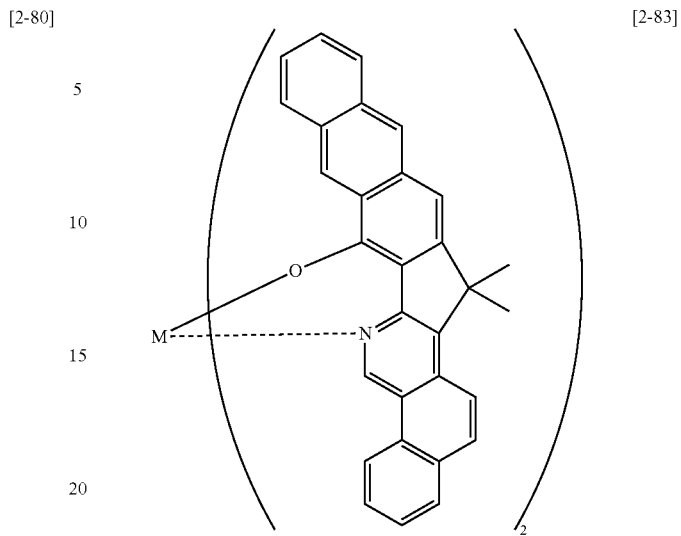
[2-84]
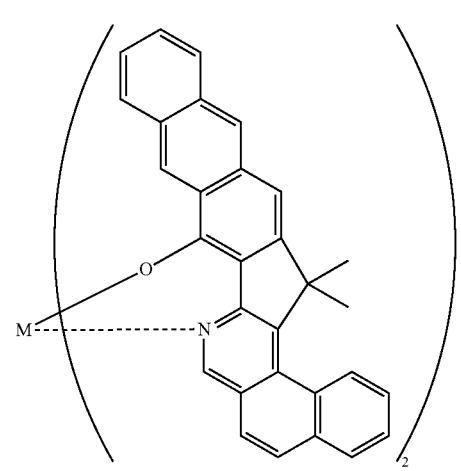
[2-85]
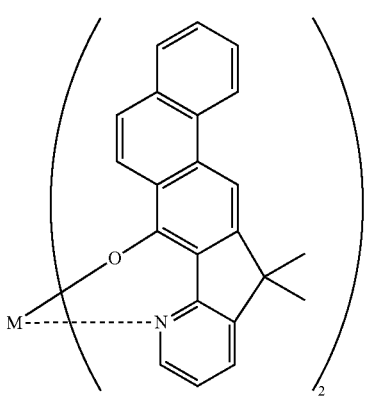

[2-86]
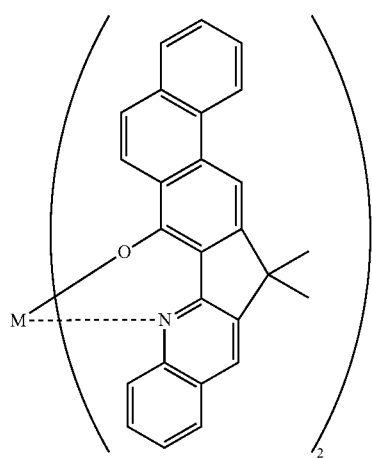
[2-89]
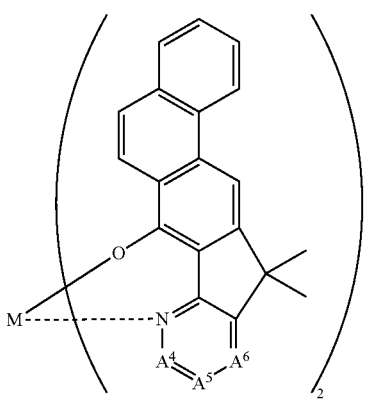
[2-87]
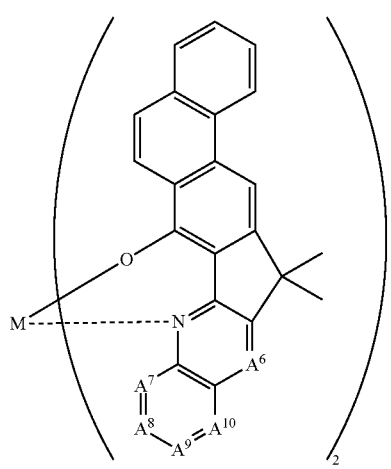
[2-90]
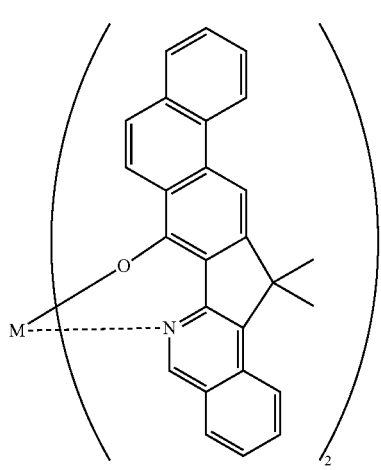
[2-88]
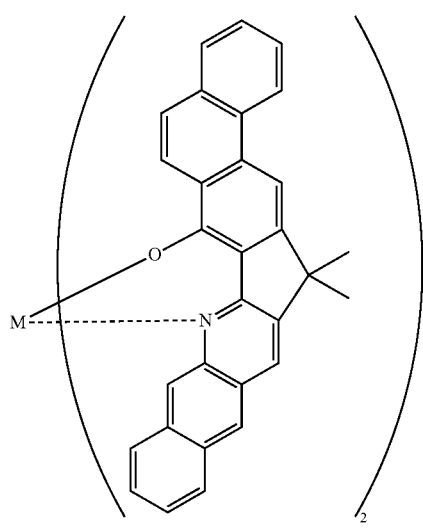
[2-91]
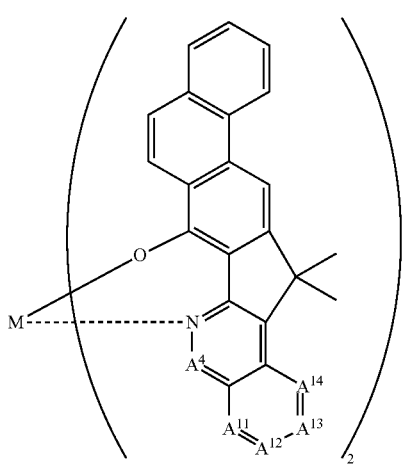

[2-92]
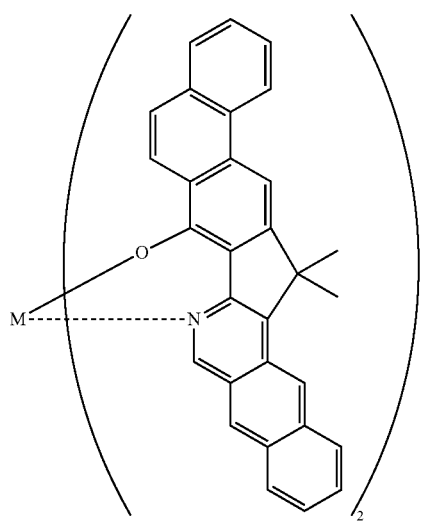
[2-93]
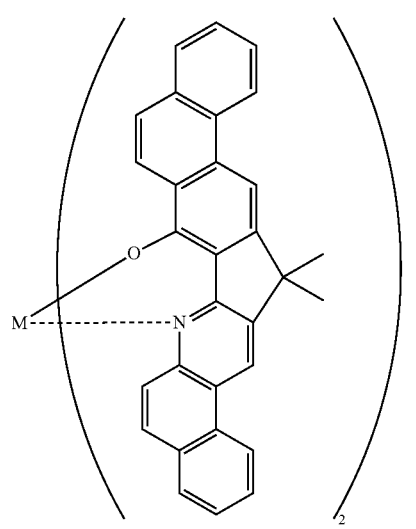
[2-94]
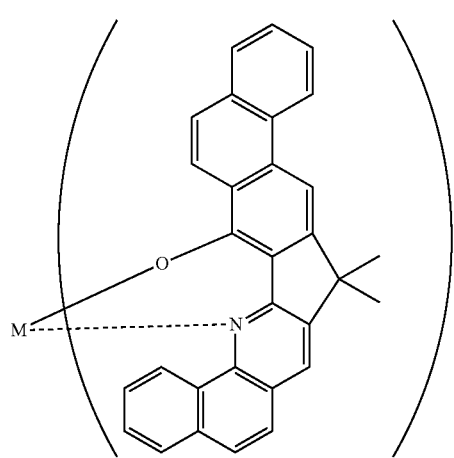
[2-95]
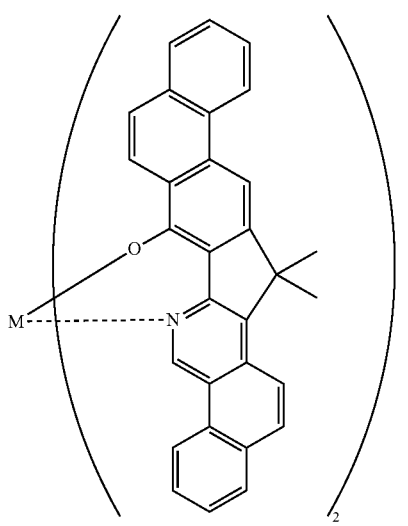
[2-96]
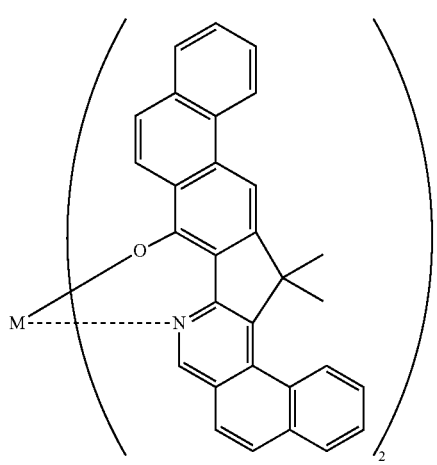
[2-97]
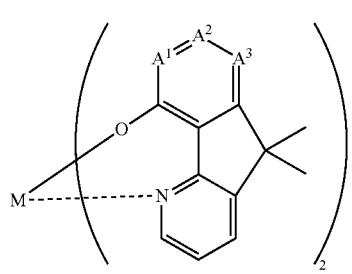
[2-98]
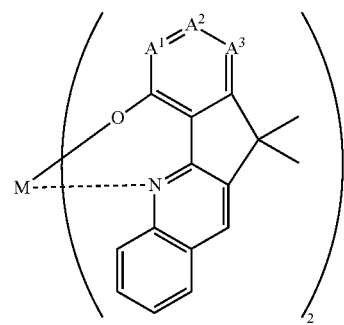

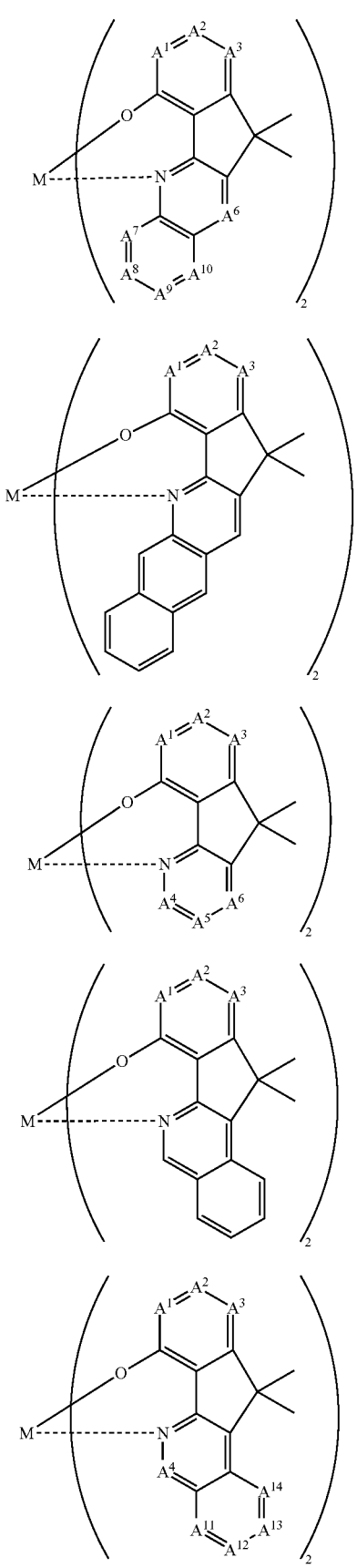
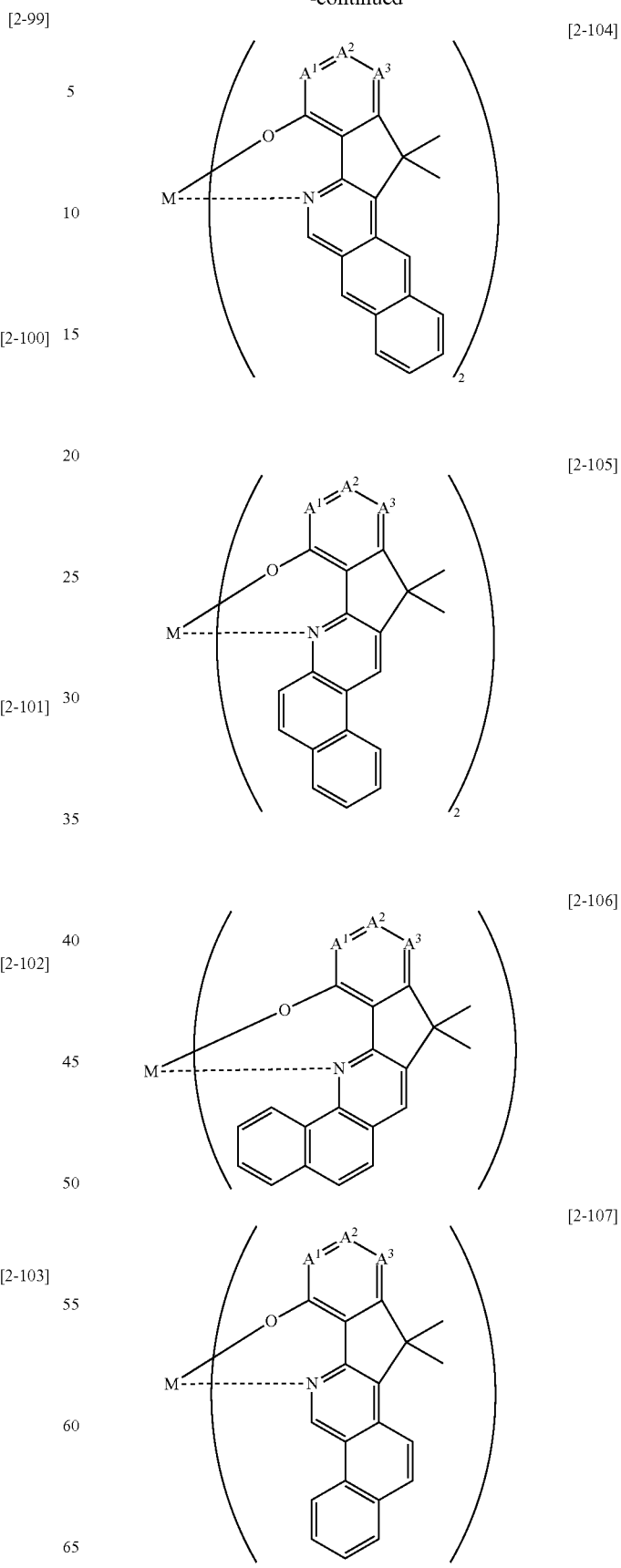

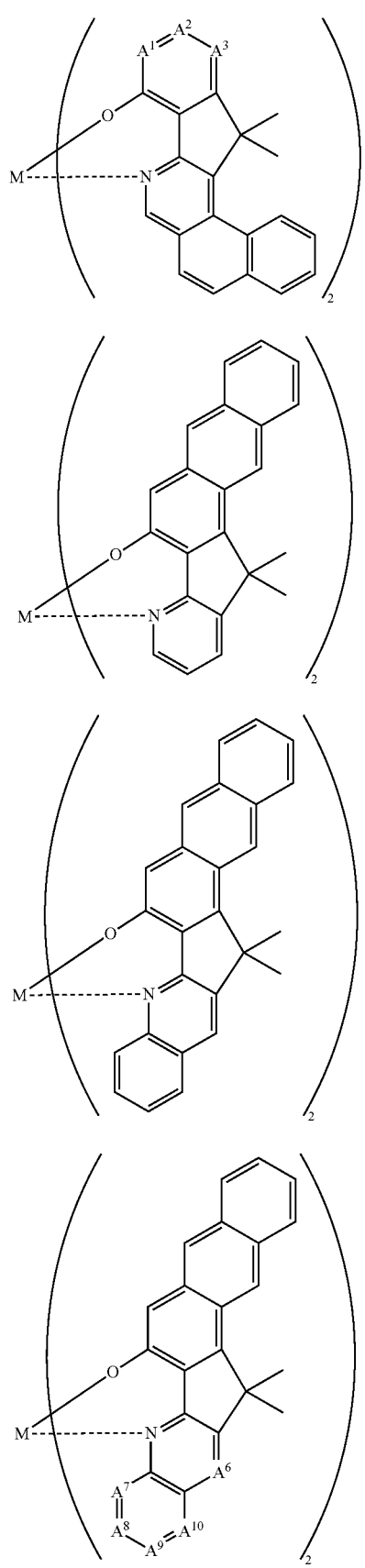
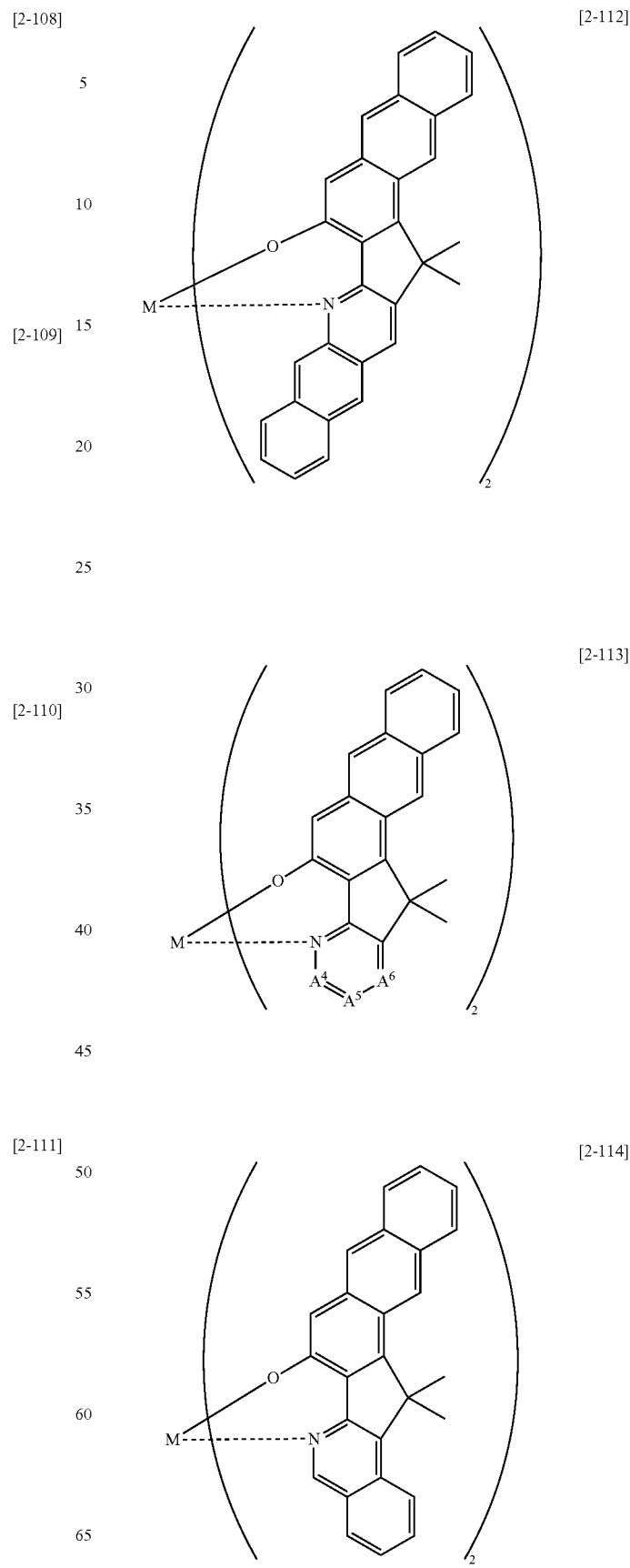

[2-115]
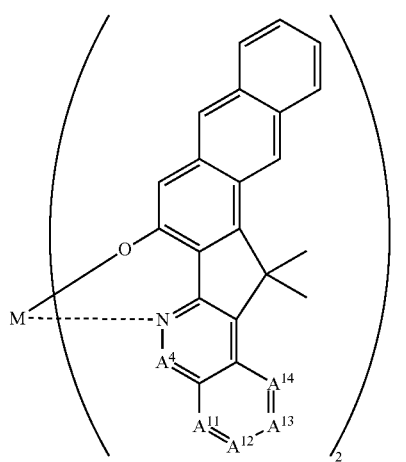
[2-116]
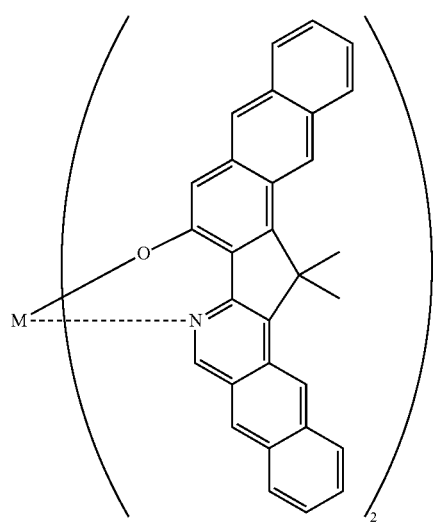
[2-117]
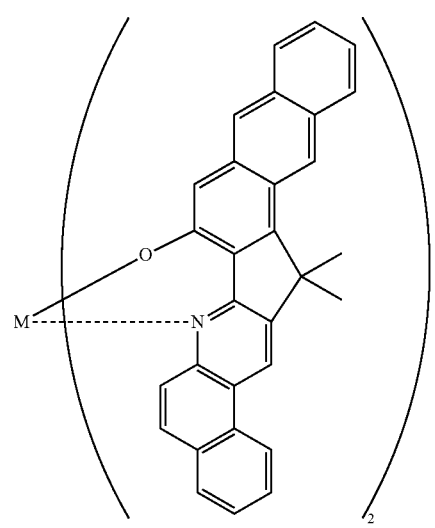
[-2-118]
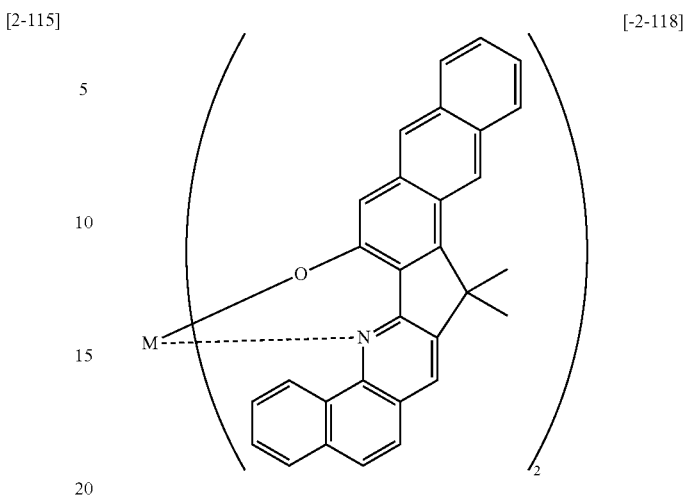
[2-119]
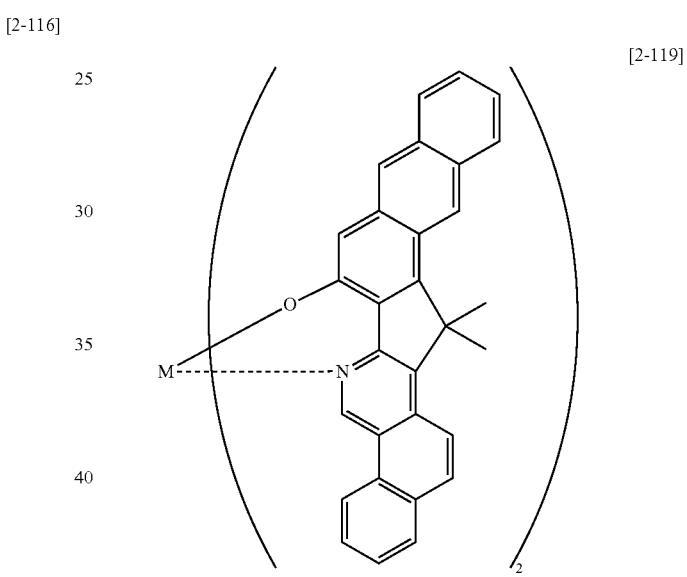
[2-120]
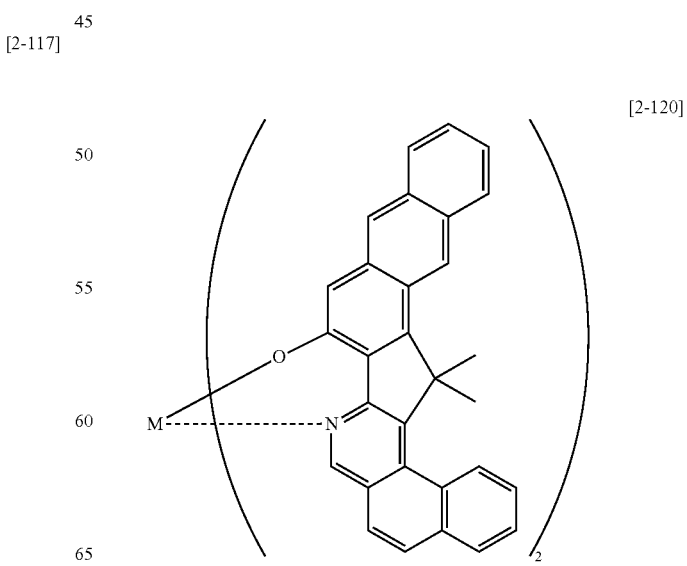

[2-121]
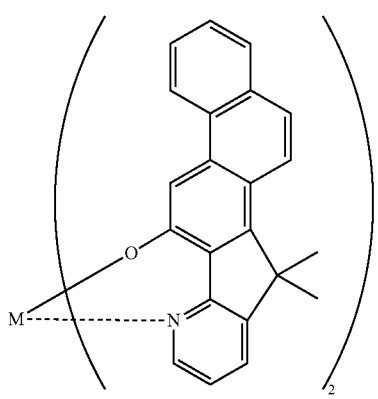
[2-122]
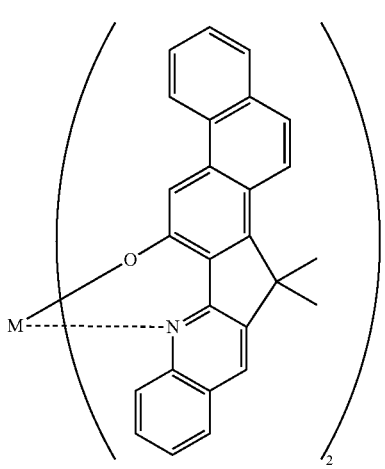
[2-123]
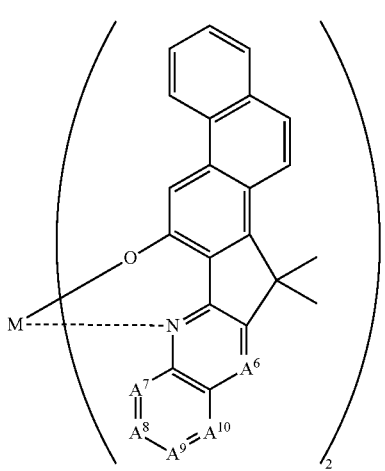
[2-124]
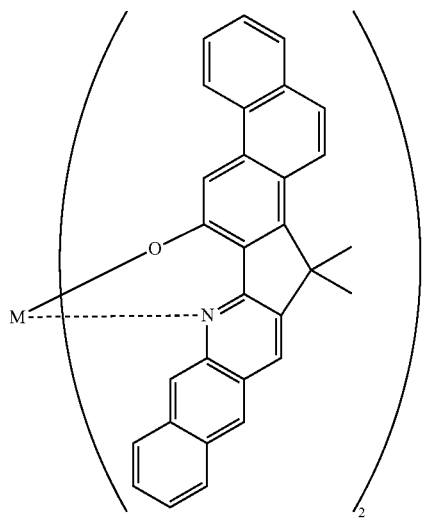
[2-125]
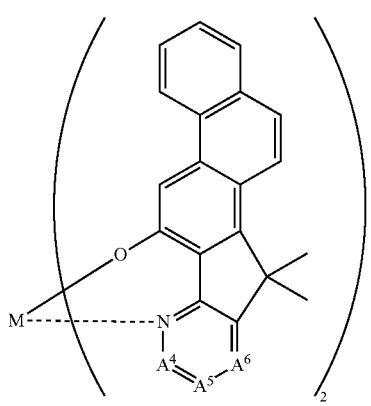
[2-126]
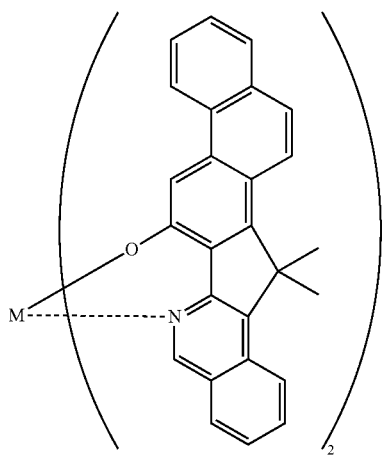

[2-127]
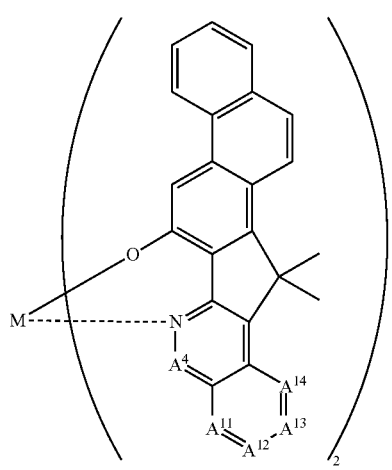
[2-128]
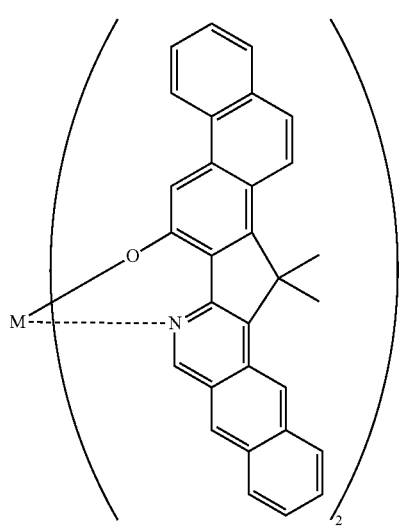
[2-129]
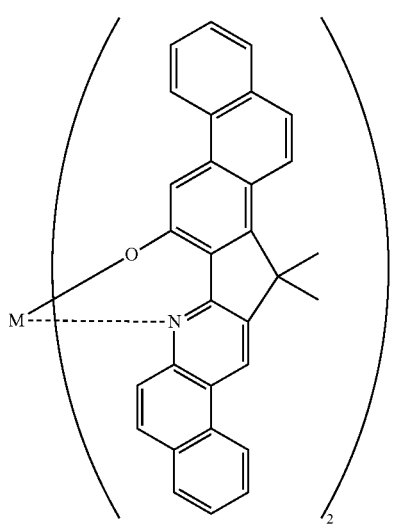
[2-130]
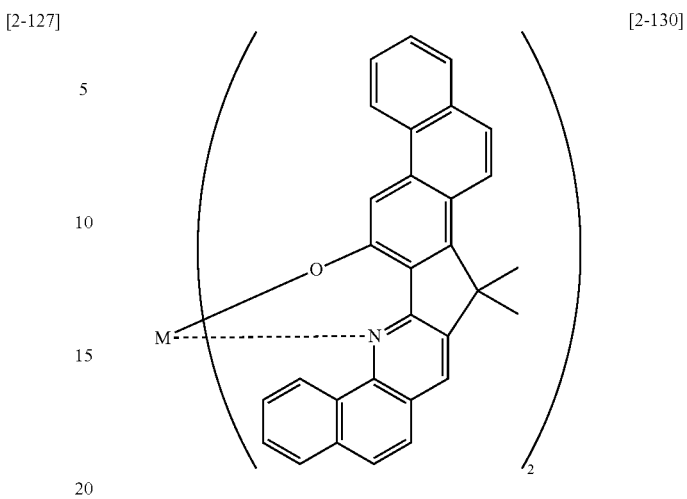
[2-131]
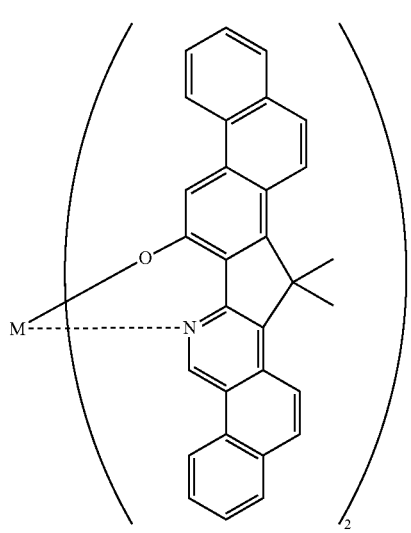
[2-132]
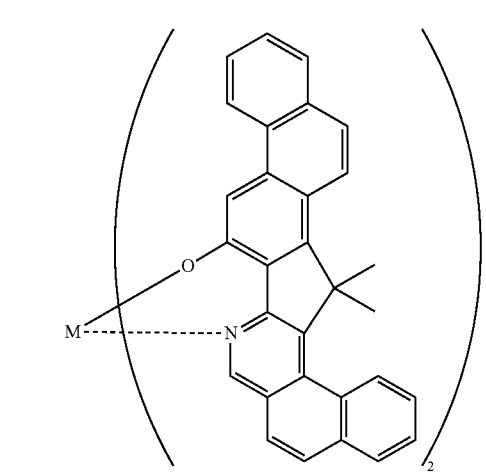

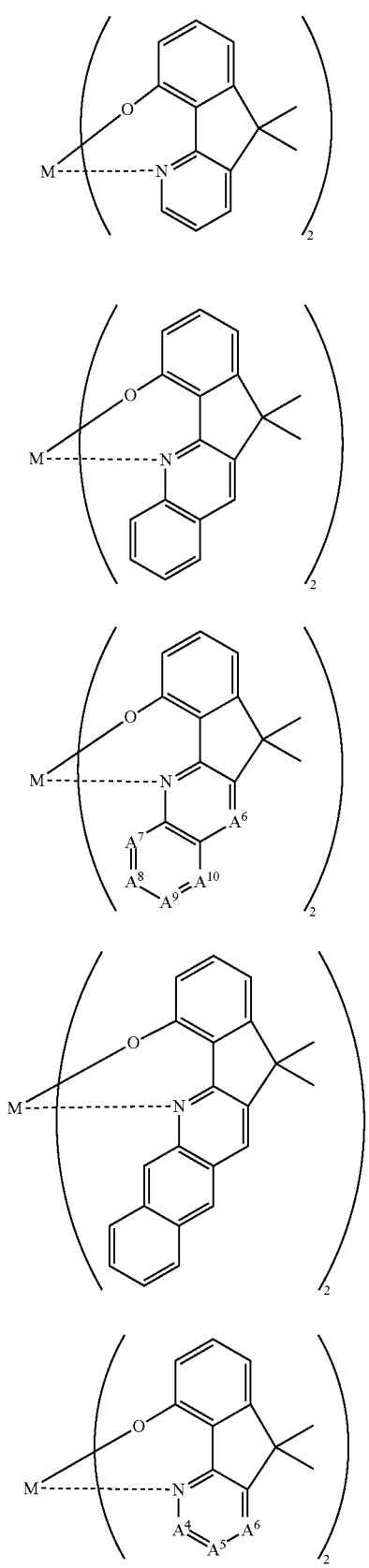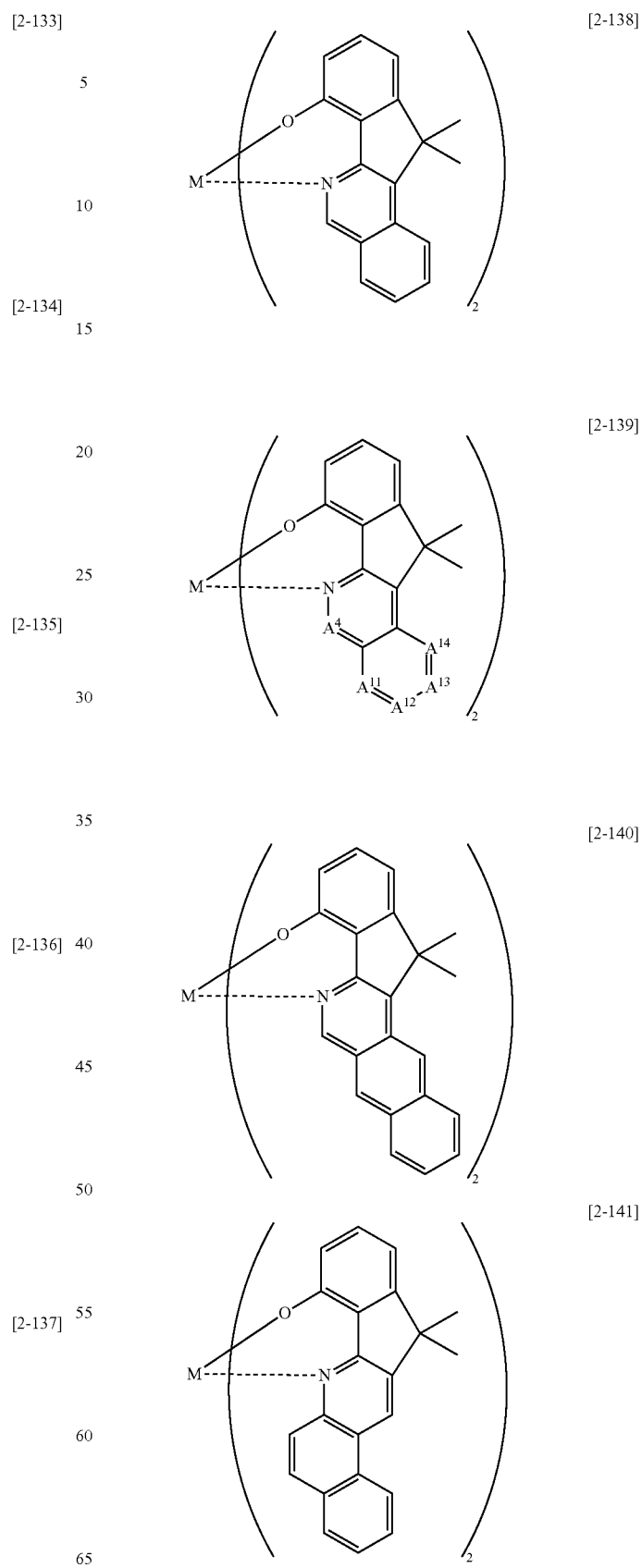

[2-142]
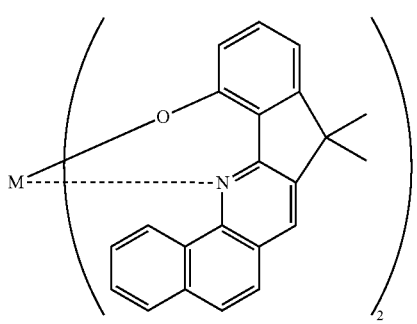

[2-143]
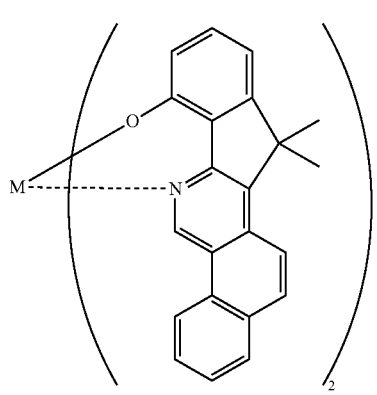

[2-144]
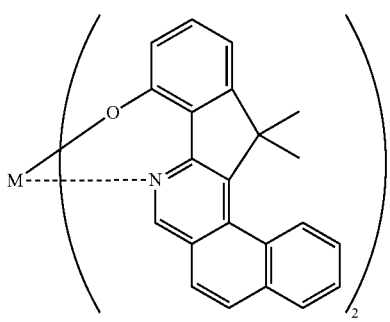

[2-145]
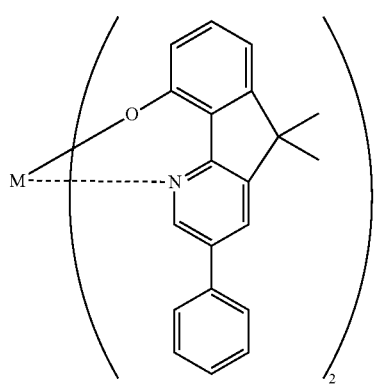

[2-146]
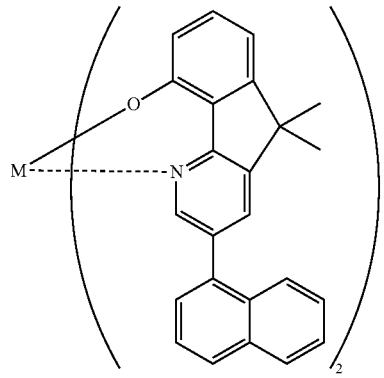

[2-147]
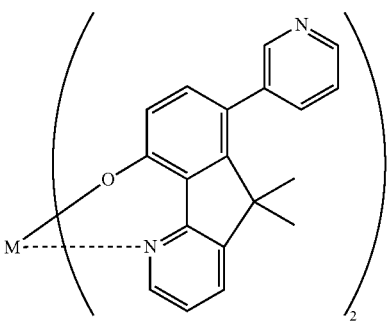

In Chemical Formulae 2-1 to 2-147, A1 to A18 are the same or different, and are a carbon atom or a nitrogen atom, provided that at least one of A1 to A18 is a nitrogen atom, and M is Be or Zn.

Referring to FIG. 1, an organic light emitting diode device according to one embodiment is described.

FIG. 1 is a schematic cross-sectional view showing an organic light emitting diode device according to one embodiment.

Referring to FIG. 1, the organic light emitting diode device includes a substrate 100, a first electrode 110 disposed on the substrate, an organic layer 120 disposed on the first electrode 110, and a second electrode 130 disposed on the organic layer 120.

The substrate 100 may include a substrate commonly used for an organic light emitting diode device, and in particular, a glass substrate, a plastic substrate, and the like may be used.

The first electrode 110 may be an anode, and may comprise a transparent conductor or an opaque conductor. The transparent conductor may include ITO (indium tin oxide), IZO (indium zinc oxide), TO (tin oxide), ZnO (zinc oxide), or a combination thereof. The opaque conductor may include silver (Ag), magnesium (Mg), aluminum (Al), platinum (Pt), palladium (Pd), gold (Au), nickel (Ni), neodymium (Nd), iridium (Ir), chromium (Cr), or a combination thereof. When the first electrode 110 comprises a transparent conductor, it may be a bottom emission type emitting light from the bottom.

The organic layer 120 may include at least one layer among a hole injection layer 121, a hole transport layer 123, an emission layer 125, an electron transport layer 127, and an electron injection layer 129 that are sequentially positioned on the first electrode.

The organic layer 120 may include a metal complex compound used for forming at least one layer among the hole injection layer 121, the hole transport layer 123, the emission layer 125, the electron transport layer 127, and the electron injection layer 129. In particular, the metal complex compound may be used to form the emission layer 125 or the electron transport layer 127.

The second electrode 130 may be a cathode and may be formed of a transparent conductor or an opaque conductor. The transparent conductor may include ITO (indium tin oxide), IZO (indium zinc oxide), TO (tin oxide), ZnO (zinc oxide), or a combination thereof. The opaque conductor may include silver (Ag), magnesium (Mg), aluminum (Al), platinum (Pt), palladium (Pd), gold (Au), nickel (Ni), neodymium (Nd), iridium (Ir), chromium (Cr), or a combination thereof. When the second electrode 130 comprises a transparent conductor, it may be a top emission type emitting light from the organic layer 120 to the top.

The organic layer may comprise the metal complex compound, and may increase luminous efficiency of an organic light emitting diode device and decrease its driving voltage.

The following examples illustrate this disclosure in more detail. These examples, however, are not in any sense to be interpreted as limiting the scope of this disclosure.

Preparation of Metal Complex Compound

Example 1-1

A compound represented by the following Chemical Formula 3-1 was prepared according to the following Reaction Scheme 1-1.

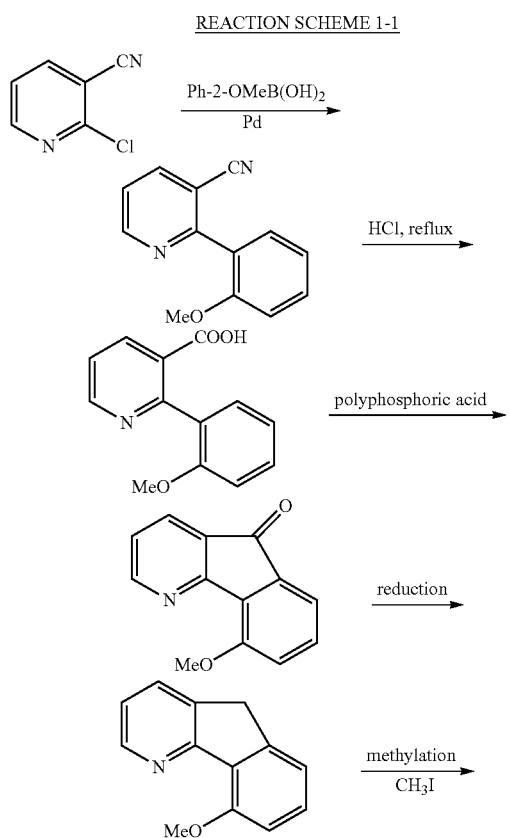

REACTION SCHEME 1-1

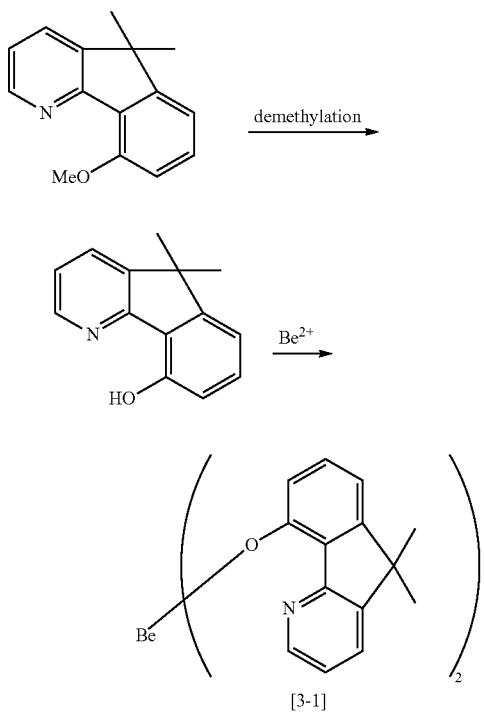

[3-1]

Example 1-2

A compound represented by the following Chemical Formula 3-2 was prepared according to the following Reaction Scheme 1-2.

REACTION SCHEME 1-2

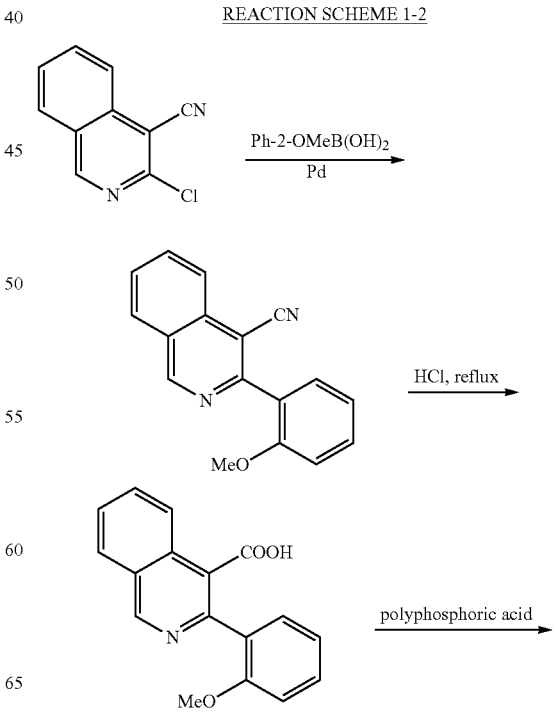

87
-continued
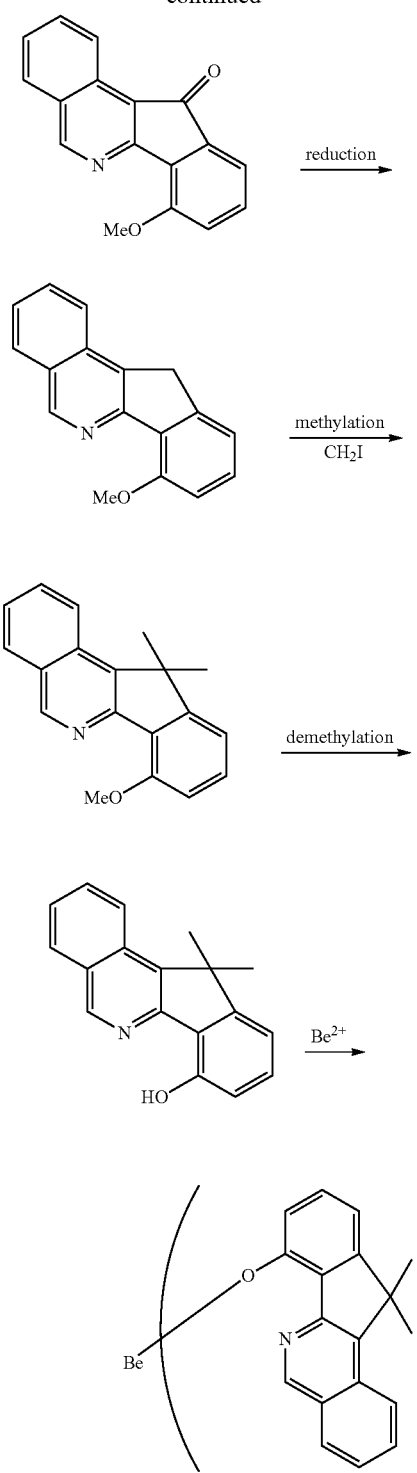
[3-2]
Example 1-3
A compound represented by the following Chemical Formula 3-3 was prepared according to the following Reaction Scheme 1-3.
88
[REACTION SCHEME 1-3]
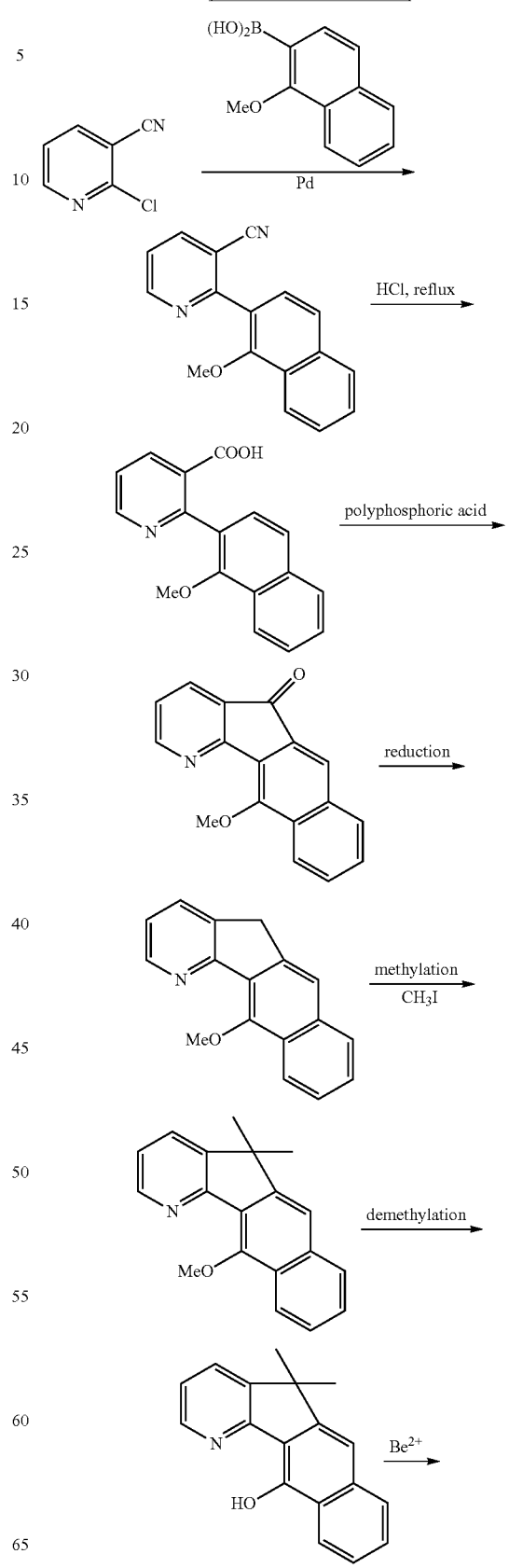

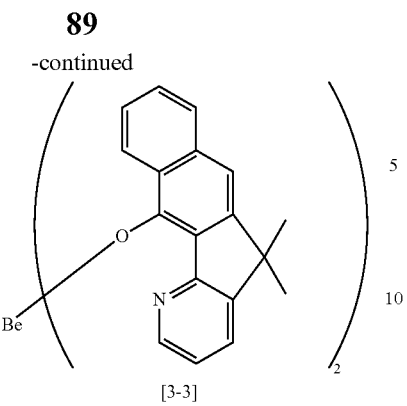
[3-3]
Example 1-4
A compound represented by the following Chemical Formula 3-4 was prepared according to the following Reaction Scheme 1-4.
[REACTION SCHEME 1-4]
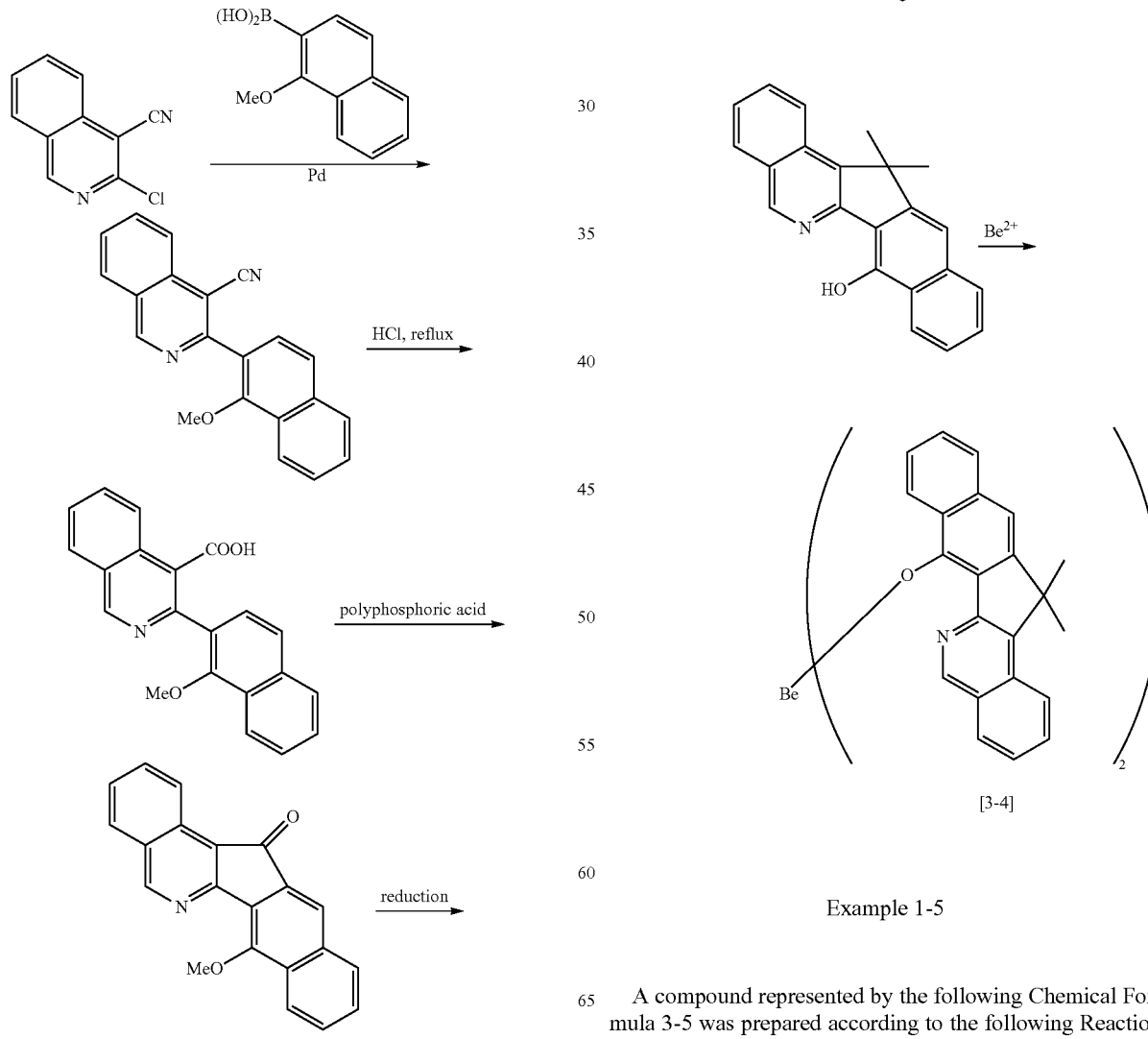
[3-4]
Example 1-5
A compound represented by the following Chemical Formula 3-5 was prepared according to the following Reaction Scheme 1-5.

REACTION SCHEME 1-5
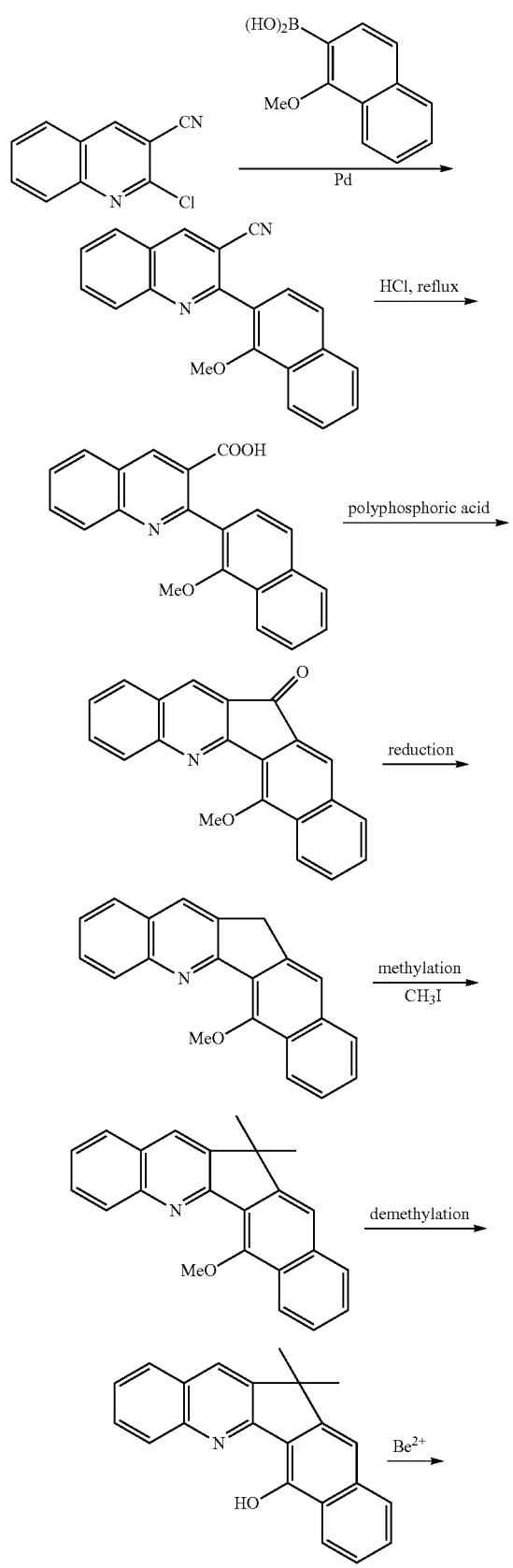
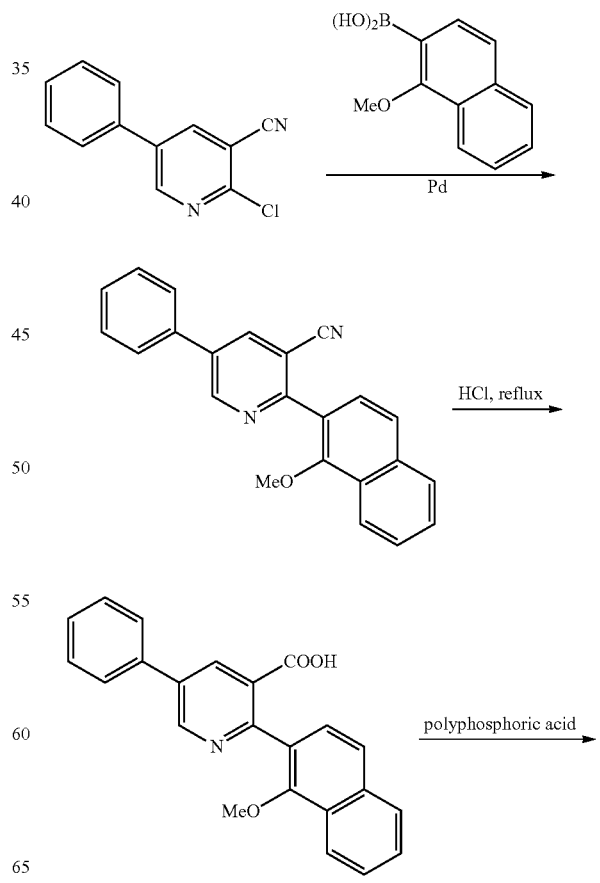
Example 1-6
A compound represented by the following Chemical Formula 3-6 was prepared according to the following Reaction Scheme 1-6.
REACTION SCHEME 1-6

93
-continued
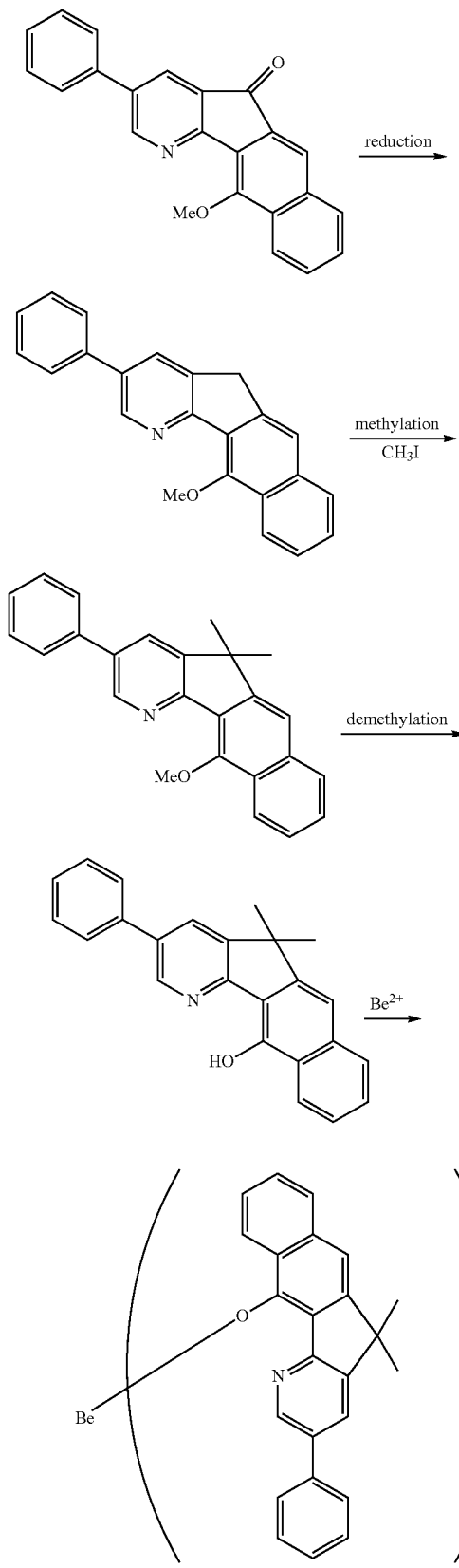
[3-6]
94
Example 1-7
A compound represented by the following Chemical Formula 3-7 was prepared according to the following Reaction Scheme 1-7.
REACTION SCHEME 1-7
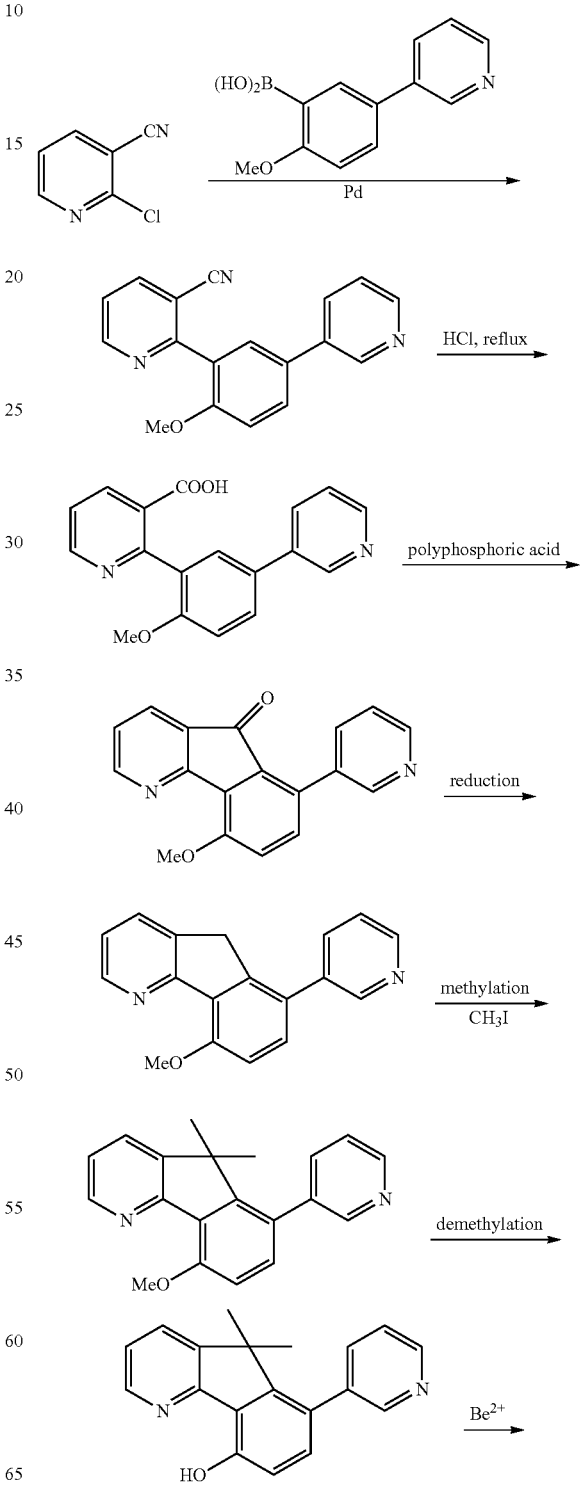

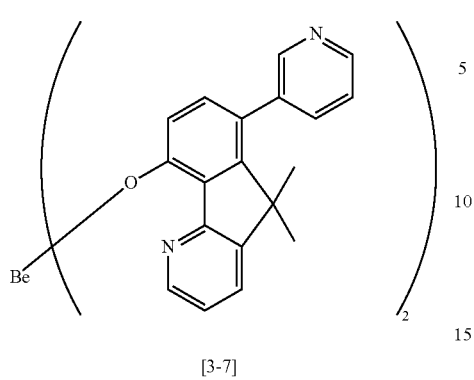
[3-7]
Example 1-8
A compound represented by the following Chemical Formula 3-8 was prepared according to the following Reaction Scheme 1-8.
REACTION SCHEME 1-8
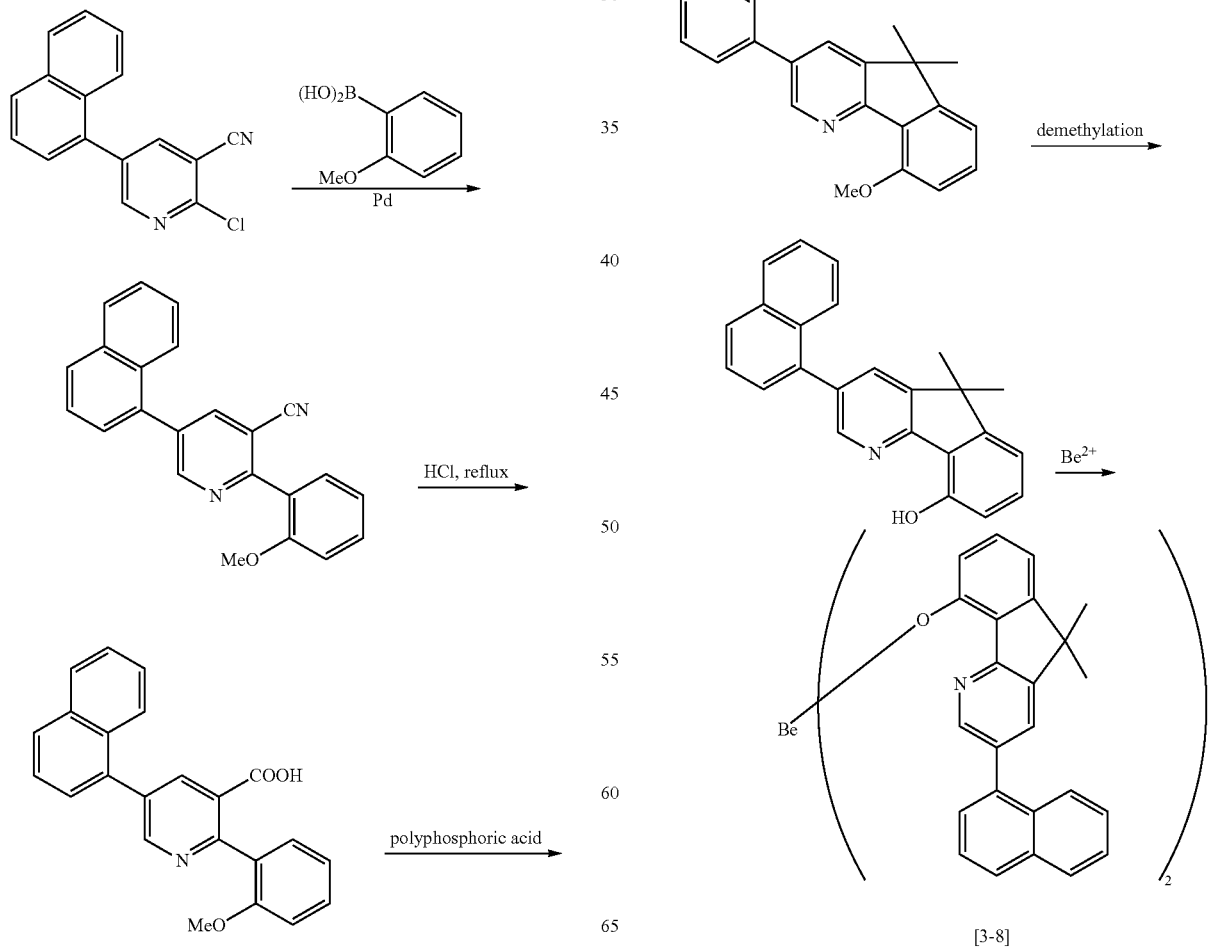
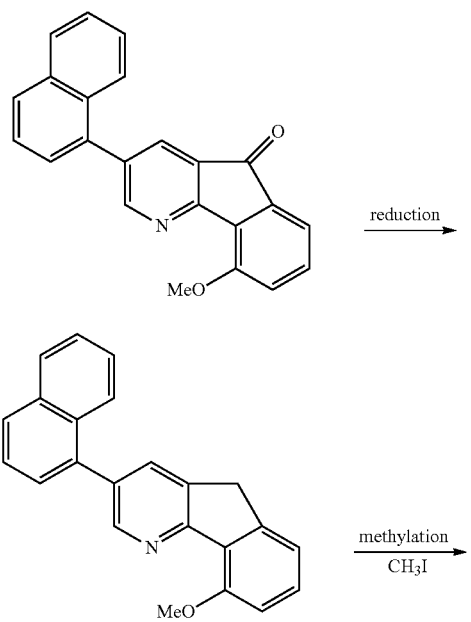
[3-8]

Example 1-9
A compound represented by the following Chemical Formula 3-9 was prepared according to the following Reaction Scheme 1-9.
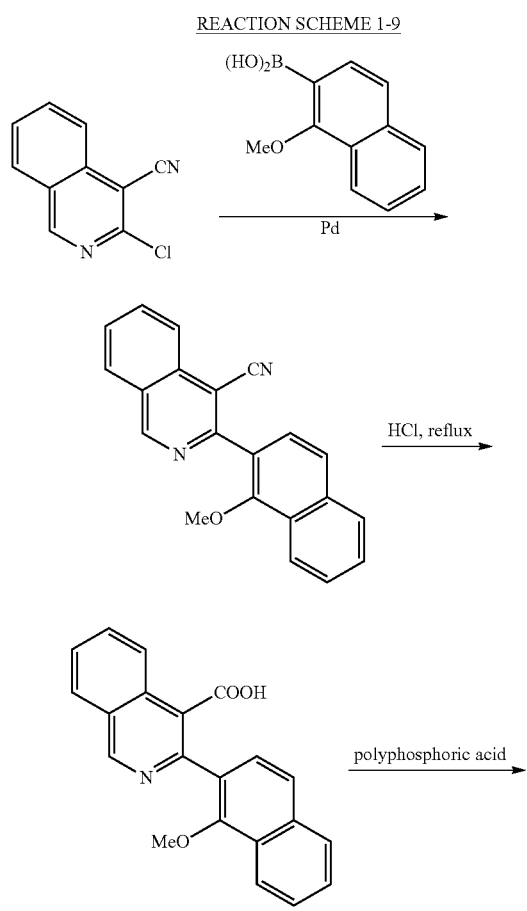
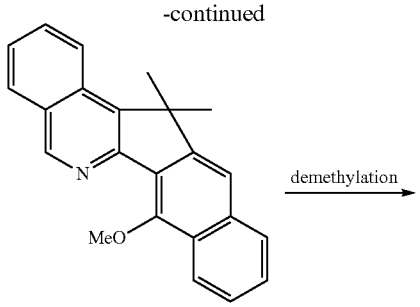
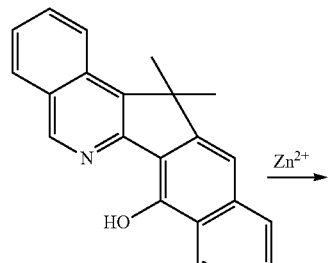
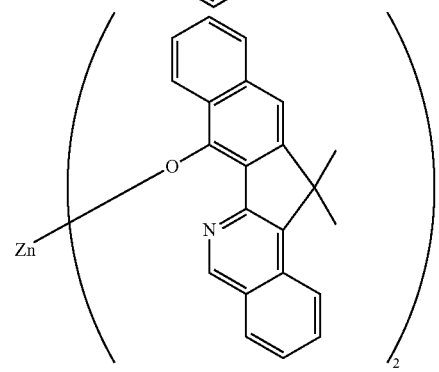
[3-9]
Example 1-10
A compound represented by the following Chemical Formula 3-10 was prepared according to the following Reaction Scheme 1-10.
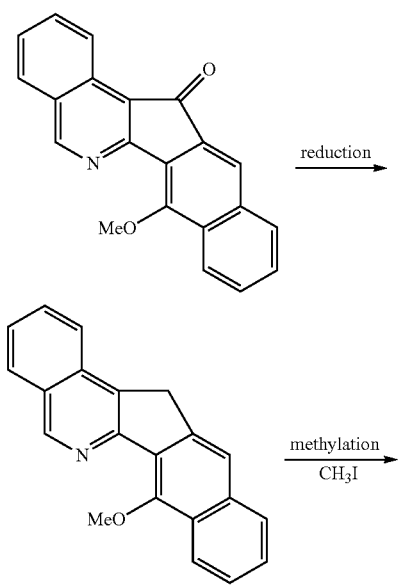
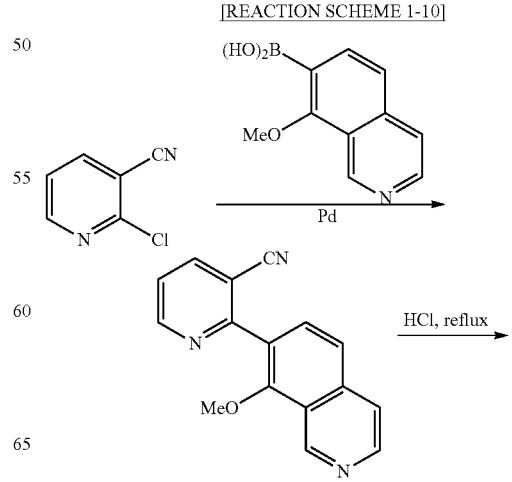

-continued
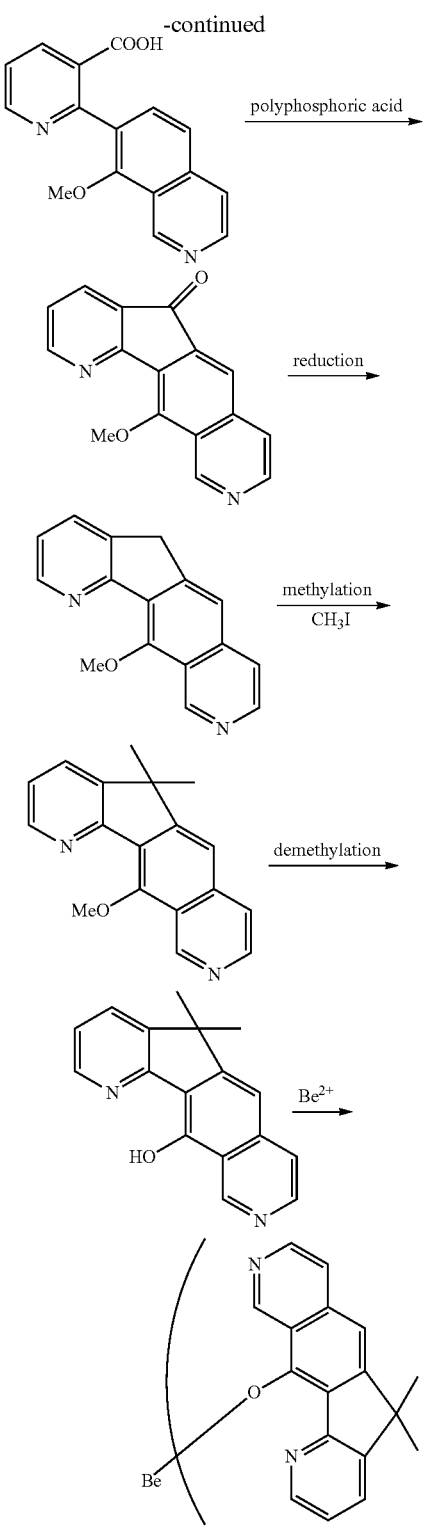
Example 1-11
A compound represented by the following Chemical Formula 3-11 was prepared according to the following Reaction Scheme 1-11.
REACTION SCHEME 1-11
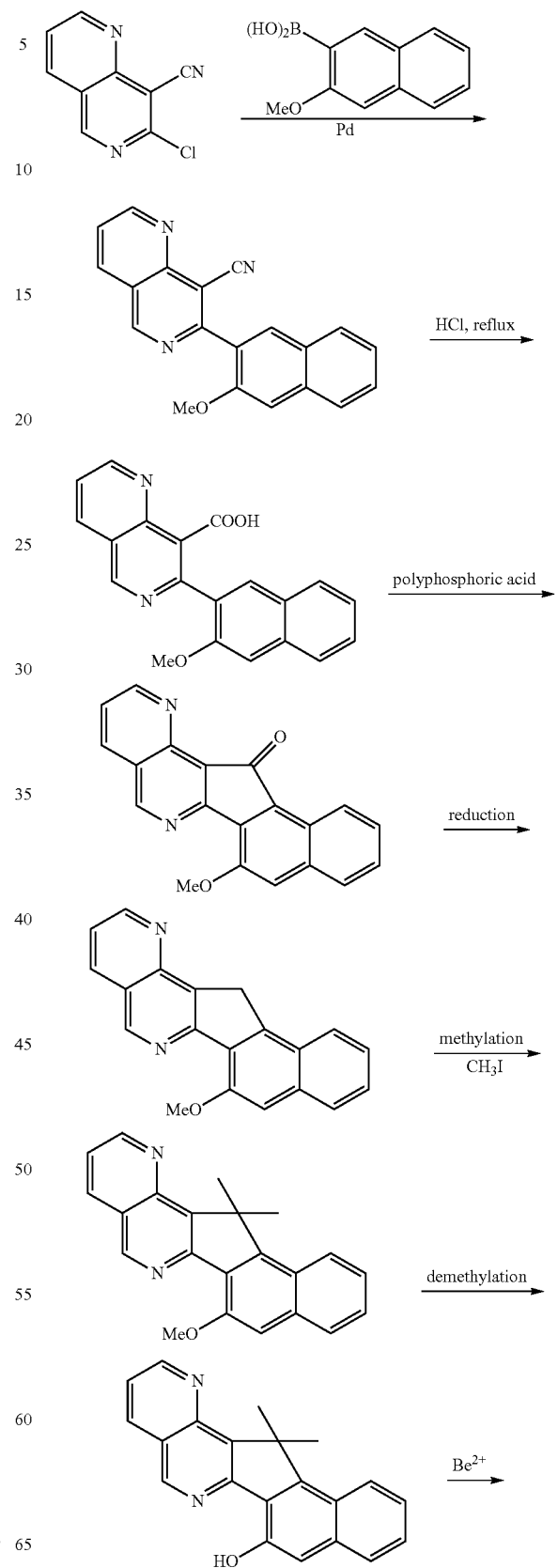

101
-continued
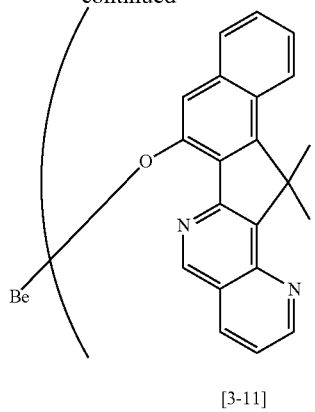
[3-11]
Example 1-12
A compound represented by the following Chemical Formula 3-12 was prepared according to the following Reaction Scheme 1-12.
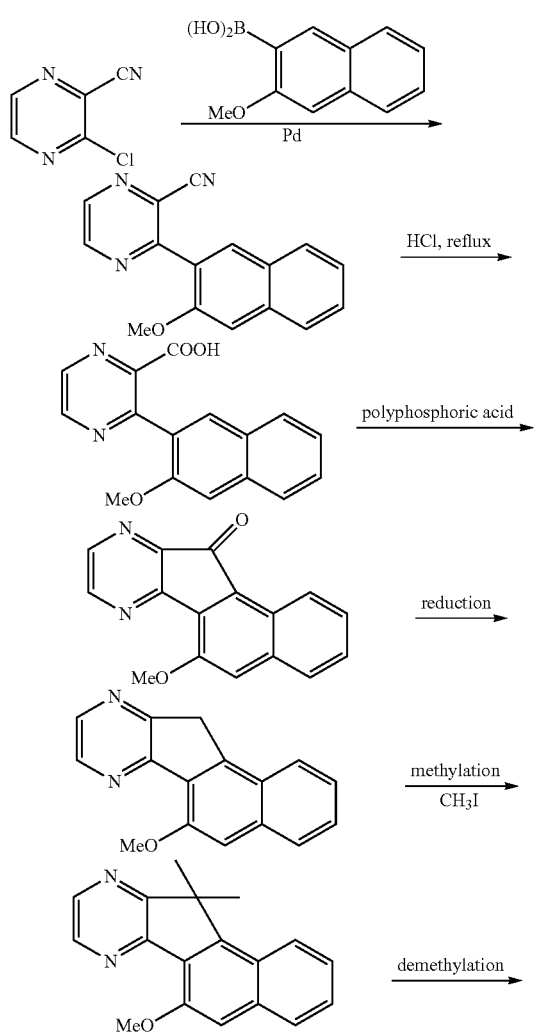
102
-continued
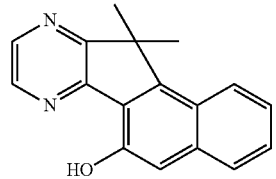
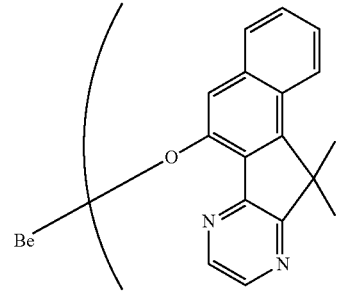
[3-12]
Example 1-13
A compound represented by the following Chemical Formula 3-13 was prepared according to the following Reaction Scheme 1-13.
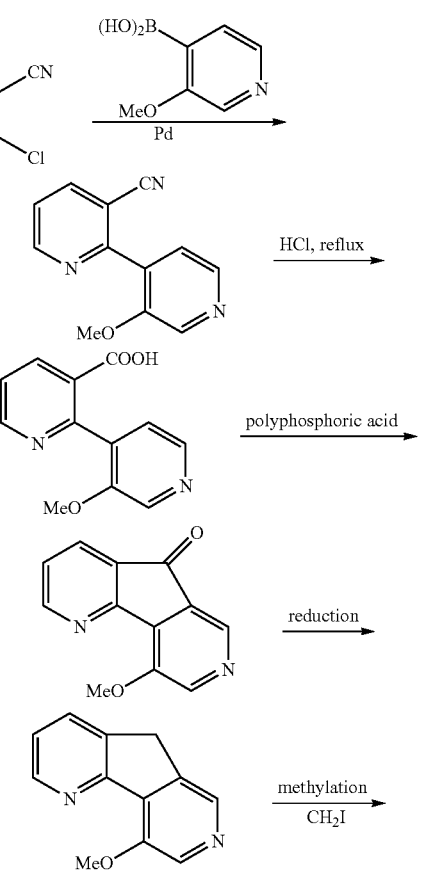

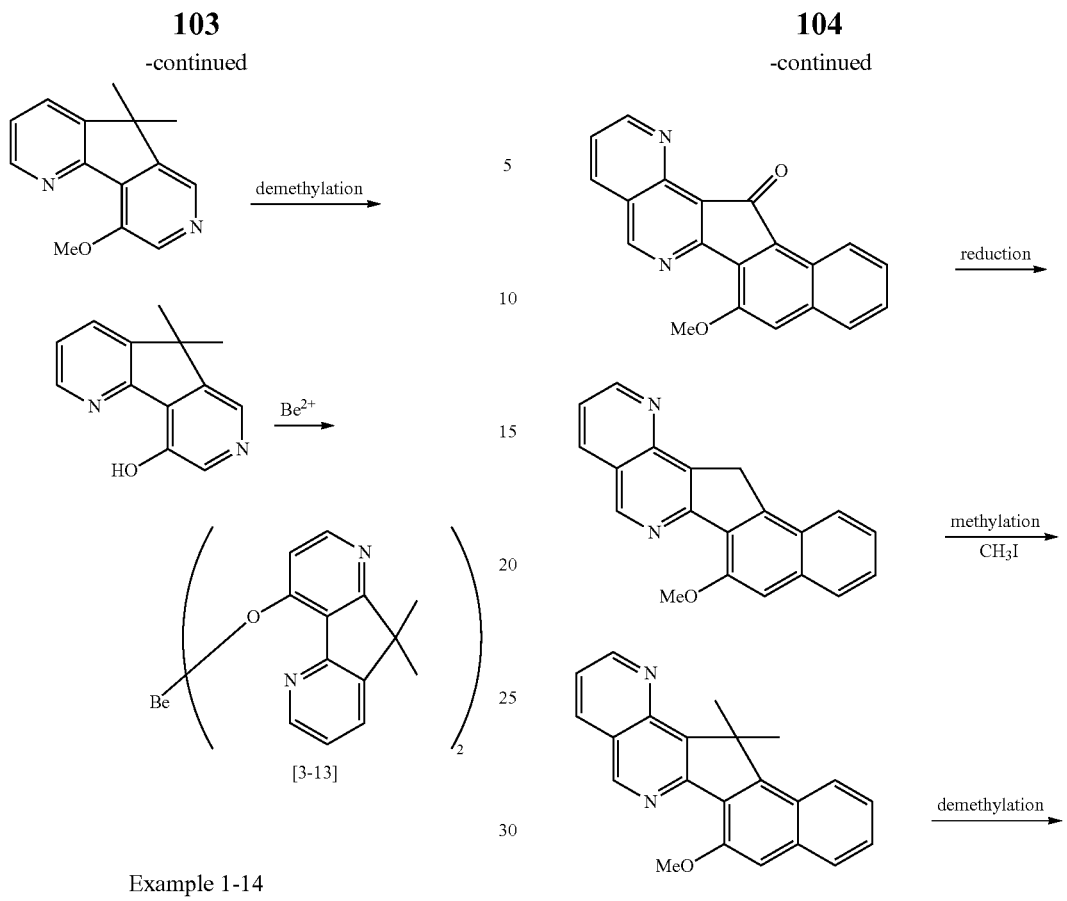
Example 1-14
A compound represented by the following Chemical Formula 3-14 was prepared according to the following Reaction Scheme 1-14.
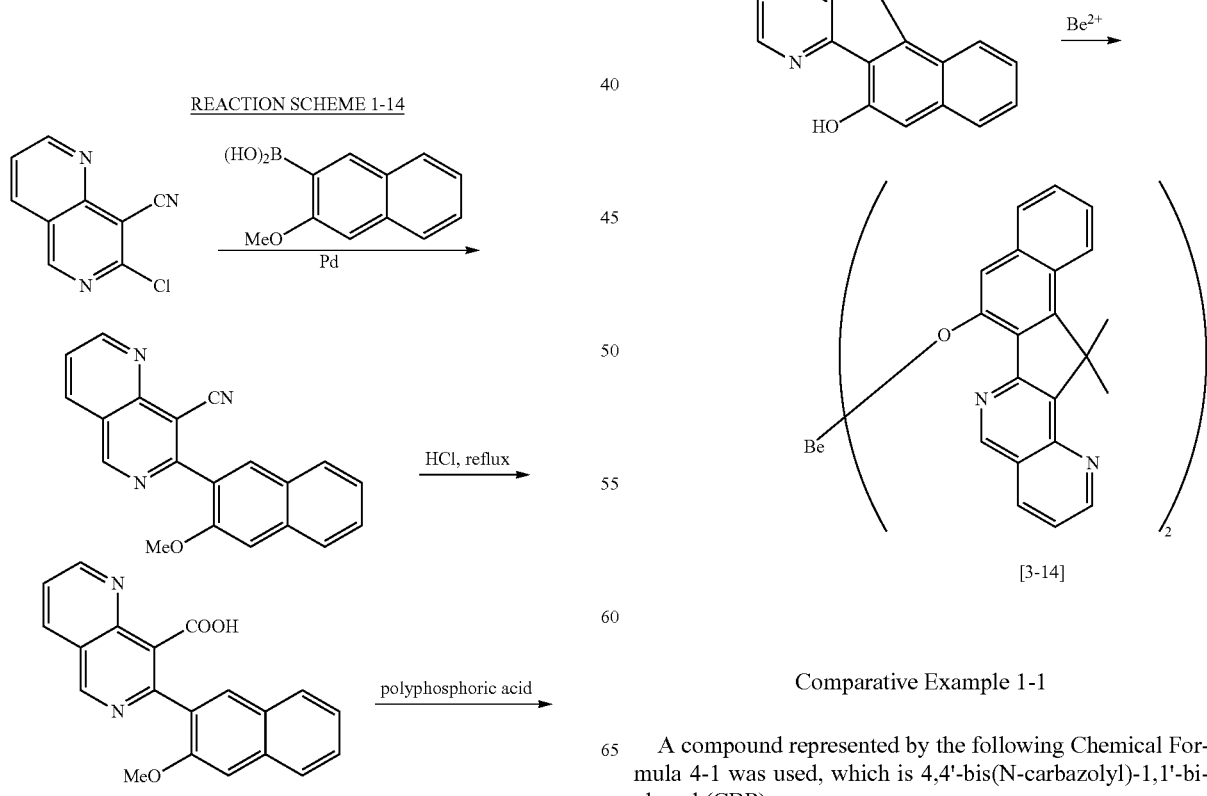
Comparative Example 1-1
A compound represented by the following Chemical Formula 4-1 was used, which is 4,4'-bis(N-carbazolyl)-1,1'-biphenyl (CBP).

CHEMICAL FORMULA 4-1

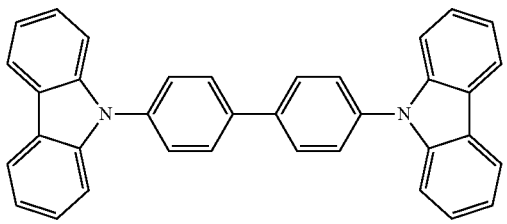

Comparative Example 1-2

A compound represented by the following Chemical Formula 4-2 was used, which is aluminum(III)bis(2-methyl-8-quinolinato)-4-phenylphenolate (BAlq).

[CHEMICAL FORMULA 4-2]

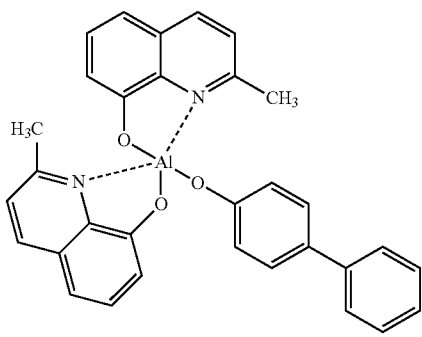

Fabrication of an Organic Light Emitting Diode Device

Example 2-1

A lower electrode was prepared by laminating Ag/ITO on a glass substrate and patterning it, and then disposing a hole injection layer to be 70 nm thick on the lower electrode by depositing a compound represented by the following Chemical Formula 5-1, an interlayer to be 5 nm thick thereon by depositing another compound represented by following Chemical Formula 5-2, and a hole transport layer to be 100 nm thick thereon by depositing a compound represented by the following Chemical Formula 5-3. Next, a green phosphorescence emission layer was disposed to be 40 nm thick by depositing a compound represented by the following Chemical Formula 5-4 as a dopant and another compound represented by the above Chemical Formula 3-1 prepared in Example 1 as a host. Then, an electron transport layer was disposed to be 30 nm thick thereon by depositing a compound represented by the following Chemical Formula 5-5, and an electron injection layer was disposed to be 0.5 nm thick thereon by depositing a compound represented by the following Chemical Formula 5-6. Next, an upper electrode was disposed to be 200 nm thick thereon by depositing MgAg, fabricating an organic light emitting diode device. Herein, the green phosphorescence emission layer included the dopant in an amount of 12 wt % based on the entire amount of the emission layer. The electron injection layer was included in an amount of 50 wt % based on the entire amount of the electron transport layer and the electron injection layer.

CHEMICAL FORMULA 5-1

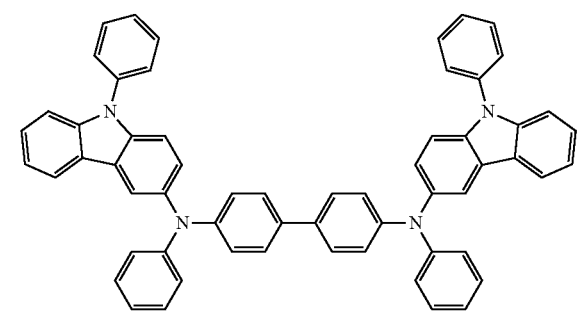

CHEMICAL FORMULA 5-2

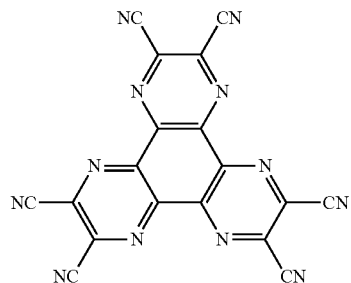

CHEMICAL FORMULA 5-3

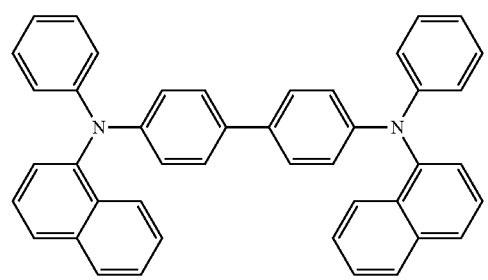

CHEMICAL FORMULA 5-4

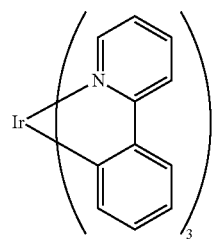

CHEMICAL FORMULA 5-5

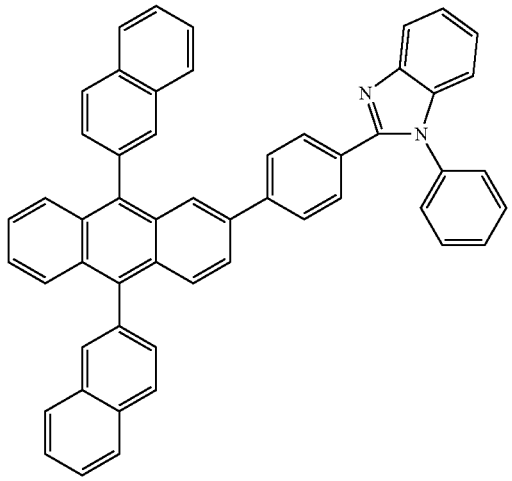

CHEMICAL FORMULA 5-6

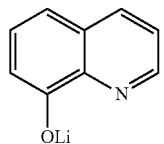

Example 2-2

An organic light emitting diode device was fabricated according to the same method as Example 2-1, except for using the compound represented by the above Chemical Formula 3-2 prepared according to Example 1-2 as a host.

Example 2-3

An organic light emitting diode device was fabricated according to the same method as Example 2-1, except for using the compound represented by the above Chemical Formula 3-3 prepared according to Example 1-3 as a host.

Example 2-4

An organic light emitting diode device was fabricated according to the same method as Example 2-1, except for using the compound represented by the above Chemical Formula 3-4 prepared according to Example 1-4 as a host.

Example 2-5

An organic light emitting diode device was fabricated according to the same method as Example 2-1, except for using the compound represented by the above Chemical Formula 3-5 prepared according to Example 1-5 as a host.

Example 2-6

An organic light emitting diode device was fabricated according to the same method as Example 2-1, except for using the compound represented by the above Chemical Formula 3-6 prepared according to Example 1-6 as a host.

Example 2-7

An organic light emitting diode device was fabricated according to the same method as Example 2-1, except for using the compound represented by the above Chemical Formula 3-7 prepared according to Example 1-7 as a host.

Example 2-8

An organic light emitting diode device was fabricated according to the same method as Example 2-1, except for using the compound represented by the above Chemical Formula 3-8 prepared according to Example 1-8 as a host.

Example 2-9

An organic light emitting diode device was fabricated according to the same method as Example 2-1, except for using the compound represented by the above Chemical Formula 3-9 prepared according to Example 1-9 as a host.

Example 2-10

An organic light emitting diode device was fabricated according to the same method as Example 2-1, except for using the compound represented by the above Chemical Formula 3-10 prepared according to Example 1-10 as a host.

Example 2-11

An organic light emitting diode device was fabricated according to the same method as Example 2-1, except for using the compound represented by the above Chemical Formula 3-11 prepared according to Example 1-11 as a host.

Example 2-12

An organic light emitting diode device was fabricated according to the same method as Example 2-1, except for using the compound represented by the above Chemical Formula 3-12 prepared according to Example 1-12 as a host.

Example 2-13

An organic light emitting diode device was fabricated according to the same method as Example 2-1, except for using the compound represented by the above Chemical Formula 3-13 prepared according to Example 1-13 as a host.

Example 2-14

An organic light emitting diode device was fabricated according to the same method as Example 2-1, except for using the compound represented by the above Chemical Formula 3-14 prepared according to Example 1-14 as a host.

Comparative Example 2

An organic light emitting diode device was fabricated according to the same method as Example 2-1, except for using the compound represented by the above Chemical Formula 4-1 prepared according to Comparative Example 1-1 as a host.

Example 3-1

A lower electrode was prepared by laminating Ag/ITO on a glass substrate and patterning it, and then disposing a hole injection layer be 70 nm thick thereon by depositing a compound represented by the above Chemical Formula 5-1 to, an interlayer to be 5 nm thick thereon by depositing a compound represented by the above Chemical Formula 5-2, and a hole transport layer to be 155 nm thick thereon by depositing a compound represented by the above Chemical Formula 5-3. Next, a red phosphorescence emission layer including a compound represented by the following Chemical Formula 5-7 as a dopant and a compound represented by the above Chemical Formula 3-1 prepared according to Example 1-1 as a host was formed to be 40 nm thick thereon. Then, an electron transport layer was disposed to be 30 nm thick thereon by depositing a compound represented by the above Chemical Formula 5-5, and an electron injection layer was disposed to be 0.5 nm thick thereon by depositing a compound represented by the above Chemical Formula 5-6. On the lower electrode, an upper electrode was disposed by depositing MgAg to be 200 nm thick, fabricating an organic light emitting diode device. Herein, the red phosphorescence emission layer included the dopant in an amount of 10 wt % based on the entire weight of the emission layer. The electron injection layer was included in an amount of 50 wt % based on the entire weight of the electron transport layer and the electron injection layer.

[CHEMICAL FORMULA 5-7]

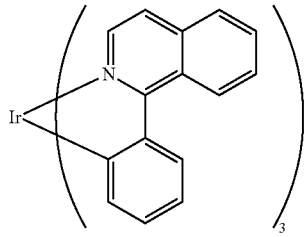

Example 3-2

An organic light emitting diode device was fabricated according to the same method as Example 3-1, except for using a compound represented by the above Chemical Formula 3-2 prepared according to Example 1-2 as a host.

Example 3-3

An organic light emitting diode device was fabricated according to the same method as Example 3-1, except for using a compound represented by the above Chemical Formula 3-3 prepared according to Example 1-3 as a host.

Example 3-4

An organic light emitting diode device was fabricated according to the same method as Example 3-1, except for using a compound represented by the above Chemical Formula 3-4 prepared according to Example 1-4 as a host.

Example 3-5

An organic light emitting diode device was fabricated according to the same method as Example 3-1, except for using a compound represented by the above Chemical Formula 3-5 prepared according to Example 1-5 as a host.

Example 3-6

An organic light emitting diode device was fabricated according to the same method as Example 3-1, except for using a compound represented by the above Chemical Formula 3-6 prepared according to Example 1-6 as a host.

Example 3-7

An organic light emitting diode device was fabricated according to the same method as Example 3-1, except for using a compound represented by the above Chemical Formula 3-7 prepared according to Example 1-7 as a host.

Example 3-8

An organic light emitting diode device was fabricated according to the same method as Example 3-1, except for using a compound represented by the above Chemical Formula 3-8 prepared according to Example 1-8 as a host.

Example 3-9

An organic light emitting diode device was fabricated according to the same method as Example 3-1, except for using a compound represented by the above Chemical Formula 3-9 prepared according to Example 1-9 as a host.

Example 3-10

An organic light emitting diode device was fabricated according to the same method as Example 3-1, except for using a compound represented by the above Chemical Formula 3-10 prepared according to Example 1-10 as a host.

Example 3-11

An organic light emitting diode device was fabricated according to the same method as Example 3-1, except for using a compound represented by the above Chemical Formula 3-11 prepared according to Example 1-11 as a host.

Example 3-12

An organic light emitting diode device was fabricated according to the same method as Example 3-1, except for using a compound represented by the above Chemical Formula 3-12 prepared according to Example 1-12 as a host.

Example 3-13

An organic light emitting diode device was fabricated according to the same method as Example 3-13, except for using a compound represented by the above Chemical Formula 3-2 prepared according to Example 1-13 as a host.

Example 3-14

An organic light emitting diode device was fabricated according to the same method as Example 3-1, except for using a compound represented by the above Chemical Formula 3-14 prepared according to Example 1-14 as a host.

Comparative Example 3

An organic light emitting diode device was fabricated according to the same method as Example 3-1, except for using a compound represented by the above Chemical Formula 4-2 prepared according to Comparative Example 1-2.

Evaluation 1

The organic light emitting diode devices according to Examples 2-1 to 2-14 and Comparative Example 2 were evaluated regarding luminous efficiency and color characteristic. The results are provided in the following Table 1.

TABLE 1

| | Voltage (V) | Efficiency (cd/A) | Color coordinates (CIE) | | Maximum emission wavelength (λmax) (nm) |
|---|---|---|---|---|---|
| | | | x | y | |
| Example 2-1 | 5.3 | 42 | 0.330 | 0.612 | 518 |
| Example 2-2 | 4.8 | 39 | 0.327 | 0.611 | 517 |
| Example 2-3 | 4.8 | 38 | 0.328 | 0.613 | 517 |
| Example 2-4 | 5.0 | 35 | 0.325 | 0.615 | 516 |
| Example 2-5 | 5.1 | 35 | 0.326 | 0.614 | 516 |
| Example 2-6 | 5.3 | 41 | 0.328 | 0.611 | 517 |
| Example 2-7 | 5.4 | 40 | 0.331 | 0.613 | 518 |
| Example 2-8 | 5.3 | 39 | 0.330 | 0.613 | 518 |
| Example 2-9 | 5.8 | 34 | 0.329 | 0.613 | 517 |
| Example 2-10 | 5.1 | 37 | 0.329 | 0.612 | 517 |
| Example 2-11 | 4.8 | 40 | 0.327 | 0.611 | 517 |
| Example 2-12 | 5.3 | 35 | 0.326 | 0.615 | 516 |
| Example 2-13 | 5.3 | 36 | 0.330 | 0.613 | 518 |
| Example 2-14 | 5.0 | 34 | 0.326 | 0.615 | 516 |
| Comparative Example 2 | 6.1 | 33 | 0.327 | 0.611 | 517 |

Referring to Table 1, the organic light emitting diode devices according to Examples 2-1 to 2-14 had higher efficiency and similar color coordinates to the one according to Comparative Example 2.

Evaluation 2

The organic light emitting diode devices according to Examples 3-1 to 3-14 and Comparative Example 3 were evaluated regarding luminous efficiency and color characteristic. The results are provided in the following Table 2.

TABLE 2

| | Voltage (V) | Efficiency (cd/A) | Color coordinates (CIE) | | Maximum emission wavelength (λmax) (nm) |
|---|---|---|---|---|---|
| | | | x | y | |
| Example 3-1 | 5.4 | 20 | 0.661 | 0.338 | 625 |
| Example 3-2 | 4.7 | 23 | 0.663 | 0.337 | 626 |
| Example 3-3 | 4.7 | 24 | 0.662 | 0.338 | 625 |
| Example 3-4 | 4.2 | 29 | 0.660 | 0.340 | 624 |
| Example 3-5 | 4.3 | 30 | 0.661 | 0.339 | 625 |
| Example 3-6 | 4.8 | 23 | 0.661 | 0.338 | 625 |
| Example 3-7 | 4.9 | 22 | 0.660 | 0.340 | 625 |
| Example 3-8 | 5.1 | 21 | 0.662 | 0.338 | 626 |
| Example 3-9 | 4.7 | 26 | 0.660 | 0.340 | 625 |
| Example 3-10 | 4.9 | 25 | 0.662 | 0.337 | 625 |
| Example 3-11 | 4.6 | 27 | 0.660 | 0.340 | 624 |
| Example 3-12 | 5.1 | 23 | 0.662 | 0.338 | 625 |
| Example 3-13 | 5.3 | 21 | 0.661 | 0.339 | 625 |
| Example 3-14 | 4.9 | 24 | 0.660 | 0.340 | 625 |
| Comparative Example 3 | 5.6 | 19 | 0.661 | 0.338 | 625 |

Referring to Table 2, the organic light emitting diode devices according to Examples 3-1 to 3-14 had higher efficiency and similar color coordinates to the one of Comparative Example 3.

While these embodiments have been described in connection with what is presently considered to be practical example embodiments, it is to be understood that the embodiments are not limited to the disclosed embodiments, but, on the contrary, is intended to cover various modifications and equivalent arrangements included within the spirit and scope of the appended claims.

What is claimed is:

1. A metal complex compound comprising one of the compounds represented by the following Chemical Formulae:

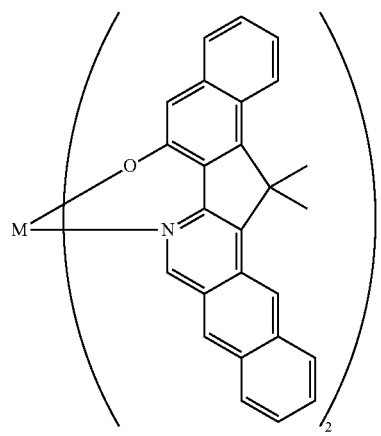

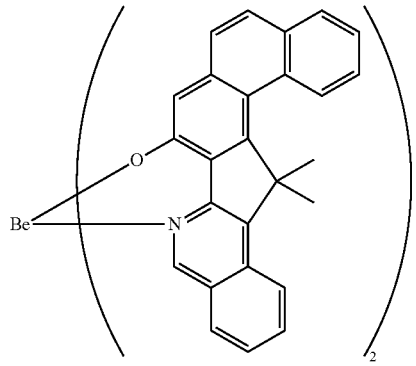

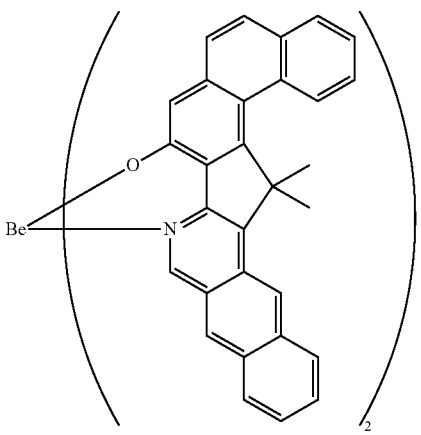

-continued

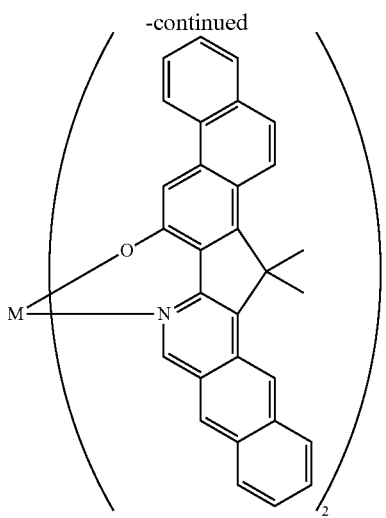

wherein M is Be.

2. An organic light emitting diode device, comprising:
a first electrode;
a second electrode facing the first electrode; and
an organic layer interposed between the first electrode and the second electrode,
wherein the organic layer comprises a metal complex compound comprising one of the compounds represented by the following Chemical Formulae:

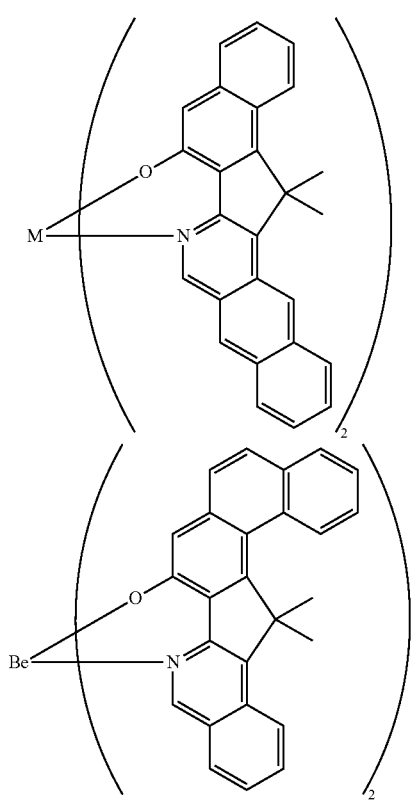

-continued

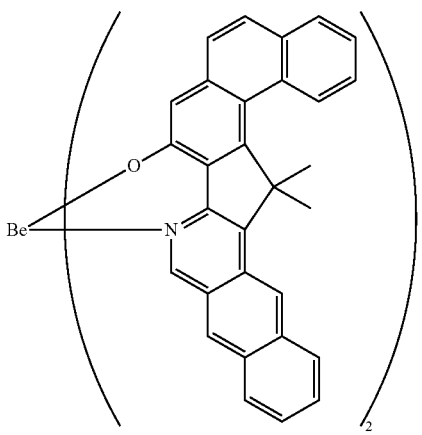

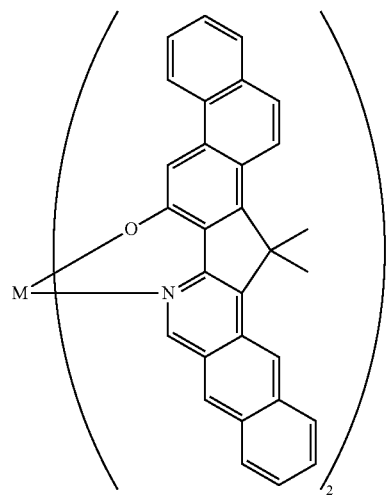

wherein,
M is Be.

3. The organic light emitting diode device of claim 2, wherein the organic layer comprises at least one of a hole injection layer, a hole transport layer, an emission layer, an electron transport layer, and an electron injection layer that are sequentially positioned on the first electrode.

4. The organic light emitting diode device of claim 3, wherein the metal complex compound is included in the emission layer.

5. The organic light emitting diode device of claim 3, wherein the metal complex compound is included in the electron transport layer.

* * * * *